US008883778B2

(12) United States Patent  
Claremon et al.

(10) Patent No.: US 8,883,778 B2  
(45) Date of Patent: Nov. 11, 2014

(54) CYCLIC INHIBITORS OF 11 BETA-HYDROXYSTEROID DEHYDROGENASE 1

(75) Inventors: David A. Claremon, Maple Glen, PA (US); Katerina Leftheris, San Diego, CA (US); Suresh B. Singh, Kendall Park, NJ (US); Colin M. Tice, Ambler, PA (US); Yuanjie Ye, Ambler, PA (US); Wei Zhao, Eagleville, PA (US); Linghang Zhuang, Chalfont, PA (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 325 days.

(21) Appl. No.: 13/381,123

(22) PCT Filed: Jun. 30, 2010

(86) PCT No.: PCT/US2010/040641  
§ 371 (c)(1),  
(2), (4) Date: May 17, 2012

(87) PCT Pub. No.: WO2011/002910  
PCT Pub. Date: Jan. 6, 2011

(65) Prior Publication Data  
US 2012/0232050 A1 Sep. 13, 2012

Related U.S. Application Data

(60) Provisional application No. 61/222,318, filed on Jul. 1, 2009.

(51) Int. Cl.  
C07D 413/10 (2006.01)  
C07D 413/04 (2006.01)  
C07D 241/04 (2006.01)  
A61K 31/675 (2006.01)  
A61K 31/5377 (2006.01)  
A61K 31/541 (2006.01)

(52) U.S. Cl.  
USPC ............................ 514/228.8; 544/96; 544/97

(58) Field of Classification Search  
USPC .................................. 544/96, 97; 514/228.8  
See application file for complete search history.

(56) References Cited

U.S. PATENT DOCUMENTS

| | | |
|---|---|---|
| 3,341,538 A | 9/1967 | Block et al. |
| 3,681,349 A | 8/1972 | Schwan et al. |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |

(Continued)

FOREIGN PATENT DOCUMENTS

| | | |
|---|---|---|
| DE | 1801556 A1 | 5/1970 |
| DE | 19918725 A1 | 10/2000 |

(Continued)

OTHER PUBLICATIONS

Shibata et al., "Cycloaddition of Oxetanes with Heterocumulenes Catalysed by Organotin Iodine-Lew Base Complex," Journal of Heterocyclic Chemistry, 1987, vol. 24, pp. 361-363.

(Continued)

Primary Examiner — Kahsay Habte  
(74) Attorney, Agent, or Firm — McCarter & English LLP; Steven G. Davis; Michael J. DeGrazia

(57) ABSTRACT

Disclosed are compounds represented by Formula (I):

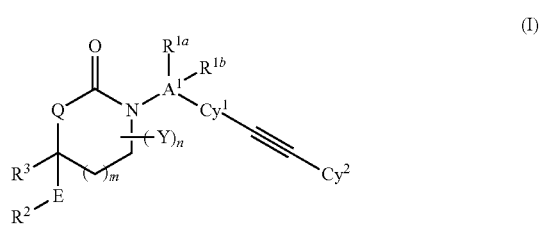

or pharmaceutically acceptable salts, enantiomers or diastereomers thereof. Also disclosed are pharmaceutical compositions comprising the compounds of Formula (I) or pharmaceutically acceptable salts, enantiomers or diastereomers thereof for the therapeutic treatment of diseases associated with the modulation or inhibition of 11β-HSD1 in mammals. Values for the variables of Formula (I) are defined herein.

16 Claims, No Drawings

(56) References Cited

U.S. PATENT DOCUMENTS

| | | |
|---|---|---|
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 7,026,310 B2 | 4/2006 | Emig et al. |
| 7,056,912 B2 | 6/2006 | Emig et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0264650 A1 | 10/2009 | Cho et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2010/0331320 A1 | 12/2010 | Renz et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0028445 A1 | 2/2011 | Eckhardt et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112062 A1 | 5/2011 | Claremon et al. |
| 2011/0112082 A1 | 5/2011 | Claremon et al. |
| 2011/0124635 A1 | 5/2011 | Claremon et al. |
| 2011/0190262 A1 | 8/2011 | Himmelsbach et al. |
| 2011/0224242 A1 | 9/2011 | Giethlen et al. |
| 2011/0263582 A1 | 10/2011 | Claremon et al. |
| 2011/0263583 A1 | 10/2011 | Claremon et al. |
| 2011/0263584 A1 | 10/2011 | Claremon et al. |
| 2011/0269736 A1 | 11/2011 | Eckhardt et al. |
| 2011/0269791 A1 | 11/2011 | Peters et al. |
| 2011/0269957 A1 | 11/2011 | Fandrick et al. |
| 2011/0275595 A1 | 11/2011 | Eckhardt et al. |

FOREIGN PATENT DOCUMENTS

| | | |
|---|---|---|
| DE | 19929348 A1 | 12/2000 |
| DE | 100 34 623 | 1/2002 |
| DE | 10034623 | 1/2002 |
| DE | 10034623 A1 | 1/2002 |
| EP | 0415642 A1 | 3/1991 |
| EP | 0454444 A1 | 10/1991 |
| EP | 0471591 A2 | 2/1992 |
| EP | 0640594 A1 | 3/1995 |
| EP | 0645387 A | 3/1995 |
| EP | 0645387 A1 | 3/1995 |
| EP | 0471591 B1 | 5/1995 |
| EP | 0928789 A1 | 7/1999 |
| EP | 1156049 A | 11/2001 |
| EP | 1156049 A1 | 11/2001 |
| EP | 1270724 A2 | 1/2003 |
| EP | 1852425 A | 11/2007 |
| EP | 1852425 A1 | 11/2007 |
| EP | 1 864 971 A1 | 12/2007 |
| EP | 1864971 A | 12/2007 |
| EP | 1864971 A1 | 12/2007 |
| EP | 1935420 | 6/2008 |
| EP | 1935420 A1 | 6/2008 |
| GB | 1077711 | 8/1967 |
| GB | 1077711 A | 8/1967 |
| JP | 6092945 A | 4/1994 |
| JP | 7157681 | 6/1995 |
| JP | 7157681 A | 6/1995 |
| JP | 2009110842 A2 | 4/1997 |
| JP | 09151179 | 6/1997 |
| JP | 09151179 A | 6/1997 |
| JP | 2002179572 A | 6/2002 |
| JP | 2002179572 A2 | 6/2002 |
| JP | 2003096058 | 4/2003 |
| JP | 2003096058 A | 4/2003 |
| JP | 2003300884 A | 10/2003 |
| JP | 2003300884 A2 | 10/2003 |
| JP | 2005-206503 A | 8/2005 |
| JP | 2005239670 | 9/2005 |
| JP | 2005239670 A | 9/2005 |
| JP | 2005272321 A | 10/2005 |
| JP | 2007 140188 | 6/2007 |
| JP | 2007140188 A | 6/2007 |
| JP | 2007 254409 | 10/2007 |
| JP | 2007254409 A | 10/2007 |
| JP | 2009110842 A | 5/2009 |
| WO | 92/07838 A1 | 5/1992 |
| WO | WO 92/07838 | 5/1992 |
| WO | 93/07128 A1 | 4/1993 |
| WO | WO 93/07128 | 4/1993 |
| WO | 93/13103 A1 | 7/1993 |
| WO | WO 93/13103 | 7/1993 |
| WO | 95/31440 A1 | 11/1995 |
| WO | WO 95/31440 | 11/1995 |
| WO | 96/14297 A1 | 5/1996 |
| WO | WO 96/14297 A | 5/1996 |
| WO | 96/23787 A1 | 8/1996 |
| WO | WO 96/23787 | 8/1996 |
| WO | 97/36605 A1 | 10/1997 |
| WO | WO 97/36605 | 10/1997 |
| WO | 98/57940 A1 | 12/1998 |
| WO | WO 98/57940 | 12/1998 |
| WO | 99/05125 A1 | 2/1999 |
| WO | 99/06395 A1 | 2/1999 |
| WO | WO 99/05125 | 2/1999 |
| WO | WO 99/06395 | 2/1999 |
| WO | 01/00595 A1 | 1/2001 |
| WO | WO 01/00595 A1 | 1/2001 |
| WO | 01/44200 A2 | 6/2001 |
| WO | WO 01/44200 A2 | 6/2001 |
| WO | 01/55063 A1 | 8/2001 |
| WO | WO 01/55063 | 8/2001 |
| WO | 02/06244 A1 | 1/2002 |
| WO | 02/06277 A1 | 1/2002 |
| WO | WO 02/06244 A1 | 1/2002 |
| WO | WO 02/06277 A1 | 1/2002 |
| WO | 02/22572 A2 | 3/2002 |
| WO | WO 02/22572 A2 | 3/2002 |

(56) References Cited

FOREIGN PATENT DOCUMENTS

| | | |
|---|---|---|
| WO | 03/043988 A1 | 5/2003 |
| WO | WO 03/043988 A1 | 5/2003 |
| WO | 03/057673 A1 | 7/2003 |
| WO | WO 03/057673 A | 7/2003 |
| WO | 03/093261 A1 | 11/2003 |
| WO | WO 03/093261 A1 | 11/2003 |
| WO | 2004/004722 A1 | 1/2004 |
| WO | 2004/009559 A2 | 1/2004 |
| WO | WO 2004/004722 A1 | 1/2004 |
| WO | WO 2004/009559 A2 | 1/2004 |
| WO | WO 2004/014859 A2 | 2/2004 |
| WO | 2004/046137 A1 | 6/2004 |
| WO | WO 2004/046137 | 6/2004 |
| WO | 2004/014859 A2 | 11/2004 |
| WO | 2004/094375 A2 | 11/2004 |
| WO | WO 2004/094375 A | 11/2004 |
| WO | 2005/000845 A2 | 1/2005 |
| WO | WO 2005/000845 | 1/2005 |
| WO | 2005/086700 A2 | 9/2005 |
| WO | WO 2005/086700 A2 | 9/2005 |
| WO | 2005/108361 A1 | 11/2005 |
| WO | WO 2005/108361 | 11/2005 |
| WO | WO 2005/108361 A | 11/2005 |
| WO | 2005/113525 A1 | 12/2005 |
| WO | WO 2005/113525 A1 | 12/2005 |
| WO | 2006/003494 A2 | 1/2006 |
| WO | WO 2006/003494 A2 | 1/2006 |
| WO | 2006/014357 A1 | 2/2006 |
| WO | WO 2006/014357 A | 2/2006 |
| WO | 2006/024627 A2 | 3/2006 |
| WO | 2006/024628 A1 | 3/2006 |
| WO | 2006/031715 A2 | 3/2006 |
| WO | WO 2006/024627 A2 | 3/2006 |
| WO | WO 2006/024628 A | 3/2006 |
| WO | WO 2006/031715 A | 3/2006 |
| WO | 2006/040329 A1 | 4/2006 |
| WO | 2006/044174 A2 | 4/2006 |
| WO | WO 2006/040329 | 4/2006 |
| WO | WO 2006/044174 | 4/2006 |
| WO | 2006/049952 A1 | 5/2006 |
| WO | WO 2006/049952 A | 5/2006 |
| WO | 2006/066924 A2 | 6/2006 |
| WO | 2006/066948 A1 | 6/2006 |
| WO | WO 2006/066924 A2 | 6/2006 |
| WO | WO 2006/066948 A1 | 6/2006 |
| WO | 2006/090792 A1 | 8/2006 |
| WO | WO 2006/090792 A1 | 8/2006 |
| WO | 2006/104280 A1 | 10/2006 |
| WO | 2006/109056 A1 | 10/2006 |
| WO | WO 2006/104280 A | 10/2006 |
| WO | WO 2006/109056 | 10/2006 |
| WO | 2007/008529 A2 | 1/2007 |
| WO | WO 2007/008529 A2 | 1/2007 |
| WO | 2007/048595 A1 | 5/2007 |
| WO | 2007/051810 A2 | 5/2007 |
| WO | 2007/061661 A2 | 5/2007 |
| WO | WO 2007/048595 | 5/2007 |
| WO | WO 2007/051810 | 5/2007 |
| WO | WO 2007/061661 A2 | 5/2007 |
| WO | 2007/068330 A1 | 6/2007 |
| WO | WO 2007/068330 A1 | 6/2007 |
| WO | 2007/079186 A2 | 7/2007 |
| WO | 2007/081569 A2 | 7/2007 |
| WO | 2007/081570 A2 | 7/2007 |
| WO | 2007/081571 A2 | 7/2007 |
| WO | 2007/084314 A2 | 7/2007 |
| WO | WO 2007/079186 A2 | 7/2007 |
| WO | WO 2007/081569 A2 | 7/2007 |
| WO | WO 2007/081570 A | 7/2007 |
| WO | WO 2007/081571 A2 | 7/2007 |
| WO | WO 2007/084314 A2 | 7/2007 |
| WO | 2007/109456 A2 | 9/2007 |
| WO | WO 2007/109456 A2 | 9/2007 |
| WO | 2007/118185 A2 | 10/2007 |
| WO | WO 2007/118185 A2 | 10/2007 |
| WO | 2007/124254 A2 | 11/2007 |
| WO | 2007/124329 A1 | 11/2007 |
| WO | 2007/124337 A1 | 11/2007 |
| WO | 2007/127693 A1 | 11/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |
| WO | 2008/000951 A2 | 1/2008 |
| WO | WO 2008/000951 | 1/2008 |
| WO | 2008/031227 A1 | 3/2008 |
| WO | 2008/036715 A1 | 3/2008 |
| WO | WO 2008/031227 A1 | 3/2008 |
| WO | WO 2008/036715 A1 | 3/2008 |
| WO | 2008/046758 A2 | 4/2008 |
| WO | WO 2008/046758 | 4/2008 |
| WO | WO 2008/046758 A3 | 4/2008 |
| WO | 2008/059948 A1 | 5/2008 |
| WO | WO 2008/059948 | 5/2008 |
| WO | 2008/106128 A2 | 9/2008 |
| WO | WO 2008/106128 A2 | 9/2008 |
| WO | 2008/118332 A2 | 10/2008 |
| WO | WO 2008/118332 A2 | 10/2008 |
| WO | 2009/017664 A1 | 2/2009 |
| WO | 2009/017671 A1 | 2/2009 |
| WO | WO 2009/017664 | 2/2009 |
| WO | WO 2009/017664 A1 | 2/2009 |
| WO | WO 2009/017671 | 2/2009 |
| WO | 2009/061498 A1 | 5/2009 |
| WO | 2009/063061 A2 | 5/2009 |
| WO | WO 2009/061498 | 5/2009 |
| WO | WO 2009/063061 | 5/2009 |
| WO | 2009/075835 A1 | 6/2009 |
| WO | WO 2009/075835 | 6/2009 |
| WO | 2009/088997 A1 | 7/2009 |
| WO | 2009/094169 A1 | 7/2009 |
| WO | WO 2009/088997 | 7/2009 |
| WO | WO 2009/094169 A | 7/2009 |
| WO | 2009/100872 A1 | 8/2009 |
| WO | 2009/102428 A2 | 8/2009 |
| WO | 2009/102460 A2 | 8/2009 |
| WO | WO 2009/100872 | 8/2009 |
| WO | WO 2009/102428 | 8/2009 |
| WO | WO 2009/102460 | 8/2009 |
| WO | 2009/117109 A1 | 9/2009 |
| WO | WO 2009/117109 | 9/2009 |
| WO | 2009/134384 A1 | 11/2009 |
| WO | 2009/134387 A1 | 11/2009 |
| WO | 2009/134392 A1 | 11/2009 |
| WO | 2009/134400 A1 | 11/2009 |
| WO | 2009/138386 A2 | 11/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | 2010/010149 A1 | 1/2010 |
| WO | 2010/010150 A1 | 1/2010 |
| WO | 2010/010157 A2 | 1/2010 |
| WO | 2010/010174 A1 | 1/2010 |
| WO | 2010/011314 A1 | 1/2010 |
| WO | WO 2010/010149 | 1/2010 |
| WO | WO 2010/010150 | 1/2010 |
| WO | WO 2010/010157 | 1/2010 |
| WO | WO 2010/010174 | 1/2010 |
| WO | WO 2010/011314 | 1/2010 |
| WO | 2010/023161 A1 | 3/2010 |
| WO | WO 2010/023161 | 3/2010 |
| WO | 2010/046445 A2 | 4/2010 |
| WO | WO 2010/046445 | 4/2010 |
| WO | 2010/091067 A2 | 8/2010 |
| WO | WO 2010/091067 | 8/2010 |
| WO | 2010/127237 A2 | 11/2010 |
| WO | WO 2010/127237 | 11/2010 |

OTHER PUBLICATIONS

Gavezzotti et al., "Are Crystal Structures Predictable?", Accounts of Chemical Research, 1994, vol. 27, pp. 309-314.

(56) References Cited

OTHER PUBLICATIONS

Vippagunta et al., "Crystalline Solids," Advanced Drug Deliver Reviews, 2001, vol. 48, pp. 3-26.
Office Action for U.S. Appl. No. 12/741,532, date of mailing Dec. 15, 2010.
Office Action for U.S. Appl. no. 12/771,499, date of mailing Dec. 21, 2010.
CA 154:284276, dated Aug. 10, 2009.
CA 1267843-31-1, dated Aug. 10, 2009.
Sullivan & Efner, "The Preparation of 6-Aryltetrahydro-1,3-oxazin-2-ones and Their Hydrolysis to 3-Substituted Propylamines," The Journal of Organic Chemistry, 33 (5): 2134-2136 (1968).
Wolfling et al., "Neighboring Group Participation Part 15. Stereoselective Synthesis of Some Steroidal Tetrahydrooxaziin-2-ones, as Novel Presumed Inhibitors of Human 5?-Reductase," Steroids, 69: 451-460 (2004).
International Search Report and Written Opinion—(PCT/US2010/040641) Date of Mailing Oct. 8, 2010.
U.S. Appl. No. 13/054,954, filed Jan. 20, 2011, Himmelsbach et al.
U.S. Appl. No. 13/059,233, filed Feb. 16, 2011, Eckhardt et al.
U.S. Appl. No. 13/147,637, filed Aug. 3, 2011, Eckhardt et al.
Bitar, "Glucocorticoid Dynamics and Impaired Wound Healing in Diabetes Mellitus", Am J Pathol., 1998, vol. 152, pp. 547-554.
Bitar et al., "Heat-Shock Protein 72/73 and Impaired Wound Healing in Diabetic and Hypercortisolemic States", Sugery, 1999, vol. 125, pp. 594-601.
Bitar et al., "Glucocorticoid-Dependent Impairment of Wound Healing in Experimental Diabetes: Amelioration by Adrenalectomy and RU 486", J Surg Res., 1999, vol. 82, pp. 234-243.
Bitar, "Insulin and Glucocorticoid-Dependent Suppression of the IGF-I System in Diabetic Wounds", Sugery, 2000, vol. 127, pp. 687-695.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract.
Chimica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract.
Zhurnal Organicheskoi Khimii, 1978, vol. 14(5), pp. 1092-1094.
Database CA [Online], Chemical Abstracts Service, Fukushima et al., "Preparation of Imidazolidinone Derivatives as 11.beta.-HSD1 Inhibitors", Oct. 6, 2009, XP 002531878.
"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Goubet et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Shue et al., "Cyclic Urea Derivatives as Potent NK1 Selective Antagonists", Bioorganic & Medicinal Chemistry Letters, 2005, vol. 15, pp. 3896-3899.
Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Wamil & Seckl, "Inhibition of 11β-hydroxysteroid Dehydrogenase Type 1 as a Promising Therapeutic Target", Drug Discovery Today, 2007, vol. 12, pp. 504-520.
Muehlstadt et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.
Schoellkopf et al., "Umsetzungen Alphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.
Suga et al., ""N-Acyliminium Ion Pool" as a Heterodiene in [4+2] Cycloaddition Reaction", Organic Letters, 2003, vol. 5, pp. 945-947.
Suga et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.
Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.
Yoshida et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.
Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.
International Search Report & Written Opinion—(PCT/US2008/009017) Date of Mailing Apr. 12, 2008.
International Search Report & Written Opinion—(PCT/US2008/002517) Date of Mailing Dec. 29, 2008.
International Search Report—(PCT/US2009/002653) Date of Mailing Jul. 3, 2009.
International Search Report—(PCT/US2009/002641) Date of Mailing Jul. 3, 2009.
International Search Report—(PCT/US2009/002629) Date of Mailing Jul. 3, 2009.
International Search Report—(PCT/US2009/002633) Date of Mailing Jul. 3, 2009.
International Search Report—(PCT/US2008/012618) Date of Mailing Dec. 3, 2009.
International Search Report—(PCT/US2009/000057) Date of Mailing Mar. 25, 2009.
International Search Report—(PCT/US2008/013539) Date of Mailing Mar. 19, 2009.
International Search Report—(PCT/US2009/000853) Date of Mailing Sep. 2, 2009.
International Search Report—(PCT/US2009/000421) Date of Mailing Apr. 15, 2009.
International Search Report—(PCT/US2009/000908) Date of Mailing Sep. 17, 2009.
International Search Report—(PCT/US2009/001712) Date of Mailing Jul. 14, 2009.
Database File Registry [Online], Chemical Abstracts Service, Columbus, Ohio, US, 2007, Database accession No. 958700-63-5, Abstract, XP002556893.
Database File Registry [Online], Chemical Abstracts Service, Columbus, Ohio, US, 2007, Database accession No. 958696-39-4, Abstract, XP002556894.
Database File Registry [Online], Chemical Abstracts Service, Columbus, Ohio, US, 2007, Database accession No. 958696-32-7, Abstract, XP002556895.
Database File Registry [Online], Chemical Abstracts Service, Columbus, Ohio, US, 2007, Database accession No. 958629-39-5, Abstract, XP002556896.
Database File Registry [Online], Chemical Abstracts Service, Columbus, Ohio, US, 2007, Database accession No. 958629-22-6, Abstract, XP002556897.
Database File Registry [Online], Chemical Abstracts Service, Columbus, Ohio, US, 2007, Database accession No. 958629-14-6, Abstract, XP002556898.

(56) References Cited

OTHER PUBLICATIONS

Database File Registry [Online], Chemical Abstracts Service, Columbus, Ohio, US, 2007, Database accession No. 958625-83-7, Abstract, XP002556899.

Database File Registry [Online], Chemical Abstracts Service, Columbus, Ohio, US, 2007, Database accession No. 958599-31-0, Abstract, XP002556900.

International Search Report—(PCT/US2010/023021) Date of Mailing Aug. 5, 2010.

International Search Report and Written Opinion—(PCT/US2008/009048) Date of Mailing Dec. 4, 2008.

International Search Report—(PCT/US2009/004261) Date of Mailing Oct. 21, 2009.

Shibata et al., "Cycloaddition of Oxetanes with Heterocumulenes Catalysed by Organotin Idoine-Lew Base Complex," Journal of Heterocyclic Chemistry, 1987, vol. 24, pp. 361-363.

Sullivan & Efner, "The Preparation of 6-Aryltetrahydro-1,3-oxazin-2-ones and Their Hydrolysis to 3-Substituted Propylamines," *The Journal of Organic Chemistry*, 33 (5): 2134-2136 (1968).

Wolfling et al., "Neighboring Group Participation Part 15. Stereoselective Synthesis of Some Steroidal Tetrahydrooxaziin-2-ones, as Novel Presumed Inhibitors of Human 5α-Reductase," *Steroids*, 69: 451-460 (2004).

Database CA [Online], Chemical Abstracts Service, Fukushima et al., "Preparation of Imidazolidinone Derivatives as 11.beta-HSD1 Inhibitors", Oct. 6, 2009, XP 002531878.

Kashima et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.

Wamil & Seckl, "Inhibition of 11?-hydroxysteroid Dehydrogenase Type 1 as a Promising Therapeutic Target", Drug Discovery Today, 2007, vol. 12, pp. 504-520.

Yoshida et al., "Selective synthesis of five- and six-membered cyclic carbamates by the reaction of 2-(1-haloalkyl) oxiranes with carbon dioxide and aliphatic primary amines", Heterocycles, Elsevier Science Ltd., 1993, vol. 35 (2), pp. 623-626.

CYCLIC INHIBITORS OF 11 BETA-HYDROXYSTEROID DEHYDROGENASE 1

RELATED APPLICATIONS

This application is the U.S. National Stage of International Application Ser. No. PCT/US2010/040641, filed Jun. 30, 2010, which claims priority to U.S. Application Ser. No. 61/222,318 filed Jul. 1, 2009, the entire contents of which are incorporated herein.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J. Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-

14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11β-HSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula (I) or pharmaceutically acceptable salts thereof, are effective inhibitors of 11β-HSD1.

The present invention is directed to compounds represented by the Structural Formula (I):

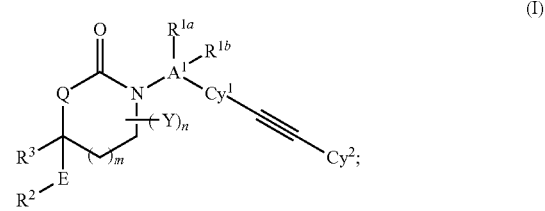

or a pharmaceutically acceptable salt, enantiomer or diastereomer thereof.

$R^{1a}$ and $R^{1b}$ are (a) absent if $A^1$ is a bond, or (b) independently selected from —H, $(C_1$-$C_6)$alkyl, $(C_2$-$C_6)$alkenyl, $(C_2$-$C_6)$alkynyl, or $(C_1$-$C_3)$alkoxy$(C_1$-$C_3)$alkyl, $(C_3$-$C_6)$cycloalkyl or $R^{1a}$ and $R^{1b}$ taken together with the carbon to which they are attached form a $(C_3$-$C_6)$cycloalkyl ring, and the $(C_1$-$C_6)$alkyl, $(C_2$-$C_6)$alkenyl, $(C_2$-$C_6)$alkynyl, $(C_1$-$C_3)$alkoxy$(C_1$-$C_3)$alkoxy, $(C_1$-$C_3)$alkoxy$(C_1$-$C_3)$alkyl, $(C_3$-$C_6)$cycloalkyl, or the cycloalkyl ring formed from $R^{1a}$, $R^{1b}$ and the carbon to which $R^{1a}$ and $R^{1b}$ are attached, are, independently, optionally substituted with up to four groups selected from H, fluorine, cyano, oxo, $(C_1$-$C_6)$alkyl, halo$(C_1$-$C_6)$alkyl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl, hydroxy$(C_1$-$C_6)$alkyl, $(C_1$-$C_6)$alkoxy$(C_1$-$C_6)$alkyl, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4—$, $(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NR^4—$, $R^4S(=O)_2NHC(=O)—$, $R^4S(=O)_2NHC(=O)O—$, $R^4S(=O)_2NHC(=O)NR^4—$, $R^4OS(=O)_2NHC(=O)—$, $R^4OS(=O)_2NHC(=O)O—$, $R^4OS(=O)_2NHC(=O)NR^4—$, $(R^4)_2NS(=O)_2NHC(=O)—$, $(R^4)_2NS(=O)_2NHC(=O)O—$, $(R^4)_2NS(=O)_2NHC(=O)NR^4—$, $R^4C(=O)NHS(=O)_2—$, $R^4C(=O)NHS(=O)_2O—$, $R^4C(=O)NHS(=O)_2NR^4—$, $R^4OC(=O)NHS(=O)_2—$, $R^4OC(=O)NHS(=O)_2O—$, $R^4OC(=O)NHS(=O)_2NR^4—$, $(R^4)_2NC(=O)NHS(=O)_2—$, $(R^4)_2NC(=O)NHS(=O)_2O—$, $(R^4)_2NC(=O)NHS(=O)_2NR^4—$, heterocyclyl, heteroaryl, arylamino and heteroarylamino.

$A^1$ is absent or a carbon atom.

$Cy^1$ is aryl, heteroaryl, monocyclic cycloalkyl or monocyclic heterocyclyl and is optionally substituted with 1 to 4 groups independently selected from halogen, —CN, —NO$_2$, —NH$_2$, —OH, —COOH, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl, hydroxy$(C_1$-$C_6)$alkoxy, $(C_4$-$C_7)$cycloalkylalkyl, $(C_4$-$C_7)$cycloalkylalkoxy, $(C_3$-$C_6)$cycloalkyl$(C_2$-$C_4)$alkynyl, halo$(C_1$-$C_6)$alkyl, halo$(C_2$-$C_6)$alkenyl, halo$(C_3$-$C_6)$cycloalkyl, halo$(C_4$-$C_7)$cycloalkylalkyl, halo$(C_1$-$C_6)$alkoxy, halo$(C_3$-$C_6)$cycloalkoxy, halo$(C_4$-$C_7)$cycloalkylalkoxy, $(C_1$-$C_6)$alkoxy$(C_1$-$C_6)$alkoxy, halo$(C_1$-$C_6)$alkoxy$(C_1$-$C_6)$alkoxy, $(C_1$-$C_6)$alkoxy$(C_1$-$C_6)$alkyl or halo $(C_1$-$C_6)$alkoxy$(C_1$-$C_6)$alkyl $(C_1$-$C_6)$alkylthio, $(C_3$-$C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1$-$C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R)_2$.

$Cy^2$ is $(C_1$-$C_6)$alkyl, $(C_2$-$C_6)$alkenyl, $(C_2$-$C_6)$alkynyl, $(C_1$-$C_3)$alkoxy$(C_1$-$C_3)$alkoxy, $(C_1$-$C_3)$alkoxy$(C_1$-$C_3)$alkyl, aryl, heteroaryl, cycloalkyl or heterocyclyl, and is optionally substituted with 1 to 4 groups independently selected from halogen, —CN, —NO$_2$, —NH$_2$, —OH, —COOH, —COOR$^6$, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl, hydroxy$(C_1$-$C_6)$alkoxy, $(C_4$-$C_7)$cycloalkylalkyl, $(C_4$-$C_7)$cycloalkylalkoxy, $(C_3$-$C_6)$cycloalkyl$(C_2$-$C_4)$alkynyl, halo$(C_1$-$C_6)$alkyl, halo$(C_2$-$C_6)$alkenyl, halo$(C_3$-$C_6)$cycloalkyl, halo$(C_4$-$C_7)$cycloalkylalkyl, halo$(C_1$-$C_6)$alkoxy, halo$(C_3$-$C_6)$cycloalkoxy, halo$(C_4$-$C_7)$cycloalkylalkoxy, $(C_1$-$C_6)$alkoxy$(C_1$-$C_6)$alkoxy, halo$(C_1$-$C_6)$alkoxy$(C_1$-$C_6)$alkoxy, $(C_1$-$C_6)$alkoxy$(C_1$-$C_6)$alkyl, halo$(C_1$-$C_6)$alkoxy$(C_1$-$C_6)$alkyl, $(C_1$-$C_6)$alkylthio, $(C_3$-$C_6)$cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NHR^7$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)R^7$, —$NHC(=O)NH_2$, —$NHC(=O)NHR^6$, —$NHC(=O)NR^6R^6$, oxooxazolidinyl, —$OC(=O)OR^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1$-$C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R)_2$;

E is (a) a bond or (b) $(C_1$-$C_3)$alkylene or $(C_1$-$C_2)$alkylenyloxy, wherein the O is attached to $R^2$, each of which is optionally substituted with 1 to 4 groups independently selected from methyl, ethyl, trifluoromethyl or oxo;

$R^2$ is $(C_1$-$C_6)$alkyl, aryl, heteroaryl, cycloalkyl or heterocyclyl and is optionally substituted with up to 4 groups independently selected from halogen, —CN, —NO$_2$, —NH$_2$, —OH, —COOH, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl, hydroxy$(C_1$-$C_6)$alkoxy, $(C_4$-$C_7)$cycloalkylalkyl, $(C_4$-$C_7)$cycloalkylalkoxy, $(C_3$-$C_6)$cycloalkyl$(C_2$-$C_4)$alkynyl, halo$(C_1$-$C_6)$alkyl, halo$(C_2$-$C_6)$alkenyl, halo$(C_3$-$C_6)$cycloalkyl, halo$(C_4$-$C_7)$cycloalkylalkyl, halo$(C_1$-$C_6)$alkoxy, halo$(C_3$-$C_6)$cycloalkoxy, halo$(C_4$-$C_7)$cycloalkylalkoxy, $(C_1$-$C_6)$alkoxy$(C_1$-$C_6)$alkoxy, halo$(C_1$-$C_6)$alkoxy$(C_1$-$C_6)$alkoxy, $(C_1$-$C_6)$alkoxy$(C_1$-$C_6)$alkyl, halo$(C_1$-$C_6)$alkoxy$(C_1$-$C_6)$alkyl, $(C_1$-$C_6)$alkylthio, $(C_3$-$C_6)$cycloalkylthio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1$-$C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R)_2$;

$R^3$ is selected from $(C_1$-$C_6)$alkyl, $(C_2$-$C_6)$alkenyl, $(C_2$-$C_6)$alkynyl, $(C_3$-$C_5)$cycloalkyl$(C_1$-$C_4)$alkyl, $(C_1$-$C_3)$alkoxy$(C_1$-$C_3)$alkoxy, or $(C_1$-$C_3)$alkoxy$(C_1$-$C_3)$alkyl and is optionally substituted with up to four groups independently selected from H, —F, —CN, oxo, $(C_1$-$C_6)$alkyl, halo$(C_1$-$C_6)$alkyl, amino$(C_1$-$C_6)$alkyl, $(C_1$-$C_6)$alkylamino$(C_1$-$C_6)$alkyl, di$(C_1$-$C_6)$alkylamino$(C_1$-$C_6)$alkyl, hydroxy$(C_1$-$C_6)$alkyl and $(C_1$-$C_6)$alkoxy$(C_1$-$C_6)$alkyl, $R^4O—$, $(R^4)_2N—$, $R^4O_2O—$, $R^4C(=O)O—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NC(=NCN)NR^4—$, $(R^4O)_2P(=O)O—$, $(R^4O)_2P(=O)NR^4—$, $R^4OS(=O)_2NR^4—$, $(R^4)_2NS(=O)_2O—$, $(R^4)_2NS(=O)_2NR^4—$, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo);

Y is $(C_1-C_6)$alkyl, halo$(C_1-C_6)$alkyl or oxo.

n is 0, 1 or 2 m is 1 or 2.

Q is O, $CH_2$ or $NR^5$.

Each $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl.

Each $R^5$ is independently H, $(C_1-C_6)$alkyl, halo$(C_1-C_6)$alkyl or hydroxy$(C_1-C_6)$alkyl.

Each $R^6$ is independently $(C_1-C_6)$alkyl, $(C_2-C_6)$alkenyl, $(C_2-C_6)$alkynyl or $(C_1-C_6)$alkoxy.

$V^1$ is $(C_1-C_6)$alkylene, $(C_1-C_6)$alkenylene, $(C_1-C_6)$alkynylene or $(C_1-C_6)$alkyleneoxy.

Each $R^7$ is independently $(C_3-C_6)$cycloalkyl or $(C_3-C_6)$cycloalkoxy.

$R^8$ is heterocyclyl.

$R^9$ is $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl or halo$(C_1-C_6)$alkoxy$(C_1-C_6)$alkyl.

Another embodiment of the invention is a pharmaceutical composition comprising i) a pharmaceutically acceptable carrier or diluent, and ii) a compound of Formulas (I), (II), (II-A), (II-B), (II-C), (II-D), (III), (III-A), (III-B), (III-C), (III-D), (III-E) (IV), (IV-A), (IV-B), (IV-C), (IV-D), (V), (V-A), (V-B), (V-C) or (V-D), or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas (I), (II), (II-A), (II-B), (II-C), (II-D), (III), (III-A), (III-B), (III-C), (III-D), (III-E) (IV), (IV-A), (IV-B), (IV-C), (IV-D), (V), (V-A), (V-B), (V-C) or (V-D), or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of an 11β-HSD1 inhibitor disclosed herein.

Another embodiment of the invention is the use of a compound of an 11β-HSD1 inhibitor disclosed herein for the manufacture of a medicament for inhibiting 11β-HSD1 activity in a mammal in need of such treatment.

Another embodiment of the invention is the use of an 11β-HSD1 inhibitor disclosed herein for the manufacture of a medicament for treating a subject with a disease associated with the activity or expression of 11β-HSD1.

Another embodiment of the invention is an 11β-HSD1 disclosed herein for use in inhibiting 11β-HSD1 activity in a mammal in need of such treatment.

Another embodiment of the invention is an 11β-HSD1 inhibitor disclosed herein for use in for treating a subject with a disease associated with the activity or expression of 11β-HSD1.

DETAILED DESCRIPTION OF THE INVENTION

The present invention is directed to compounds represented by the Structural Formula (I) or a pharmaceutically acceptable salt, enantiomer or diastereomer thereof. Values and particular values for the variables in Structural Formula I or an enantiomer, a diastereomer, or a pharmaceutically acceptable salt thereof are provided in the following paragraphs. It is understood that the invention encompasses all combinations of the substituent variables (i.e., $Cy^1$, R2, R3, etc.) defined herein. For Structural Formula (I):

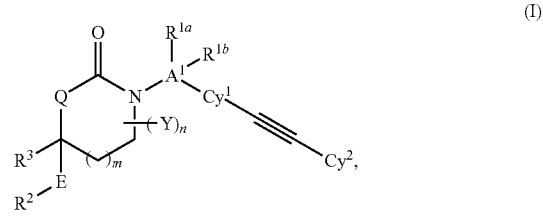

(I)

or a pharmaceutically acceptable salt, enantiomer or diastereomer thereof:

$R^{1a}$ and $R^{1b}$ are (a) absent if $A^1$ is a bond, or (b) independently selected from —H, $(C_1-C_6)$alkyl, $(C_2-C_6)$alkenyl, $(C_2-C_6)$alkynyl, or $(C_1-C_3)$alkoxy$(C_1-C_3)$alkyl, $(C_3-C_6)$cycloalkyl or $R^{1a}$ and $R^{1b}$ taken together with the carbon to which they are attached form a $(C_3-C_6)$cycloalkyl ring, and the $(C_1-C_6)$alkyl, $(C_2-C_6)$alkenyl, $(C_2-C_6)$alkynyl, $(C_1-C_3)$alkoxy$(C_1-C_3)$alkoxy, $(C_1-C_3)$alkoxy$(C_1-C_3)$alkyl, $(C_3-C_6)$cycloalkyl, or the cycloalkyl ring formed from $R^{1a}$, $R^{1b}$ and the carbon to which $R^{1a}$ and $R^{1b}$ are attached, are, independently, optionally substituted with up to four groups selected from H, fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NC=N)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)$ O—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino;

In one particular embodiment, $R^{1b}$ is hydrogen.

In a more particular embodiment, $R^{1b}$ is hydrogen and $R^{1a}$ is optionally substituted $(C_1-C_6)$alkyl.

In a more particular embodiment, $R^{1b}$ is hydrogen and $R^{1a}$ is an optionally substituted methyl or ethyl group.

In a more particular embodiment, $R^{1b}$ is hydrogen and $R^{1a}$ is methyl.

In a another particular embodiment, $R^{1a}$ and $R^{1b}$ are, independently, optionally substituted methyl or ethyl.

In an even more particular embodiment, $R^{1a}$ and $R^{1b}$ are, independently, optionally substituted methyl.

In an even more particular embodiment, $R^{1a}$ and $R^{1b}$ are methyl.

In one particular embodiment, $R^{1a}$ is optionally substituted $(C_3-C_5)$cycloalkyl.

In a more particular embodiment, $R^{1a}$ is optionally substituted cyclopropyl.

In another particular embodiment, $R^{1a}$ is $(C_3-C_7)$cycloalkyl optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—.

In a more particular embodiment, $R^{1a}$ is $(C_3-C_5)$cycloalkyl optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—.

In an even more particular embodiment, $R^{1a}$ is cyclopropyl optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—.

In another particular embodiment, $R^{1a}$ is unsubstituted $(C_3-C_7)$cycloalkyl.

In a more particular embodiment, $R^{1a}$ is unsubstituted $(C_3-C_5)$cycloalkyl.

In an even more particular embodiment, $R^{1a}$ is unsubstituted cyclopropyl.

$R^{1b}$ is hydrogen, $(C_1-C_6)$alkyl, $(C_2-C_6)$alkenyl, $(C_2-C_6)$alkynyl or $(C_1-C_3)$alkoxy$(C_1-C_3)$alkyl, and the $(C_1-C_6)$alkyl, $(C_2-C_6)$alkenyl, $(C_2-C_6)$alkynyl and $(C_1-C_3)$alkoxy$(C_1-C_3)$alkyl, and the group represented by $R^{1b}$ is optionally substituted with up to four groups independently selected from —H, fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NC(=NCN)NR^4$—, $(R^4O)_2P(=O)O$—, $(R^4O)_2P(=O)NR^4$—, $R^4OS(=O)_2NR^4$—, $(R^4)_2NS(=O)_2O$—, $(R^4)_2NS(=O)_2NR^4$—, $R^4S(=O)_2NR^4$—, $R^4S(=O)_2NHC(=O)$—, $R^4S(=O)_2NHC(=O)O$—, $R^4S(=O)_2NHC(=O)NR^4$—, $R^4OS(=O)_2NHC(=O)$—, $R^4OS(=O)_2NHC(=O)O$—, $R^4OS(=O)_2NHC(=O)NR^4$—, $(R^4)_2NS(=O)_2NHC(=O)$—, $(R^4)_2NS(=O)_2NHC(=O)O$—, $(R^4)_2NS(=O)_2NHC(=O)NR^4$—, $R^4C(=O)NHS(=O)_2$—, $R^4C(=O)NHS(=O)_2O$—, $R^4C(=O)NHS(=O)_2NR^4$—, $R^4OC(=O)NHS(=O)_2$—, $R^4OC(=O)NHS(=O)_2O$—, $R^4OC(=O)NHS(=O)_2NR^4$—, $(R^4)_2NC(=O)NHS(=O)_2$—, $(R^4)_2NC(=O)NHS(=O)_2O$—, $(R^4)_2NC(=O)NHS(=O)_2NR^4$—, heterocyclyl, heteroaryl, arylamino and heteroarylamino.

In one particular embodiment, $R^{1b}$ is hydrogen or optionally substituted $(C_1-C_6)$alkyl.

In a more particular embodiment, $R^{1b}$ is hydrogen or optionally substituted methyl.

In another particular embodiment, $R^{1b}$ is hydrogen or $(C_1-C_6)$alkyl optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—.

In a more particular embodiment, $R^{1b}$ is hydrogen or methyl optionally substituted with up to three groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—.

In another particular embodiment, $R^{1b}$ is $(C_1-C_6)$alkyl optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—.

In a more particular embodiment, $R^{1b}$ is methyl optionally substituted with up to three groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl and $R^4O$—.

In another particular embodiment, $R^{1b}$ is unsubstituted $(C_1-C_6)$alkyl.

In a more particular embodiment, $R^{1b}$ is unsubstituted methyl.

In an even more particular embodiment, $R^{1b}$ is H.

In another particular embodiment, $R^{1b}$ is hydrogen and $R^{1a}$ is $(C_3-C_6)$cycloalkyl.

In another particular embodiment, $R^{1b}$ is hydrogen and $R^{1a}$ is cyclopropyl.

In another particular embodiment, $R^{1a}$ and $R^{1b}$ are $(C_1-C_6)$alkyl, the groups represented by $R^{1a}$ and $R^{1b}$, independently, optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In a more particular embodiment, $R^{1a}$ and $R^{1b}$ are methyl or ethyl, the groups represented by $R^{1a}$ and $R^{1b}$, independently, optionally substituted with up to four groups independently selected from fluorine, cyano, oxo, $R^4$, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In an even more particular embodiment, $R^{1a}$ and $R^{1b}$ are methyl, independently, optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In another particular embodiment, $R^{1a}$ and $R^{1b}$ are unsubstituted methyl.

In another particular embodiment, $R^{1a}$ and $R^{1b}$ taken together with the carbon to which they are attached form an optionally substituted ($C_3$-$C_6$)cycloalkyl ring.

In another particular embodiment, $R^{1a}$ and $R^{1b}$ taken together with the carbon to which they are attached form an ($C_3$-$C_6$)cycloalkyl ring optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In a more particular embodiment, $R^{1a}$ and $R^{1b}$ taken together with the carbon to which they are attached form an unsubstituted ($C_3$-$C_6$)cycloalkyl ring.

In another particular embodiment, $R^{1a}$ and $R^{1b}$ taken together with the carbon to which they are attached form a cyclopropyl ring optionally substituted with up to four groups independently selected from fluorine, cyano, oxo, $R^4$, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—.

In a more particular embodiment, $R^{1a}$ and $R^{1b}$ taken together with the carbon to which they are attached form an unsubstituted cyclopropyl ring.

In another particular embodiment, $R^{1a}$ and $R^{1b}$ are, independently, hydrogen, optionally substituted methyl or optionally substituted ethyl, or $R^{1a}$ and $R^{1b}$ taken together with the carbon to which they are attached form an optionally substituted cyclopropyl group; provided that both $R^{1a}$ and $R^{1b}$ are not hydrogen and if $R^{1a}$ or $R^{1b}$ is hydrogen then $A^1$ is ethynyl.

In a more particular embodiment, $R^{1a}$ and $R^{1b}$ are, independently, hydrogen or methyl, or $R^{1a}$ and $R^{1b}$ taken together with the carbon to which they are attached form cyclopropyl.

In another more particular embodiment, $R^{1a}$ and $R^{1b}$ are hydrogen.

$A^1$ is absent or a carbon atom;

In one particular embodiment, $A^1$ is a bond.

In another particular embodiment, $A^1$ is a carbon atom.

$Cy^1$ is aryl, heteroaryl, monocyclic cycloalkyl or monocyclic heterocyclyl and is optionally substituted with 1 to 4 groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl ($C_2$-$C_4$)alkynyl, halo($C_1$-$C_6$)alkyl, halo($C_2$-$C_6$)alkenyl, halo ($C_3$-$C_6$)cycloalkyl, halo($C_4$-$C_7$)cycloalkylalkyl, halo($C_1$-$C_6$) alkoxy, halo($C_3$-$C_6$)cycloalkoxy, halo($C_4$-$C_7$) cycloalkylalkoxy, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxy($C_1$-$C_6$)alkyl or halo ($C_1$-$C_6$)alkoxy($C_1$-$C_6$)alkyl ($C_1$-$C_6$)alkylthio, ($C_3$-$C_6$) cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —NHC $(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)NHR^7$, —$C(=O)NR^6R^7$, —$C(=O)$ $N(R^7)_2$, —$S(=O)_2NHR^7$, —$S(=O)_2NR^6R^7$, —$S(=O)_2N$ $(R^7)_2$, cyano($C_1$-$C_6$)alkyl, —$V^1$—$C(=O)NH_2$, —$V^1$—C $(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R)_2$.

In one particular embodiment, $Cy^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group.

In a more particular embodiment, $Cy^1$ is an optionally substituted cyclohexyl, phenyl, pyridyl, pyrimidinyl, thiazolyl, triazolyl or benzothiazolyl group.

In an even more particular embodiment, $Cy^1$ is an optionally substituted phenyl.

In a more particular embodiment, the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, the group represented by $Cy^1$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In a more particular embodiment, $Cy^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, $Cy^1$ is an optionally substituted cyclohexyl, piperidinyl, pyrrolidinyl, phenyl, naphthyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl or triazolopyridinyl group, and the group represented by $Cy^1$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In a more particular embodiment, $Cy^1$ is an optionally substituted cyclohexyl, phenyl, pyridyl, pyrimidinyl, thiazolyl, triazolyl or benzothiazolyl group, and the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, $Cy^1$ is an optionally substituted cyclohexyl, phenyl, pyridyl, pyrimidinyl, thiazolyl, triazolyl or benzothiazolyl group, and the group represented by $Cy^1$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In a more particular embodiment, $Cy^1$ is phenyl optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, trifluoromethoxy, trifluoroethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl.

In another particular embodiment, $Cy^1$ is phenyl optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another particular embodiment, $Cy^1$ is phenyl optionally substituted with fluoro, chloro, or methyl.

In an even more particular embodiment, $Cy^1$ is phenyl.

$Cy^2$ is $(C_1-C_6)$alkyl, $(C_2-C_6)$alkenyl, $(C_2-C_6)$alkynyl, $(C_1-C_3)$alkoxy$(C_1-C_3)$alkoxy, $(C_1-C_3)$alkoxy$(C_1-C_3)$alkyl, aryl, heteroaryl, cycloalkyl or heterocyclyl, and is optionally substituted with 1 to 4 groups independently selected from halogen, —CN, —$NO_2$, —$NH_2$, —OH, —COOH, —$COOR^6$, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NHR^7$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)R^7$, —$NHC(=O)NH_2$, —$NHC(=O)NHR^6$, —$NHC(=O)NR^6R^6$, oxooxazolidinyl, —$OC(=O)OR^6$,—$V^1$—$NHC(=O)R^6$,—$NHS(=O)_2R^6$, —$V^1$—$NHS(=O)_2R^6$, —$V^1$—$C(=O)R^6$, heteroaryl, aryl, heterocyclyl, oxo, —$V^1$—NH2, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano$(C_1-C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$.

In one particular embodiment, $Cy^2$ is an optionally substituted methyl, ethyl, propyl, butyl, pentyl, hexyl, cyclopropyl, cyclobutyl, cyclopentyl, cyclohexyl, phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, or 1,1-dioxo-hexahydro-1,2-thiazinyl group.

In another particular embodiment, $Cy^2$ is $(C_1-C_6)$alkyl, $(C_2-C_6)$alkenyl, $(C_2-C_6)$alkynyl, $(C_1-C_3)$alkoxy$(C_1-C_3)$alkoxy, $(C_1-C_3)$alkoxy$(C_1-C_3)$alkyl, aryl, heteroaryl, cycloalkyl or heterocyclyl, and is optionally substituted with 1 to 4 groups independently selected from —$NH_2$, —OH, —COOH, —$COOR^6$, —$R^6$, —$C(=O)NHR^7$; —$C(=O)NR^6R^6$, —$C(=O)R^8$, —$NHC(=O)R^6$, —$NHC(=O)R^7$, —$NHC(=O)NH_2$, —$NHC(=O)NHR^6$, —$NHC(=O)NR^6R^6$, oxooxazolidinyl, —$OC(=O)OR^6$, and —$NHS(=O)_2R^6$.

In another particular embodiment, $Cy^2$ is $(C_1-C_6)$alkyl, $(C_2-C_6)$alkenyl, $(C_2-C_6)$alkynyl, $(C_1-C_3)$alkoxy$(C_1-C_3)$alkoxy, $(C_1-C_3)$alkoxy$(C_1-C_3)$alkyl, aryl, heteroaryl, cycloalkyl or heterocyclyl, and is optionally substituted with 1 to 4 groups independently selected from —$NH_2$, —OH, —COOH, —COOMe, —OMe, cyclopropylcarbamoyl; —$C(=O)NMe_2$, azetidinylcarbonyl, —$NHC(=O)Me$, —$NHC(=O)OMe$, cyclopropanecarboxamido, —$NHC(=O)NH_2$, —$NHC(=O)NHMe$, —$NHC(=O)NMe_2$, oxooxazolidinyl, —$OC(=O)OMe$, and —$NHS(=O)_2Me$.

In another particular embodiment, $Cy^2$ is an optionally substituted methyl, ethyl, cyclopentyl, cyclohexyl, phenyl, pyridyl, oxodihydropyridyl, piperidinyl, azetidinyl or tetrahydropyranyl group.

In a more particular embodiment, $Cy^2$ is an optionally substituted methyl, ethyl, cyclopentyl, cyclohexyl, phenyl, pyridyl, oxodihydropyridyl, piperidinyl, azetidinyl or tetrahydropyranyl group, and is optionally substituted with 1 to 4 groups independently selected from —$NH_2$, —OH, —COOH, —$COOR^6$, —$R^6$, —$C(=O)NHR^7$; —$C(=O)NR^6R^6$, —$C(=O)R^8$, —$NHC(=O)R^6$, —$NHC(=O)R^7$, —$NHC(=O)NH_2$, —$NHC(=O)NHR^6$, —$NHC(=O)NR^6R^6$, oxooxazolidinyl, —$OC(=O)OR^6$, and —$NHS(=O)_2R^6$.

In an even more particular embodiment, $Cy^2$ is an optionally substituted methyl, ethyl, cyclopentyl, cyclohexyl, phenyl, pyridyl, oxodihydropyridyl, piperidinyl, azetidinyl or tetrahydropyranyl group, and is optionally substituted with 1 to 4 groups independently selected from —$NH_2$, —OH, —COOH, —COOMe, —OMe, cyclopropylcarbamoyl; —$C(=O)NMe_2$, azetidinylcarbonyl, —$NHC(=O)Me$, —$NHC(=O)OMe$, cyclopropanecarboxamido, —$NHC(=O)NH_2$, —$NHC(=O)NHMe$, —$NHC(=O)NMe_2$, oxooxazolidinyl, —$OC(=O)OMe$, and —$NHS(=O)_2Me$.

In another particular embodiment, $Cy^2$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl group, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, 1,1-dioxo-hexahydro-1,2-thiazinyl, or cyclopropyl group, and the group represented by $Cy^2$ is optionally substituted with 1 to 4 groups independently selected from methyl, ethyl, propyl, cyclopropyl, halo, hydroxy, methoxy, hydroxymethyl, methoxycarbonyl, amino, aminomethyl, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethyl-amino-sulfonyl, pyrrolidine-1-sulfonyl, methylsulfonylaminomethyl, tetrazolyl, trifluoromethyl, acetyl, 2-hydroxyethyl, 1-aminoethyl, deuteromethyl, t-butyl, difluoromethyl, 2-fluoroethyl, 2,2,2-trifluoroethyl, 2-hydroxy-2- propyl, 2-hydroxy-2-methylpropyl, 2-methoxy-2-methylpropyl, 3-methoxy-2-methylpropyl, oxetanyl, 1-imidazolyl, 2-methyl-1-imidazolyl, 2,4-dimethyl-1-imidazolyl, ethylaminocarbonyl, cyclopropylaminocarbonyl, t-butylaminocarbonyl, 2-hydroxyethoxy, 2-hydroxy-2-methylpropoxy, 3-methoxy-2-methylpropoxy, ethoxy, 1,1-dimethyl-2-hydroxyethoxy, cyclopropylmethoxy, difluoromethoxy, 2-fluoroethoxy, 3-oxetanyloxy, (3-methyl-3-oxetanyl)methoxy, cyano, 2-cyano-2-propyl, cyclopropylmethyl, methylsulfinyl, methylthio, 1-amino-2-methyl-1-oxopropan-2-yl.

In yet another particular embodiment, the group represented by $Cy^2$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In a more particular embodiment, $Cy^2$ is an optionally substituted phenyl or oxodihydropyridyl group, and the group represented by $Cy^2$ is optionally substituted with one to four groups independently selected from halogen, —CN, —$NO_2$, —$NH_2$, —OH, —COOH, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl and hydroxy$(C_1$-$C_6)$alkoxy.

In a more particular embodiment, $Cy^2$ is an optionally substituted phenyl or oxodihydropyridyl group, and the group represented by $Cy^2$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another particular embodiment, $Cy^2$ is an optionally substituted phenyl, and the group represented by $Cy^2$ is optionally substituted with one to four groups independently selected from halogen, —CN, —$NO_2$, —$NH_2$, —OH, —COOH, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl and hydroxy$(C_1$-$C_6)$alkoxy.

In a more particular embodiment, $Cy^2$ is an optionally substituted phenyl, and the group represented by $Cy^2$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another particular embodiment, $Cy^2$ is an optionally substituted oxodihydropyridyl group, and the group represented by $Cy^2$ is optionally substituted with one to four groups independently selected from halogen, —CN, —$NO_2$, —$NH_2$, —OH, —COOH, $(C_1$-$C_6)$alkyl, halo$(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl and hydroxy$(C_1$-$C_6)$alkoxy.

In a more particular embodiment, $Cy^2$ is an optionally substituted oxodihydropyridyl group, and the group represented by $Cy^2$ is optionally substituted with fluoro, chloro, cyano, $CONH_2$, CONHMe, $CONMe_2$, CONHc-Pr, methyl, ethyl, cyclopropyl, difluoromethyl, $CF_3$ or oxo.

In another more particular embodiment, $Cy^2$ is an optionally substituted oxodihydropyridyl group, and the group represented by $Cy^2$ is optionally substituted with $(C_1$-$C_6)$alkyl, halo$(C_1$-$C_6)$alkyl or $(C_3$-$C_6)$cycloalkyl.

In another particular embodiment, $Cy^2$ is oxodihydropyridyl optionally substituted with fluoro, chloro, bromo, cyano, $CONH_2$, CONHMe, $CONMe_2$, methyl, ethyl, cyclopropyl, $CHF_2$, $CHF_2CH_2$, $CH_2CF_3$, $CH_2CH_2F$ or $CF_3$.

In another particular embodiment, $Cy^2$ is oxodihydropyridyl optionally substituted at the ring nitrogen with methyl, ethyl, propyl, cyclopropyl, difluoromethyl, 2-fluoroethyl or 2,2,2-trifluoroethyl.

In another particular embodiment, $Cy^2$ is oxodihydropyridyl optionally substituted at the ring nitrogen with methyl, ethyl, propyl or cyclopropyl.

E is (a) a bond or (b) $(C_1$-$C_3)$alkylene or $(C_1$-$C_2)$alkylenyloxy, wherein the O is attached to $R^2$, each of which is optionally substituted with 1 to 4 groups independently selected from methyl, ethyl, trifluoromethyl or oxo.

In one particular embodiment, E is a bond or unsubstituted $(C_1$-$C_3)$alkylene.

In a more particular embodiment, E is a bond or $CH_2$.

In an even more particular embodiment, E is a bond.

$R^2$ is $(C_1$-$C_6)$alkyl, aryl, heteroaryl, cycloalkyl or heterocyclyl and is optionally substituted with up to 4 groups independently selected halogen, —CN, —$NO_2$, —$NH_2$, —OH, —COOH, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl, hydroxy$(C_1$-$C_6)$alkoxy, —$R^9$, $(C_1$-$C_6)$alkylthio, $(C_3$-$C_6)$cycloalkythio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)$, —$C(=O)R^6$, —$C(=O)NH_2$, —$S(=O)_2NH_2$, —$C(=O)NHR^6$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—NH2, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R)_2$, cyano$(C_1$-$C_6)$alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$.

In one particular embodiment, $R^2$ is an optionally substituted $(C_1$-$C_6)$alkyl, aryl, heteroaryl or cycloalkyl group.

In a more particular embodiment, $R^2$ is an optionally substituted phenyl, fluorophenyl, isopropyl, cyclopropyl, t-butyl or trifluoroethyl group, or E-$R^2$ is optionally substituted cyclopropylmethyl.

In another particular embodiment, $R^2$ is an optionally substituted phenyl or fluorophenyl group.

In another particular embodiment, $R^2$ is an optionally substituted $(C_1$-$C_6)$alkyl, aryl, heteroaryl or cycloalkyl group; each optionally substituted with up to four groups independently selected from halogen, —CN, —$NO_2$, —$NH_2$, —OH, —COOH, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl, hydroxy$(C_1$-$C_6)$alkoxy, $(C_4$-$C_7)$cycloalkylalkyl, $(C_4$-$C_7)$cycloalkylalkoxy, $(C_3$-$C_6)$cycloalkyl$(C_2$-$C_4)$alkynyl, halo$(C_1$-$C_6)$alkyl, halo$(C_2$-$C_6)$alkenyl, halo$(C_3$-$C_6)$cycloalkyl, halo$(C_4$-$C_7)$cycloalkylalkyl, halo$(C_1$-$C_6)$alkoxy, halo$(C_3$-$C_6)$cycloalkoxy, halo$(C_4$-$C_7)$cycloalkylalkoxy, $(C_1$-$C_6)$alkoxy$(C_1$-$C_6)$alkoxy, halo$(C_1$-$C_6)$alkoxy$(C_1$-$C_6)$alkoxy, $(C_1$-$C_6)$alkoxy$(C_1$-$C_6)$alkyl, halo$(C_1$-$C_6)$alkoxy$(C_1$-$C_6)$alkyl, $(C_1$-$C_6)$alkylthio, and $(C_3$-$C_6)$cycloalkythio.

In a more particular embodiment, $R^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from halogen, —CN, —$NO_2$, —$NH_2$, —OH, —COOH, $(C_1$-$C_6)$alkyl, $(C_2$-$C_6)$alkenyl, $(C_2$-$C_6)$alkynyl, $(C_1$-$C_6)$alkoxy, $(C_3$-$C_6)$cycloalkyl, $(C_3$-$C_6)$cycloalkoxy, hydroxy$(C_1$-$C_6)$alkyl, hydroxy$(C_3$-$C_6)$cycloalkyl, hydroxy$(C_2$-$C_6)$alkenyl, hydroxy$(C_1$-$C_6)$alkoxy, $(C_4$-$C_7)$cycloalkylalkyl, $(C_4$-$C_7)$cycloalkylalkoxy, $(C_3$-$C_6)$cycloalkyl$(C_2$-$C_4)$alkynyl, halo$(C_1$-$C_6)$alkyl, halo$(C_2$-$C_6)$alkenyl, halo$(C_3$-$C_6)$cycloalkyl, halo$(C_4$-$C_7)$cycloalkylalkyl, halo$(C_1$-$C_6)$ alkoxy, halo($C_3$-$C_6$)cycloalkoxy, halo($C_4$-$C_7$) cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, and ($C_3$-$C_6$) cycloalkythio.

In a more particular embodiment, $R^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen, cyano and nitro.

In another particular embodiment, $R^2$ is phenyl optionally substituted with one to three groups independently selected from halogen, —CN, —$NO_2$, —$NH_2$, —OH, —COOH, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, and ($C_3$-$C_6$)cycloalkythio.

In yet a more particular embodiment, $R^2$ is phenyl optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen, cyano and nitro.

In yet another more particular embodiment, $R^2$ is phenyl or fluorophenyl.

$R^3$ is selected from ($C_1$-$C_6$)alkyl, ($C_2$-$C_6$)alkenyl, ($C_2$-$C_6$)alkynyl, ($C_3$-$C_5$)cycloalkyl($C_1$-$C_4$)alkyl, ($C_1$-$C_3$)alkoxy($C_1$-$C_3$)alkoxy, or ($C_1$-$C_3$)alkoxy($C_1$-$C_3$)alkyl and is optionally substituted with up to four groups independently selected from H, —F, —CN, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl, $R^4$O—, ($R^4$)$_2$N—, $R^4$O$_2$O—, $R^4$C(=O)O—, $R^4$S, $R^4$S(=O)—, $R^4$S(=O)$_2$—, $R^4$C(=O)N$R^4$—, ($R^4$)$_2$NC(=O)—, ($R^4$)$_2$NC(=O)O—, ($R^4$)$_2$NC(=O)N$R^4$—, $R^4$OC(=O)N$R^4$—, ($R^4$)$_2$NC(=NCN)N$R^4$—, ($R^4$O)$_2$P(=O)O—, ($R^4$O)$_2$P(=O)N$R^4$—, $R^4$OS(=O)$_2$N$R^4$—, ($R^4$)$_2$NS(=O)$_2$O—, ($R^4$)$_2$NS(=O)$_2$N$R^4$—, $R^4$S(=O)$_2$N$R^4$—, $R^4$S(=O)$_2$NHC(=O)—, $R^4$S(=O)$_2$NHC(=O)O—, $R^4$S(=O)$_2$NHC(=O)N$R^4$—, $R^4$OS(=O)$_2$NHC(=O)—, $R^4$OS(=O)$_2$NHC(=O)O—, $R^4$OS(=O)$_2$NHC(=O)N$R^4$—, ($R^4$)$_2$NS(=O)$_2$NHC(=O)—, ($R^4$)$_2$NS(=O)$_2$NHC(=O)O—, ($R^4$)$_2$NS(=O)$_2$NHC(=O)N$R^4$—, $R^4$C(=O)NHS(=O)$_2$—, $R^4$C(=O)NHS(=O)$_2$O—, $R^4$C(=O)NHS(=O)$_2$N$R^4$—, $R^4$OC(=O)NHS(=O)$_2$—, $R^4$OC(=O)NHS(=O)$_2$O—, $R^4$OC(=O)NHS(=O)$_2$N$R^4$—, ($R^4$)$_2$NC(=O)NHS(=O)$_2$—, ($R^4$)$_2$NC(=O)NHS(=O)$_2$O—, ($R^4$)$_2$NC(=O)NHS(=O)$_2$N$R^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2$H, $CONH_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2$H, $CONH_2$, N-monoalkyl-substituted amido, N,N-dialkyl-substituted amido, or oxo).

In one particular embodiment, $R^3$ is ($C_3$-$C_6$)alkenyl, hydroxy($C_2$-$C_5$)alkyl, cyano($C_2$-$C_5$)alkyl, dihydroxy($C_3$-$C_5$) alkyl, ω-$H_2$NCO($C_1$-$C_5$)alkyl, ($C_1$-$C_2$)alkoxy($C_1$-$C_4$)alkyl, $H_2$NSO$_2$O($C_2$-$C_5$)alkyl, $H_2$NSO$_2$NH($C_2$-$C_5$)alkyl, oxo($C_2$-$C_5$)alkyl, MeC(=O)NH($C_2$-$C_5$)alkyl, MeSO$_2$NH($C_2$-$C_5$)alkyl, or MeSO$_2$NH($C_2$-$C_5$)alkyl.

In another particular embodiment, $R^3$ is methyl, ethyl, propyl, butyl, vinyl, allyl or ethoxyethyl each optionally substituted with up to two groups independently selected from methyl, HO—, MeO—, $H_2$N—, MeC(=O)NH—, MeS(=O)$_2$NH—, $H_2$NC(=O)—, MeNHC(=O)—, HO$_2$C—, (HO)$_2$P(=O)O—, $H_2$NS(=O)$_2$O—, $H_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, $H_2$NCH$_2$C(=O)NH—, EtNHC(=O)NH, MeOC(=O)NH—, MeNHC(=NC≡N)NH—, MeS—, MeSO$_2$-MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2$NCONH—, $H_2$NCO$_2$—, HOCH$_2$CH$_2$O—, MeNH—, Me$_2$N— and MeCONMe.

In a more particular embodiment, $R^3$ is methyl, ethyl, propyl, butyl, vinyl, allyl or ethoxyethyl each optionally substituted with up to two groups independently selected from methyl, HO—, MeO—, $H_2$N—, MeC(=O)NH—, MeS(=O)$_2$NH—, $H_2$NC(=O)—, MeNHC(=O)—, HO$_2$C—, MeNHC(=O)NH—, oxo, cyano, HOCH$_2$C(=O)NH—, EtNHC(=O)NH, MeS—, MeSO$_2$— MeSO$_2$N(Me)-, 2-oxo-1-pyrrolidinyl, $H_2$NCONH—, $H_2$NCO$_2$—, HOCH$_2$CH$_2$O—, MeNH—, Me$_2$N— and MeCONMe.

In yet a more particular embodiment, $R^3$ is 2-methylallyl, MeSO$_2$NHCH$_2$CH$_2$CH$_2$, $H_2$NC(=O)CH$_2$CH$_2$, $H_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

In an even more particular embodiment, $R^3$ is 2-methylallyl, 2-hydroxy-2-methylpropyl or 2-cyano-2-methylpropyl.

m is 1 or 2.

In a particular embodiment, m is 1.

Q is O, $CH_2$ or $NR^5$.

In a particular embodiment, Q is O.

Y is ($C_1$-$C_6$)alkyl, halo($C_1$-$C_6$)alkyl or oxo.

In a particular embodiment, Y is methyl, ethyl or fluoromethyl.

m is 1 or 2.

In a particular embodiment, m is 1.

Each $R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl.

Each $R^5$ is independently H, ($C_1$-$C_6$)alkyl, halo($C_1$-$C_6$)alkyl or hydroxy($C_1$-$C_6$)alkyl.

Each $R^6$ is independently ($C_1$-$C_6$)alkyl, ($C_2$-$C_6$)alkenyl, ($C_2$-$C_6$)alkynyl or ($C_1$-$C_6$)alkoxy.

$V^1$ is ($C_1$-$C_6$)alkylene, ($C_1$-$C_6$)alkenylene, ($C_1$-$C_6$)alkynylene or ($C_1$-$C_6$)alkyleneoxy.

Each $R^7$ is independently ($C_3$-$C_6$)cycloalkyl or ($C_3$-$C_6$)cycloalkoxy;

$R^8$ is heterocyclyl.

$R^9$ is ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo(C₁-C₆)alkoxy(C₁-C₆)alkoxy, (C₁-C₆)alkoxy(C₁-C₆)alkyl or halo(C₁-C₆)alkoxy(C₁-C₆)alkyl.

In a 1$^{st}$ specific embodiment, the compound of the present invention is represented by Structural Formula

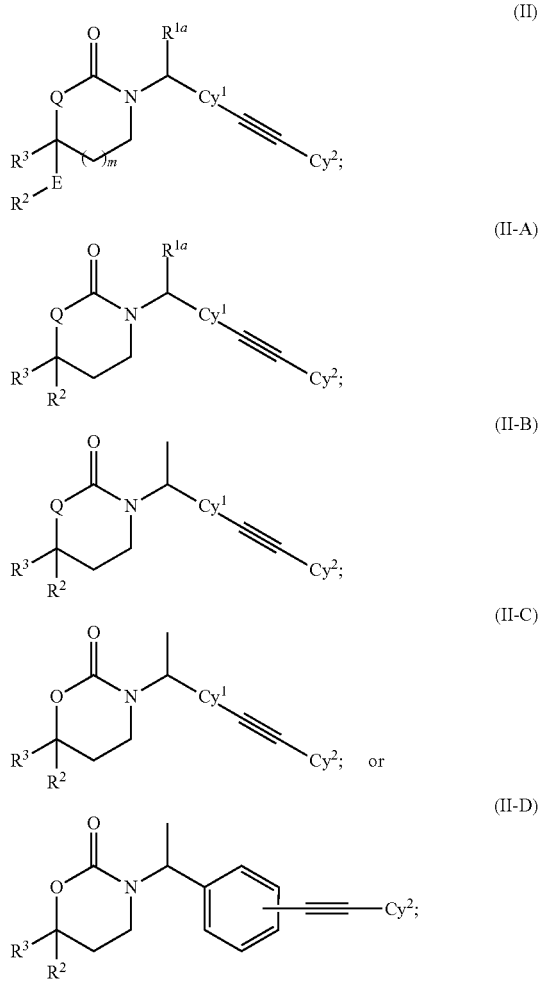

or a pharmaceutically acceptable salt, enantiomer or diastereomer thereof. Values for the variables in Structural Formula (II)-(II-D) are as described above for Structural Formula (I).

In a 1$^{st}$ more specific embodiment, for compounds of Structural Formula (II)-(II-D), R$^{1a}$, if present, is an optionally substituted (C₁-C₆)alkyl, preferably, methyl or ethyl, Cy$^1$, if present, is an optionally substituted cyclohexyl, phenyl, pyridyl, pyrimidinyl, thiazolyl, triazolyl or benzothiazolyl group, and values and particular values for the remainder of the variables in Structural Formula (II)-(II-D) are as described above for Structural Formula (I).

In a 2$^{nd}$ more specific embodiment, for compounds of Structural Formula (II)-(II-D), Q, if present, is O, CH₂ or NH, R$^{1a}$, if present, is an optionally substituted methyl or ethyl group, Cy$^1$, if present, is an optionally substituted cyclohexyl, phenyl, pyridyl, pyrimidinyl, thiazolyl, triazolyl or benzothiazolyl group, and values and particular values for the remainder of the variables in Structural Formula (II)-(II-D) are as described above for Structural Formula (I).

In a 3$^{rd}$ more specific embodiment, for compounds of Structural Formula (II)-(II-D), Q, if present, is O, CH₂ or NH, R$^{1a}$, if present, is an optionally substituted methyl or ethyl group, Cy$^1$, if present, is an optionally substituted cyclohexyl, phenyl, pyridyl, pyrimidinyl, thiazolyl, triazolyl or benzothiazolyl group, preferably, an optionally substituted phenyl group, Cy$^1$ is an optionally substituted methyl, ethyl, propyl, butyl, pentyl, hexyl, cyclopropyl, cyclobutyl, cyclopentyl, cyclohexyl, phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, or 1,1-dioxo-hexahydro-1,2-thiazinyl group, and values and particular values for the remainder of the variables in Structural Formula (II)-(II-D) are as described above for Structural Formula (I).

In a 4$^{th}$ more specific embodiment, for compounds of Structural Formula (II)-(II-D), Q, if present, is O, CH₂ or NH, R$^{1a}$, if present, is an optionally substituted methyl or ethyl group, Cy$^1$, if present, is optionally substituted phenyl, Cy$^2$ is an optionally substituted methyl, ethyl, propyl, butyl, pentyl, hexyl, cyclopropyl, cyclobutyl, cyclopentyl, cyclohexyl, phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, or 1,1-dioxo-hexahydro-1,2-thiazinyl group. Alternatively, Cy$^2$ is an optionally substituted methyl, ethyl, cyclopentyl, cyclohexyl, phenyl, pyridyl, oxodihydropyridyl, piperidinyl, azetidinyl or tetrahydropyranyl group. Examplary substituents for the group represented by Cy$^2$ are —NH₂, —OH, —COOH, —COOR$^6$, —R$^6$, —C(=O)NHR$^7$; —C(=O)NR$^6$R$^6$, —C(=O)R$^8$, —NHC(=O)R$^6$, —NHC(=O)R$^7$, —NHC(=O)NH₂, —NHC(=O)NHR$^6$, —NHC(=O)NR$^6$R$^6$, oxooxazolidinyl, —OC(=O)OR$^6$, and —NHS(=O)₂R$^6$. An alternative list of examplary substituents for the group represented by Cy$^2$ is —NH₂, —OH, —COOH, —COOMe, —OMe, cyclopropylcarbamoyl; —C(=O)NMe₂, azetidinylcarbonyl, —NHC(=O)Me, —NHC(=O)OMe, cyclopropanecarboxamido, —NHC(=O)NH₂, —NHC(=O)NHMe, —NHC(=O)NMe₂, oxooxazolidinyl, —OC(=O)OMe, and —NHS(=O)₂Me. Values and particular values for the remainder of the variables in Structural Formula (II)-(II-D) are as described above for Structural Formula (I).

In a 5$^{th}$ more specific embodiment, for compounds of Structural Formula (II)-(II-D), the variables are as defined in the previous paragraph and the phenyl group represented by Cy$^1$ is optionally substituted with one to three groups selected from fluoro, chloro, cyano, CONH₂, CONHMe, CONMe₂, CONHc-Pr, methyl, ethyl, cyclopropyl, CF₃ and oxo.

In a 6$^{th}$ more specific embodiment, for compounds of Structural Formula (II)-(II-D), Cy$^1$, if present, is optionally substituted phenyl, Cy² is an optionally substituted methyl, ethyl, cyclopentyl, cyclohexyl, phenyl, pyridyl, oxodihydropyridyl, piperidinyl, azetidinyl or tetrahydropyranyl group, the group represented by Cy² is optionally substituted with one to three groups independently selected from —NH₂, —OH, —COOH, —COOMe, —OMe, cyclopropylcarbamoyl; —C(═O)NMe₂, azetidinylcarbonyl, —NHC(═O)Me, —NHC(═O)OMe, cyclopropanecarboxamido, —NHC(═O)NH₂, —NHC(═O)NHMe, —NHC(═O)NMe₂, oxooxazolidinyl, —OC(═O)OMe, and —NHS(═O)₂Me, and values and specific values for the remainder of the variables in Structural Formula (II)-(II-D) are as described above for Structural Formula (I).

Another specific embodiment of the present invention is a compound of Structural Formula (I), (II), (II-A), (II-B), (II-C) or (II-D), or a pharmaceutically acceptable salt, enantiomer or diastereomer thereof, R¹ᵃ and R¹ᵇ, if present, are independently optionally substituted with up to four groups independently selected from fluorine, cyano, oxo, (C₁-C₆)alkyl, halo(C₁-C₆)alkyl, amino(C₁-C₆)alkyl, (C₁-C₆)alkylamino(C₁-C₆)alkyl, di(C₁-C₆)alkylamino(C₁-C₆)alkyl, hydroxy(C₁-C₆)alkyl and (C₁-C₆)alkoxy(C₁-C₆)alkyl, R⁴O—, (R⁴)₂N—, R⁴O₂C—, R⁴S, R⁴S(═O)—, R⁴S(═O)₂—, R⁴C(═O)NR⁴—, (R⁴)₂NC(═O)—, (R⁴)₂NC(═O)O—, (R⁴)₂NC(═O)NR⁴—, R⁴OC(═O)NR⁴—, (R⁴)₂NS(═O)₂NR⁴— and R⁴S(═O)₂NR⁴—; R³ is (C₃-C₆)alkenyl, hydroxy(C₂-C₅)alkyl, cyano(C₂-C₅)alkyl, dihydroxy(C₃-C₅)alkyl, ω-H₂NCO(C₁-C₅)alkyl, (C₁-C₂)alkoxy(C₁-C₄)alkyl, H₂NSO₂O(C₂-C₅)alkyl, H₂NSO₂NH(C₂-C₅)alkyl, oxo(C₂-C₅)alkyl, MeC(═O)NH(C₂-C₅)alkyl, MeSO₂NH(C₂-C₅)alkyl, or MeSO₂NH(C₂-C₅)alkyl. Alternatively, R³ is methyl, ethyl, propyl, butyl, vinyl, allyl or ethoxyethyl each optionally substituted with up to two groups independently selected from methyl, HO—, MeO—, H₂N—, MeC(═O)NH—, MeS(═O)₂NH—, H₂NC(═O)—, MeNHC(═O)—, HO₂C—, (HO)₂P(═O)O—, H₂NS(═O)₂O—, H₂NS(═O)₂NH—, MeNHC(═O)NH—, MeNHC(═O)O—, oxo, cyano, HO₂C—, HOCH₂CH₂NH—, 4-morpholino, HOCH₂C(═O)NH—, H₂NCH₂C(═O)NH—, EtNHC(═O)NH, MeOC(═O)NH—, MeNHC(═NC═N)NH—, MeS—, MeSO₂-MeSO₂N(Me)-, MeS(═O)₂NHC(═O)—, imidazolylamino-, imidazolyl, tetrazolyl, spirocyclopropyl, FCH₂CH₂NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H₂NCONH—, H₂NCO₂—, HOCH₂CH₂O—, MeNH—, Me₂N— and MeCONMe. Values and particular or specific values for the remainder of the variables are as described in Structural Formula (I), (II), (II-A), (II-B), (II-C) or (II-D) or the 1ˢᵗ, 2ⁿᵈ, 3ʳᵈ, 4ᵗʰ, 5ᵗʰ or 6ᵗʰ more specific embodiment thereunder.

Another embodiment of the present invention is a compound of Structural Formula (I), (II), (II-A), (II-B), (II-C) or (II-D), or a pharmaceutically acceptable salt, enantiomer or diastereomer thereof, R¹ᵃ and R¹ᵇ, if present, are independently optionally substituted with up to four groups independently selected from fluorine, cyano, oxo, (C₁-C₆)alkyl, halo(C₁-C₆)alkyl, amino(C₁-C₆)alkyl, (C₁-C₆)alkylamino(C₁-C₆)alkyl, di(C₁-C₆)alkylamino(C₁-C₆)alkyl, hydroxy(C₁-C₆)alkyl and (C₁-C₆)alkoxy(C₁-C₆)alkyl, R⁴O—, (R⁴)₂N—, R⁴O₂C—, R⁴S, R⁴S(═O)—, R⁴S(═O)₂—, R⁴C(═O)NR⁴—, (R⁴)₂NC(═O)—, (R⁴)₂NC(═O)O—, (R⁴)₂NC(═O)NR⁴—, R⁴OC(═O)NR⁴—, (R⁴)₂NS(═O)₂NR⁴— and R⁴S(═O)₂NR⁴—; R² is an optionally substituted (C₁-C₆)alkyl, aryl, heteroaryl or cycloalkyl group; E, if present, is a bond or CH₂, and R³ is methyl, ethyl, propyl, butyl, vinyl, allyl or ethoxyethyl each optionally substituted with up to two groups independently selected from methyl, HO—, MeO—, H₂N—, MeC(═O)NH—, MeS(═O)₂NH—, H₂NC(═O)—, MeNHC(═O)—, HO₂C—, (HO)₂P(═O)O—, H₂NS(═O)₂O—, H₂NS(═O)₂NH—, MeNHC(═O)NH—, MeNHC(═O)O—, oxo, cyano, HO₂C—, HOCH₂CH₂NH—, 4-morpholino, HOCH₂C(═O)NH—, H₂NCH₂C(═O)NH—, EtNHC(═O)NH, MeOC(═O)NH—, MeNHC(═NC═N)NH—, MeS—, MeSO₂— MeSO₂N(Me)-, MeS(═O)₂NHC(═O)—, imidazolylamino-, imidazolyl, tetrazolyl, spirocyclopropyl, FCH₂CH₂NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H₂NCONH—, H₂NCO₂—, HOCH₂CH₂O—, MeNH—, Me₂N— and MeCONMe. Alternatively, R³ is (C₃-C₆)alkenyl, hydroxy(C₂-C₅)alkyl, cyano(C₂-C₅)alkyl, dihydroxy(C₃-C₅)alkyl, ω-H₂NCO(C₁-C₅)alkyl, (C₁-C₂)alkoxy(C₁-C₄)alkyl, H₂NSO₂O(C₂-C₅)alkyl, H₂NSO₂NH(C₂-C₅)alkyl, oxo(C₂-C₅)alkyl, MeC(═O)NH(C₂-C₅)alkyl, MeSO₂NH(C₂-C₅)alkyl, or MeSO₂NH(C₂-C₅)alkyl. Values and particular or specific values for the remainder of the variables are as described in Structural Formula (I), (II), (II-A), (II-B), (II-C) or (II-D) or the 1ˢᵗ, 2ⁿᵈ, 3ʳᵈ, 4ᵗʰ, 5ᵗʰ, or 6ᵗʰ more specific embodiment thereunder.

Another embodiment of the present invention is a compound of Structural Formula (I), (II), (II-A), (II-B), (II-C) or (II-D), or a pharmaceutically acceptable salt, enantiomer or diastereomer thereof, R² is phenyl, fluorophenyl, isopropyl, cyclopropyl, t-butyl, cyclopropylmethyl or trifluoroethyl; R³ is 2-methylallyl, 2-hydroxy-2-methylpropyl or 2-cyano-2-methylpropyl; the group represented by Cy¹ is optionally substituted with fluoro, chloro, cyano, CONH₂, CONHMe, CONMe₂, CONHc-Pr, methyl, ethyl, cyclopropyl, CF₃ or oxo; and the group represented by Cy¹ is optionally substituted with one to three groups independently selected from —NH₂, —OH, —COOH, —COOMe, —OMe, cyclopropylcarbamoyl; —C(═O)NMe₂, azetidinylcarbonyl, —NHC(═O)Me, —NHC(═O)OMe, cyclopropanecarboxamido, —NHC(═O)NH₂, —NHC(═O)NHMe, —NHC(═O)NMe₂, oxooxazolidinyl, —OC(═O)OMe, and —NHS(═O)₂Me, and values and particular or specific values for the remainder of the variables are described in Structural Formula (I), (II), (II-A), (II-B), (II-C) or (II-D) or the 1ˢᵗ, 2ⁿᵈ, 3ʳᵈ, 4ᵗʰ, 5ᵗʰ or 6ᵗʰ more specific embodiment thereunder.

In a 2ⁿᵈ specific embodiment, the compound of the present invention is represented by Structural Formula

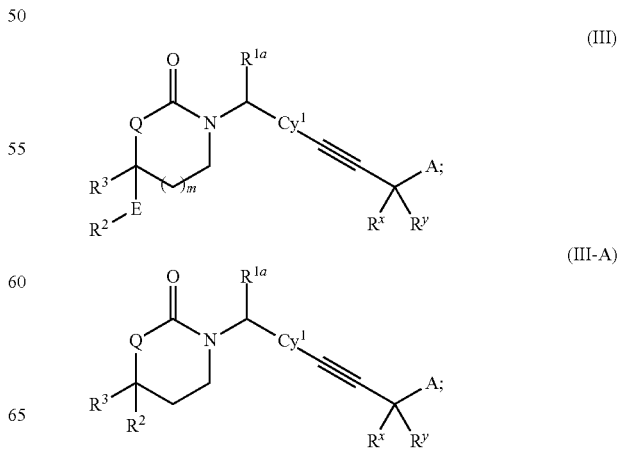

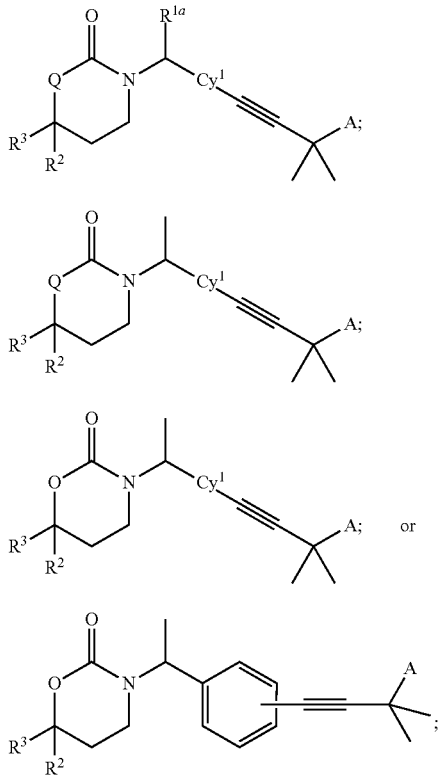

or a pharmaceutically acceptable salt, enantiomer or diastereomer thereof. $R^x$ and $R^y$, if present, are, independently, optionally substituted $(C_1-C_6)$alkyl, preferably, methyl or ethyl; A is selected from —CN, —NO$_2$, —NH$_2$, —OH, —COOH, —COOR$^6$, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NHR$^7$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R)$_2$, —S(=O)$_2$NHR$^7$, —S(=O)$_2$NR$^6$R$^7$, —S(=O)$_2$N(R$^7$)$_2$, cyano$(C_1-C_6)$alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$, and values and particular values for the remainder of the variables in Structural Formula (III)-(III-E) are as described above for Structural Formula (I).

In a 1$^{st}$ more specific embodiment for compounds of Structural Formula (III)-(III-E), Cy$^1$, if present, is an optionally substituted cyclohexyl, phenyl, pyridyl, pyrimidinyl, thiazolyl, triazolyl or benzothiazolyl group, preferably, an optionally substituted phenyl group; R$^{1a}$, if present, is optionally substituted methyl or ethyl; and values and specific values for the remainder of the variables in Structural Formula (III)-(III-E) are as described above for Structural Formula (I).

In a 2$^{nd}$ more specific embodiment for compounds of Structural Formula (III-A), Q, if present, is O, CH$_2$ or NH, preferably, O; Cy$^1$, if present, is an optionally substituted cyclohexyl, phenyl, pyridyl, pyrimidinyl, thiazolyl, triazolyl or benzothiazolyl group, preferably, an optionally substituted phenyl group; R$^{1a}$ is optionally substituted methyl or ethyl, R$^x$ and R$^y$, if present, are, independently, optionally substituted $(C_1-C_6)$alkyl, preferably, methyl or ethyl; A is selected from —CN, —NO$_2$, —NH$_2$, —OH, —COOH, —COOR$^6$, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NHR$^7$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano$(C_1-C_6)$alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$, and values and specific values for the remainder of the variables in Structural Formula (III)-(III-E) are as described above for Structural Formula (I).

In a 3$^{rd}$ more specific embodiment for compounds of Structural Formula (III)-(III-E), Cy$^1$, if present, is an optionally substituted cyclohexyl, phenyl, pyridyl, pyrimidinyl, thiazolyl, triazolyl or benzothiazolyl group; A is selected from —NH$_2$, —OH, —COOH, —COOR$^6$, —R$^6$, —C(=O)NHR$^7$; —C(=O)NR$^6$R$^6$, —C(=O)R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, and —NHS(=O)$_2$R$^6$. Preferably, A is selected from —NH$_2$, —OH, —COOH, —COO$(C_1-C_6)$alkyl, $(C_1-C_6)$alkoxy, —C(=O)NH$(C_3-C_6)$cycloalkyl; —C(=O)N{$(C_1-C_6)$alkyl}{$(C_1-C_6)$alkyl}, azetidinylcarbonyl, —NHC(=O)$(C_1-C_6)$alkyl, —NHC(=O)O$(C_1-C_6)$alkyl, —NHC(=O)$(C_3-C_6)$cycloalkyl, —NHC(=O)NH$_2$, —NHC(=O)NH$(C_1-C_6)$alkyl, —NHC(=O)N{$(C_1-C_6)$alkyl}{$(C_1-C_6)$alkyl}, oxooxazolidinyl, —OC(=O)O$(C_1-C_6)$alkyl, and —NHS(=O)$_2$$(C_1-C_6)$alkyl. Values and specific values for the remainder of the variables in Structural Formula (III)-(III-E) are as described above for Structural Formula (I). For the embodiment described in this paragraph, Cy$^1$, if present, is preferably optionally substituted phenyl.

Another embodiment of the present invention is a compound of Structural Formula (III), (III-A), (III-B), (III-C), (III-D) or (III-E), or a pharmaceutically acceptable salt, enantiomer or diastereomer thereof, $R^{1a}$, if present, is optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O$—, $(R^4)_2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—; $R^3$ is $(C_3-C_6)$alkenyl, hydroxy$(C_2-C_5)$alkyl, cyano$(C_2-C_5)$alkyl, dihydroxy$(C_3-C_5)$alkyl, ω-$H_2$NCO$(C_1-C_6)$alkyl, $(C_1-C_2)$alkoxy$(C_1-C_4)$alkyl, $H_2NSO_2O(C_2-C_6)$alkyl, $H_2NSO_2NH(C_2-C_6)$alkyl, oxo$(C_2-C_5)$alkyl, MeC(=O)NH$(C_2-C_5)$alkyl, MeSO$_2$NH$(C_2-C_6)$alkyl, or MeSO$_2$NH$(C_2-C_6)$alkyl. Alternatively, $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, HO$_2$C—, (HO)$_2$P(=O)O—, $H_2$NS(=O)$_2$O—, $H_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, $H_2$NCH$_2$C(=O)NH—, EtNHC(=O)NH, MeOC(=O)NH—, MeNHC(=NC≡N)NH—, MeS—, MeSO$_2$—, MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2$NCONH—, $H_2$NCO$_2$—, HOCH$_2$CH$_2$O—, MeNH—, Me$_2$N— and MeCONMe. Values and particular or specific values for the remainder of the variables are described in Structural Formula (I), (III), (III-A), (III-B), (III-C), (III-D) or (III-E) or the 1$^{st}$, 2$^{nd}$ or 3$^{rd}$ more specific embodiment thereunder.

Another embodiment of the present invention is a compound of Structural Formula (III), (III-A), (III-B), (III-C), (III-D) or (III-E), or a pharmaceutically acceptable salt, enantiomer or diastereomer thereof, $R^2$ is an optionally substituted $(C_1-C_6)$alkyl, aryl, heteroaryl or cycloalkyl group, E, if present, is a bond or CH$_2$, and $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, HO$_2$C—, (HO)$_2$P(=O)O—, $H_2$NS(=O)$_2$O—, $H_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, $H_2$NCH$_2$C(=O)NH—, EtNHC(=O)NH, MeOC(=O)NH—, MeNHC(=NC≡N)NH—, MeS—, MeSO$_2$—, MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2$NCONH—, $H_2$NCO$_2$—, HOCH$_2$CH$_2$O—, MeNH—, Me$_2$N— and MeCONMe, and values and particular or specific values for the remainder of the variables in Structural Formula (I), (III), (III-A), (III-B), (III-C), (III-D) or (III-E), respectively, are as described above for Structural Formula (III).

Another embodiment of the present invention is a compound of Structural Formula (III), (III-A), (III-B), (III-C), (III-D) or (III-E), or a pharmaceutically acceptable salt, enantiomer or diastereomer thereof, $R^{1a}$, if present, is optionally substituted with up to four groups independently selected from fluorine, cyano, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, $(C_1-C_6)$alkoxy$(C_1-C_6)$alkyl, $R^4O$—, $(R^4)2N$—, $R^4O_2C$—, $R^4S$, $R^4S(=O)$—, $R^4S(=O)_2$—, $R^4C(=O)NR^4$—, $(R^4)_2NC(=O)$—, $(R^4)_2NC(=O)O$—, $(R^4)_2NC(=O)NR^4$—, $R^4OC(=O)NR^4$—, $(R^4)_2NS(=O)_2NR^4$— and $R^4S(=O)_2NR^4$—; $R^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen, cyano and nitro; $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2$NH—, $H_2$NC(=O)—, MeNHC(=O)—, HO$_2$C—, (HO)$_2$P(=O)O—, $H_2$NS(=O)$_2$O—, $H_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, $H_2$NCH$_2$C(=O)NH—, EtNHC(=O)NH, MeOC(=O)NH—, MeNHC(=NC≡N)NH—, MeS—, MeSO$_2$—, MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2$NCONH—, $H_2$NCO$_2$—, HOCH$_2$CH$_2$O—, MeNH—, Me$_2$N— and MeCONMe, and values and particular or specific values for the remainder of the variables are described in Structural Formula (I), (III), (III-A), (III-B), (III-C), (III-D) or (III-E), or the 1$^{st}$, 2$^{nd}$ or 3$^{rd}$ more specific embodiment thereunder.

Another embodiment of the present invention is a compound of Structural Formula (III), (III-A), (III-B), (III-C), (III-D) or (III-E), or a pharmaceutically acceptable salt, enantiomer or diastereomer thereof, $R^2$ is phenyl, fluorophenyl, isopropyl, cyclopropyl, t-butyl, cyclopropylmethyl or trifluoroethyl; $R^3$ is 2-methylallyl, 2-hydroxy-2-methylpropyl or 2-cyano-2-methylpropyl; the group represented by Cy$^1$ is optionally substituted with fluoro, chloro, cyano, CONH$_2$, CONHMe, CONMe$_2$, CONHc-Pr, methyl, ethyl, cyclopropyl, CF$_3$ or oxo; and A is selected from —NH$_2$, —OH, —COOH, —C(=O)NH$(C_3-C_6)$cycloalkyl; —C(=O)N{$(C_1-C_6)$alkyl}{$(C_1-C_6)$alkyl}, azetidinylcarbonyl, —NHC(=O)$(C_1-C_6)$alkyl, —NHC(=O)O$(C_1-C_6)$alkyl, —NHC(=O)$(C_3-C_6)$cycloalkyl, —NHC(=O)NH$_2$, —NHC(=O)NH$(C_1-C_6)$alkyl, —NHC(=O)N{$(C_1-C_6)$alkyl}{$(C_1-C_6)$alkyl}, oxooxazolidinyl, and —NHS(=O)$_2$$(C_1-C_6)$alkyl, and values and particular or specific values for the remainder of the variables are described in Structural Formula (I), (III), (III-A), (III-B), (III-C), (III-D) or (III-E), or the 1$^{st}$, 2$^{nd}$ or 3$^{rd}$ more specific embodiment thereunder.

In a 3$^{rd}$ specific embodiment, the compound of the present invention is represented by Structural Formula

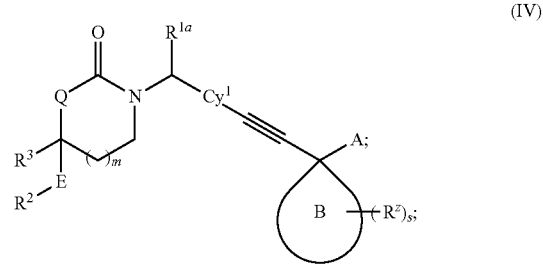

(IV)

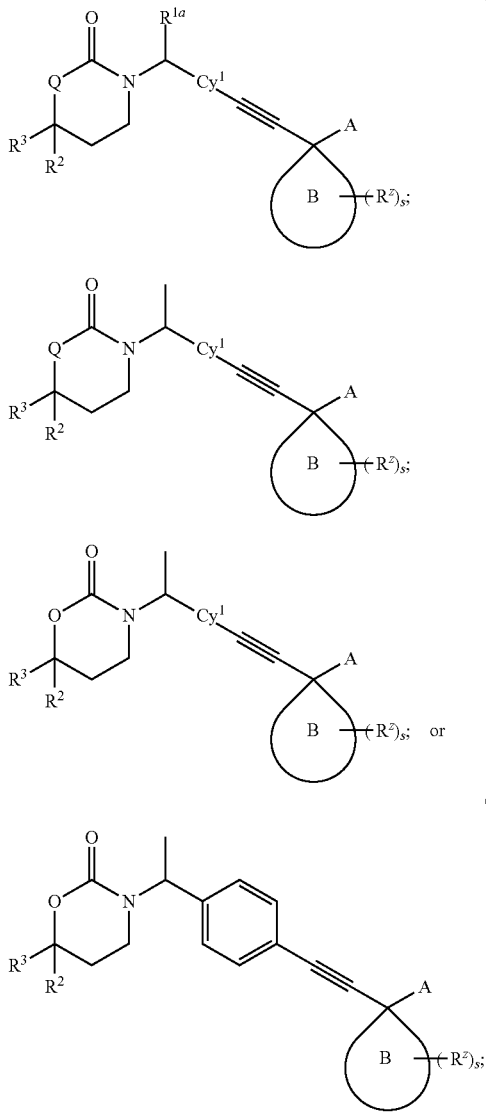

or a pharmaceutically acceptable salt, enantiomer or diastereomer thereof. B is cycloalkyl or heterocyclyl, s is 0, 1, 2 or 3, each $R^z$ is independently selected from —CN, —NO$_2$, —NH$_2$, —OH, —COOH, —COOR$^6$, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl, hydroxy(C$_1$-C$_6$)alkoxy, (C$_4$-C$_7$)cycloalkylalkyl, (C$_4$-C$_7$)cycloalkylalkoxy, (C$_3$-C$_6$)cycloalkyl(C$_2$-C$_4$)alkynyl, halo(C$_1$-C$_6$)alkyl, halo(C$_2$-C$_6$)alkenyl, halo(C$_3$-C$_6$)cycloalkyl, halo(C$_4$-C$_7$)cycloalkylalkyl, halo(C$_1$-C$_6$)alkoxy, halo(C$_3$-C$_6$)cycloalkoxy, halo(C$_4$-C$_7$)cycloalkylalkoxy, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, (C$_1$-C$_6$)alkylthio, (C$_3$-C$_6$)cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NHR$^7$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$; A is selected from —CN, —NO$_2$, —NH$_2$, —OH, —COOH, —COOR$^6$, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl, hydroxy(C$_1$-C$_6$)alkoxy, (C$_4$-C$_7$)cycloalkylalkyl, (C$_4$-C$_7$)cycloalkylalkoxy, (C$_3$-C$_6$)cycloalkyl(C$_2$-C$_4$)alkynyl, halo(C$_1$-C$_6$)alkyl, halo(C$_2$-C$_6$)alkenyl, halo(C$_3$-C$_6$)cycloalkyl, halo(C$_4$-C$_7$)cycloalkylalkyl, halo(C$_1$-C$_6$)alkoxy, halo(C$_3$-C$_6$)cycloalkoxy, halo(C$_4$-C$_7$)cycloalkylalkoxy, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxy(C$_1$-C$_6$)alkyl, halo(C$_1$-C$_6$)alkoxy(C$_1$-C$_6$)alkyl, (C$_1$-C$_6$)alkylthio, (C$_3$-C$_6$)cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NHR$^7$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$, and values and particular values for the remainder of the variables in Structural Formula (IV)-(IV-D) are as described above for Structural Formula (I).

In a 1$^{st}$ more specific embodiment for compounds of Structural Formula (IV)-(IV-D), Cy$^1$, if present, is an optionally substituted cyclohexyl, phenyl, pyridyl, pyrimidinyl, thiazolyl, triazolyl or benzothiazolyl group, preferably an optionally substituted phenyl group, R$^{1a}$, if present, is optionally substituted methyl or ethyl, and values and specific values for the remainder of the variables in Structural Formula (IV)-(IV-D) are as described above for Structural Formula (I).

In a 2$^{nd}$ more specific embodiment for compounds of Structural Formula (IV)-(IV-D), Q, if present, is O, CH$_2$ or NH, preferably Q is O; Cy$^1$, if present, is an optionally substituted cyclohexyl, phenyl, pyridyl, pyrimidinyl, thiazolyl, triazolyl or benzothiazolyl group, preferably an optionally substituted phenyl group, R$^{1a}$, if present, is optionally substituted methyl or ethyl, and values and specific values for the remainder of the variables in Structural Formula (IV)-(IV-D) are as described above for Structural Formula (I).

In 3$^{rd}$ more specific embodiment for compounds of Structural Formula (IV)-(IV-D), Cy$^1$, if present, is an optionally substituted cyclohexyl, phenyl, pyridyl, pyrimidinyl, thiazolyl, triazolyl or benzothiazolyl group, preferably an optionally substituted phenyl group; B is an optionally substituted cyclobutyl, cyclopentyl, cyclohexyl, piperidinyl, pyrrolidinyl, azetidinyl, morpholinyl, tetrahydropyranyl, dihydropyranyl, tetrahydrofuranyl or oxetanyl group, and values and specific values for the remainder of the variables in Structural Formula (IV)-(IV-D) are as described above for Structural Formula (I).

In a 4th more specific embodiment for compounds of Structural Formula (IV)-(IV-D), $Cy^1$, if present, is an optionally substituted cyclohexyl, phenyl, pyridyl, pyrimidinyl, thiazolyl, triazolyl or benzothiazolyl group, preferably an optionally substituted phenyl group; B is an optionally substituted cyclobutyl, cyclopentyl, cyclohexyl, piperidinyl, pyrrolidinyl, azetidinyl, morpholinyl, tetrahydropyranyl, dihydropyranyl, tetrahydrofuranyl or oxetanyl group, $R^{1a}$, if present, is optionally substituted methyl or ethyl, A is selected from —$NH_2$, —OH, —COOH, —$COOR^6$, —$R^6$, —C(=O)$NHR^7$; —C(=O)$NR^6R^6$, —C(=O)$R^8$, —NHC(=O)$R^6$, —NHC(=O)$R^7$, —NHC(=O)$NH_2$, —NHC(=O)$NHR^6$, —NHC(=O)$NR^6R^6$, oxooxazolidinyl, —OC(=O)$OR^6$, and —NHS(=O)$_2R^6$, and values and specific values for the remainder of the variables in Structural Formula (IV)-(IV-D) are as described above for Structural Formula (I).

Another embodiment of the present invention is a compound of Structural Formula (IV), (IV-A), (IV-B), (IV-C) or (IV-D), or a pharmaceutically acceptable salt, enantiomer or diastereomer thereof, $R^{1a}$, if present, is optionally substituted methyl or ethyl. Exemplary substituents for the group represented by $R^{1a}$ are fluorine, cyano, oxo, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl, ($C_1$-$C_6$)alkoxy($C_1$-$C_6$)alkyl, $R^4O$—, $(R^4)_2N$—, $R^4O_2C$—, $R^4S$, $R^4S$(=O)—, $R^4S$(=O)$_2$—, $R^4C$(=O)$NR^4$—, $(R^4)_2NC$(=O)—, $(R^4)_2NC$(=O)O—, $(R^4)_2NC$(=O)$NR^4$—, $R^4OC$(=O)$NR^4$—, $(R^4)_2NS$(=O)$_2NR^4$— and $R^4S$(=O)$_2NR^4$—; $R^3$ is ($C_3$-$C_6$)alkenyl, hydroxy($C_2$-$C_5$)alkyl, cyano($C_2$-$C_5$)alkyl, dihydroxy($C_3$-$C_5$)alkyl, ω-$H_2NCO$($C_1$-$C_5$)alkyl, ($C_1$-$C_2$)alkoxy($C_1$-$C_4$)alkyl, $H_2NSO_2O$($C_2$-$C_5$)alkyl, $H_2NSO_2NH$($C_2$-$C_5$)alkyl, oxo($C_2$-$C_5$)alkyl, MeC(=O)NH($C_2$-$C_5$)alkyl, $MeSO_2NH$($C_2$-$C_5$)alkyl, or $MeSO_2NH$($C_2$-$C_5$)alkyl. Alternatively, $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2NH$—, $H_2NC$(=O)—, MeNHC(=O)—, $HO_2C$—, $(HO)_2P$(=O)O—, $H_2NS$(=O)$_2O$—, $H_2NS$(=O)$_2NH$—, MeNHC(=O)NH—, MeNHC(=O)O—, oxo, cyano, $HO_2C$—, $HOCH_2CH_2NH$—, 4-morpholino, $HOCH_2C$(=O)NH—, $H_2NCH_2C$(=O)NH—, EtNHC(=O)NH, MeOC(=O)NH—, MeNHC(=NC≡N)NH—, MeS—, $MeSO_2$— $MeSO_2N$(Me)-, MeS(=O)$_2NHC$(=O)—, imidazolylamino-, imidazolyl, tetrazolyl, spirocyclopropyl, $FCH_2CH_2NH$, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2NCONH$—, $H_2NCO_2$—, $HOCH_2CH_2O$—, MeNH—, $Me_2N$— and MeCONMe. Values and particular or specific values for the remainder of the variables are described in Structural Formula (I), (IV), (IV-A), (IV-B), (IV-C) or (IV-D), or the 1st, 2nd, 3rd or 4th more specific embodiment thereunder.

Another embodiment of the present invention is a compound of Structural Formula (IV), (IV-A), (IV-B), (IV-C) or (IV-D), or a pharmaceutically acceptable salt, enantiomer or diastereomer thereof, $R^2$ is an optionally substituted ($C_1$-$C_6$) alkyl, aryl, heteroaryl or cycloalkyl group, E, if present, is a bond or $CH_2$. Preferably, $R^2$ is phenyl, fluorophenyl, isopropyl, cyclopropyl, t-butyl or trifluoroethyl, or E-$R^2$ is cyclopropylmethyl, and the group represented by $R^2$ or E-$R^2$ is optionally substituted with one to three groups independently selected from ($C_1$-$C_4$)alkyl, ($C_1$-$C_4$)alkoxy, ($C_1$-$C_4$)haloalkyl, ($C_1$-$C_4$)haloalkoxy, halogen, cyano and nitro. $R^3$ is methyl, ethyl, propyl, butyl, vinyl, allyl or ethoxyethyl each optionally substituted with up to two groups independently selected from methyl, HO—, MeO—, $H_2N$—, MeC(=O)NH—, MeS(=O)$_2NH$—, $H_2NC$(=O)—, MeNHC(=O)—, $HO_2C$—, $(HO)_2P$(=O)O—, $H_2NS$(=O)$_2O$—, $H_2NS$(=O)$_2NH$—, MeNHC(=O)NH—, MeNHC(=O)O—, oxo, cyano, $HO_2C$—, $HOCH_2CH_2NH$—, 4-morpholino, $HOCH_2C$(=O)NH—, $H_2NCH_2C$(=O)NH—, EtNHC(=O)NH, MeOC(=O)NH—, MeNHC(=NC≡N)NH—, MeS—, $MeSO_2$— $MeSO_2N$(Me)-, MeS(=O)$_2NHC$(=O)—, imidazolylamino-, imidazolyl, tetrazolyl, spirocyclopropyl, $FCH_2CH_2NH$, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, $H_2NCONH$—, $H_2NCO_2$—, $HOCH_2CH_2O$—, MeNH—, $Me_2N$— and MeCONMe. Values and particular or specific values for the remainder of the variables are described in Structural Formula (I), (IV), (IV-A), (IV-B), (IV-C) or (IV-D), or the 1st, 2nd, 3rd or 4th more specific embodiment thereunder.

Another embodiment of the present invention is a compound of Structural Formula (IV), (IV-A), (IV-B), (IV-C) or (IV-D), or a pharmaceutically acceptable salt, enantiomer or diastereomer thereof, $R^2$ is optionally substituted phenyl (preferably, unsubstituted phenyl), fluorophenyl, isopropyl, cyclopropyl, t-butyl, cyclopropylmethyl or trifluoroethyl; $R^3$ is 2-methylallyl, 2-hydroxy-2-methylpropyl or 2-cyano-2-methylpropyl; the group represented by $Cy^1$, if present, is optionally substituted with fluoro, chloro, cyano, $CONH_2$, CONHMe, $CONMe_2$, CONHc-Pr, methyl, ethyl, cyclopropyl, $CF_3$ or oxo; each $R^z$ is independently selected from —$COOR^6$, ($C_1$-$C_6$)alkyl, and —C(=O)$R^6$; A is selected from —$NH_2$, —OH, —COOH, —C(=O)NH($C_3$-$C_6$)cycloalkyl; —C(=O)N{($C_1$-$C_6$)alkyl}{($C_1$-$C_6$)alkyl}, azetidinylcarbonyl, —NHC(=O)($C_1$-$C_6$)alkyl, —NHC(=O)O($C_1$-$C_6$)alkyl, —NHC(=O)($C_3$-$C_6$)cycloalkyl, —NHC(=O)$NH_2$, —NHC(=O)NH($C_1$-$C_6$)alkyl, —NHC(=O)N{($C_1$-$C_6$)alkyl}{($C_1$-$C_6$)alkyl}, oxooxazolidinyl, and —NHS(=O)$_2$($C_1$-$C_6$)alkyl; and B is an cyclopentyl, cyclohexyl, piperidinyl, azetidinyl or tetrahydropyranyl group; each $R^z$ is independently selected from —COO($C_1$-$C_6$)alkyl, ($C_1$-$C_6$) alkyl, and —OC(=O)O($C_1$-$C_6$)alkyl. Values and particular or specific values for the remainder of the variables are described in Structural Formula (IV), (IV-A), (IV-B), (IV-C) or (IV-D), or the 1st, 2nd, 3rd or 4th more specific embodiment thereunder.

In a 4th specific embodiment, the compound of the present invention is represented by Structural Formula

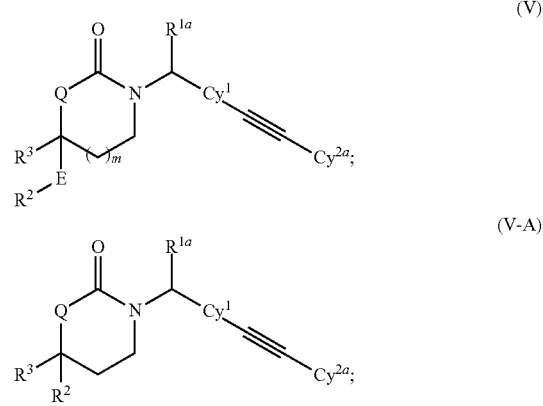

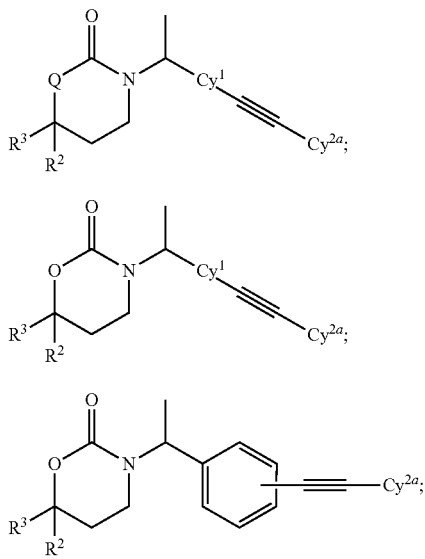

or a pharmaceutically acceptable salt, enantiomer or diastereomer thereof. $R^{1a}$ is optionally substituted $(C_1-C_6)$alkyl, $Cy^{2a}$ is an aryl, heteroaryl or heterocyclyl group, and is optionally substituted with 1 to 4 groups independently selected from halogen, —CN, $NO_2$, —$NH_2$, —OH, —COOH, —COOR$^6$, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkythio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NHR$^7$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH2, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano$(C_1-C_6)$alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$, and values and particular values for the remainder of the variables in Structural Formula (V)-(V-D) are as described above for Structural Formula (I).

In a 1$^{st}$ more specific embodiment for compounds of Structural Formula (V)-(V-D), $R^{1a}$, if present, is optionally substituted $(C_1-C_6)$alkyl, preferably, methyl or ethyl, and values and particular values for the remainder of the variables in Structural Formula (V)-(V-D) are as described above for Structural Formula (I).

In another specific embodiment for compounds of Structural Formula (V)-(V-D), $Cy^1$, if present, is an optionally substituted cyclohexyl, phenyl, pyridyl, pyrimidinyl, thiazolyl, triazolyl or benzothiazolyl group, and values and particular values for the remainder of the variables in Structural Formula (V)-(V-D) are as described above for Structural Formula (I).

In a 2$^{nd}$ more specific embodiment for compounds of Structural Formula (V)-(V-D), $R^{1a}$, if present, is an optionally substituted $(C_1-C_6)$alkyl, preferably, methyl or ethyl, $Cy^1$, if present, is an optionally substituted cyclohexyl, phenyl, pyridyl, pyrimidinyl, thiazolyl, triazolyl or benzothiazolyl group, and values and particular values for the remainder of the variables in Structural Formula (V)-(V-D) are as described above for Structural Formula (I).

In a 3$^{rd}$ more specific embodiment for compounds of Structural Formula (V)-(V-D), Q, if present, is O, CH$_2$ or NH; R$^{1a}$, if present, is an optionally substituted methyl or ethyl group, Cy$^1$, if present, is an optionally substituted cyclohexyl, phenyl, pyridyl, pyrimidinyl, thiazolyl, triazolyl or benzothiazolyl group, and values and particular values for the remainder of the variables in Structural Formula (V)-(V-D) are as described above for Structural Formula (I).

In a 4$^{th}$ more specific embodiment for compounds of Structural Formula (V)-(V-D), Q, if present, is O, CH$_2$ or NH, R$^{1a}$, if present, is an optionally substituted methyl or ethyl group, Cy$^1$, if present, is an optionally substituted cyclohexyl, phenyl, pyridyl, pyrimidinyl, thiazolyl, triazolyl or benzothiazolyl group, preferably, an optionally substituted phenyl group, Cy$^2$ is an optionally substituted methyl, ethyl, propyl, butyl, pentyl, hexyl, cyclopropyl, cyclobutyl, cyclopentyl, cyclohexyl, phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, or 1,1-dioxo-hexahydro-1,2-thiazinyl group, and values and particular values for the remainder of the variables in Structural Formula (V)-(V-D) are as described above for Structural Formula (I).

In a 5$^{th}$ more specific embodiment for compounds of Structural Formula (V)-(V-D), Cy$^1$, if present, is an optionally substituted cyclohexyl, phenyl, pyridyl, pyrimidinyl, thiazolyl, triazolyl or benzothiazolyl group, preferably, an optionally substituted phenyl group; Cy$^{2a}$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, or oxodihydrobenzimidazolyl group, preferably, Cy$^{2a}$ is an optionally substituted pyridyl or oxodihydropyridyl group. Cy$^{2a}$ is optionally substituted with one to three groups independently selected from —NH$_2$, —OH, —COOH, —COOR$^6$, —R$^6$, —C(=O)NHR$^7$; —C(=O)NR$^6$R$^6$, —C(=O)R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, and —NHS(=O)$_2$R$^6$. Alternatively, Cy$^{2a}$ is optionally substituted with one to three groups independently selected from —NH$_2$, —OH, —COOH, —COOMe, —OMe, cyclopropylcarbamoyl; —C(=O)NMe$_2$, azetidinylcarbonyl, —NHC(=O)Me, —NHC(=O)OMe, cyclopropanecarboxamido, —NHC(=O)NH$_2$, —NHC(=O)NHMe, —NHC(=O)NMe$_2$, oxooxazolidinyl, —OC(=O)OMe, and —NHS(=O)$_2$Me. Values and particular values for the remainder of the variables in Structural Formula (V)-(V-D) are as described above for Structural Formula (I).

In a 6$^{th}$ more specific embodiment for compounds of Structural Formula (V)-(V-D), Cy$^1$, if present, is optionally substituted phenyl, Cy$^{2a}$ is an optionally substituted pyridyl or oxodihydropyridyl group, the group represented by Cy$^{2a}$ is optionally substituted with one to three groups independently selected from —NH$_2$, —OH, —COOH, —COOMe, —OMe, cyclopropylcarbamoyl; —C(=O)NMe$_2$, azetidinylcarbonyl, —NHC(=O)Me, —NHC(=O)OMe, cyclopropanecarboxamido, —NHC(=O)NH$_2$, —NHC(=O)NHMe, —NHC(=O)NMe$_2$, oxooxazolidinyl, —OC(=O)OMe, and —NHS(=O)$_2$Me, and values and specific values for the remainder of the variables in Structural Formula (V)-(V-D) are as described above for Structural Formula (I).

Another embodiment of the present invention is a compound of Structural Formula (V), (V-A), (V-B), (V-C) or (V-D), or a pharmaceutically acceptable salt, enantiomer or diastereomer thereof, R$^{1a}$ and R$^{1b}$, if present, are independently optionally substituted with up to four groups independently selected from fluorine, cyano, oxo, (C$_1$-C$_6$)alkyl, halo (C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl and (C$_1$-C$_6$)alkoxy(C$_1$-C$_6$)alkyl, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NS(=O)$_2$NR$^4$— and R$^4$S(=O)$_2$NR$^4$—; R$^3$ is (C$_3$-C$_6$)alkenyl, hydroxy(C$_2$-C$_5$)alkyl, cyano(C$_2$-C$_5$)alkyl, dihydroxy(C$_3$-C$_5$)alkyl, ω-H$_2$NCO(C$_1$-C$_5$)alkyl, (C$_1$-C$_2$)alkoxy(C$_1$-C$_4$)alkyl, H$_2$NSO$_2$O(C$_2$-C$_5$)alkyl, H$_2$NSO$_2$NH(C$_2$-C$_5$)alkyl, oxo(C$_2$-C$_5$)alkyl, MeC(=O)NH(C$_2$-C$_5$)alkyl, MeSO$_2$NH(C$_2$-C$_5$)alkyl, or MeSO$_2$NH(C$_2$-C$_5$)alkyl. Alternatively, R$^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, MeS—, MeSO$_2$-MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe. Values and particular or specific values for the remainder of the variables are as described in Structural Formula (I), (V), (V-A), (V-B), (V-C) or (V-D) or the 1$^{st}$, 2$^{nd}$, 3$^{rd}$, 4$^{th}$, 5$^{th}$ or 6$^{th}$ more specific embodiments thereunder.

Another embodiment of the present invention is a compound of Structural Formula (V), (V-A), (V-B), (V-C) or (V-D), or a pharmaceutically acceptable salt, enantiomer or diastereomer thereof, R$^{1a}$ and R$^{1b}$, if present, are independently optionally substituted with up to four groups independently selected from fluorine, cyano, oxo, (C$_1$-C$_6$)alkyl, halo (C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl and (C$_1$-C$_6$)alkoxy(C$_1$-C$_6$)alkyl, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NS(=O)$_2$NR$^4$— and R$^4$S(=O)$_2$NR$^4$—; R$^2$ is an optionally substituted (C$_1$-C$_6$)alkyl, aryl, heteroaryl or cycloalkyl group; E, if present, is a bond or CH$_2$, and R$^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC=N)NH—, MeS—, MeSO$_2$—MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe. Alternatively, R$^3$ is (C$_3$-C$_6$)alkenyl, hydroxy(C$_2$-C$_5$)alkyl, cyano (C$_2$-C$_5$)alkyl, dihydroxy(C$_3$-C$_5$)alkyl, ω-H$_2$NCO(C$_1$-C$_5$) alkyl, (C$_1$-C$_2$)alkoxy(C$_1$-C$_4$)alkyl, H$_2$NSO$_2$O(C$_2$-C$_5$)alkyl, H$_2$NSO$_2$NH(C$_2$-C$_5$)alkyl, oxo(C$_2$-C$_5$)alkyl, MeC(=O)NH (C$_2$-C$_5$)alkyl, MeSO$_2$NH(C$_2$-C$_5$)alkyl, or MeSO$_2$NH(C$_2$-C$_5$) alkyl. Values and particular or specific values for the remainder of the variables are as described in Structural Formula (I), (V), (V-A), (V-B), (V-C) or (V-D) or the 1$^{st}$, 2$^{nd}$, 3$^{rd}$, 4$^{th}$, 5$^{th}$ or 6$^{th}$ more specific embodiments thereunder.

Another embodiment of the present invention is a compound of Structural Formula (V), (V-A), (V-B), (V-C) or (V-D), or a pharmaceutically acceptable salt, enantiomer or diastereomer thereof, R$^2$ is phenyl, fluorophenyl, isopropyl, cyclopropyl, t-butyl, cyclopropylmethyl or trifluoroethyl;

R$^3$ is 2-methylallyl, 2-hydroxy-2-methylpropyl or 2-cyano-2-methylpropyl; the group represented by Cy$^1$ is optionally substituted with fluoro, chloro, cyano, CONH$_2$, CONHMe, CONMe$_2$, CONHc-Pr, methyl, ethyl, cyclopropyl, CF$_3$ or oxo; and the group represented by Cy$^{2a}$ is optionally substituted with (C$_1$-C$_6$)alkoxy, and values and particular or specific values for the remainder of the variables are described in Structural Formula (I), (V), (V-A), (V-B), (V-C) or (V-D) or the 1$^{st}$, 2$^{nd}$, 3$^{rd}$, 4$^{th}$, 5$^{th}$ or 6$^{th}$ more specific embodiments thereunder.

Preferred values for the variables in the above-described Structural Formula ((I), (II), (II-A), (II-B), (II-C), (II-D), (III), (III-A), (III-B), (III-C), (III-D), (III-E) (IV), (IV-A), (IV-B), (IV-C), (IV-D), (V), (V-A), (V-B), (V-C) or (V-D) are provided below:

Q is O or CH$_2$ and n is 1. Alternatively, Q is O or NR$^5$ and n is 1. Alternatively, Q is O or NH and n is 1. Alternatively, Q is O and n is 1. Alternatively, Q is O or CH$_2$, E is a bond and n is 1. Alternatively, Q is O or NR$^5$, E is a bond and n is 1. Alternatively, Q is O or NH, E is a bond and n is 1. Alternatively, Q is O, E is a bond and n is 1. Alternatively, E is a bond and n is 1. Alternatively, Q is O or NR$^5$ and E is a bond. Alternatively, Q is O or NH and E is a bond. Alternatively, Q is O and E is a bond. Alternatively, Q is O or CH$_2$, n is 1 and A$^1$ is a bond. Alternatively, Q is O or NR$^5$, n is 1 and A$^1$ is a bond. Alternatively, Q is O or NH, n is 1 and A$^1$ is a bond. Alternatively, Q is O, n is 1 and A$^1$ is a bond. Alternatively, Q is O or CH$_2$, E is a bond, n is 1 and A$^1$ is a bond. Alternatively, Q is O or NR$^5$, E is a bond, n is 1 and A$^1$ is a bond. Alternatively, Q is O or NH, E is a bond, n is 1 and $A^1$ is a bond. Alternatively, Q is O, E is a bond, n is 1 and $A^1$ is a bond. Alternatively, E is a bond, n is 1 and $A^1$ is a bond. Alternatively, Q is O or $NR^5$, E is a bond and $A^1$ is a bond. Alternatively, Q is O or NH, E is a bond and $A^1$ is a bond. Alternatively, Q is O, E is a bond and $A^1$ is a bond. Alternatively, Q is O or $CH_2$, n is 1 and $A^2$ is a bond.

$R^{1a}$ and $R^{1b}$ are, independently, optionally substituted ($C_1$-$C_6$)alkyl. Alternatively, $R^{1a}$ and $R^{1b}$ are, independently, an optionally substituted methyl or ethyl group. Alternatively, $R^{1a}$ and $R^{1b}$ are, independently, optionally substituted methyl. Alternatively, $R^{1a}$ and $R^{1b}$ are, independently, ($C_1$-$C_6$)alkyl optionally substituted with up to four groups independently selected from fluorine, cyano, oxo, $R^4$, $R^4O—$, $(R^4)2N—$, $R^4O_2O—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NS(=O)_2NR^4—$ and $R^4S(=O)_2NR^4—$. Alternatively, $R^{1a}$ and $R^{1b}$ are, independently, a methyl or ethyl group. the groups represented by $R^{1a}$ and $R^{1b}$ being, independently, optionally substituted with up to four groups independently selected from fluorine, cyano, oxo, $R^4$, $R^4O—$, $(R^4)_2N—$, $R^4O_2O—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NS(=O)_2NR^4—$ and $R^4S(=O)_2NR^4—$. Alternatively, $R^{1a}$ and $R^{1b}$ are, independently, methyl optionally substituted with up to four groups independently selected from fluorine, cyano, oxo, $R^4$, $R^4O—$, $(R^4)_2N—$, $R^4O_2O—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NS(=O)_2NR^4—$ and $R^4S(=O)_2NR^4—$. Alternatively, $R^{1a}$ is methyl and $R^{1b}$ is ethyl. Alternatively, $R^{1a}$ and $R^{1b}$ are ethyl. Alternatively, $R^{1a}$ and $R^{1b}$ taken together with the carbon to which they are attached form an optionally substituted ($C_3$-$C_6$)cycloalkyl ring. Alternatively, $R^{1a}$ and $R^{1b}$ taken together with the carbon to which they are attached form an optionally substituted cyclopropyl or cyclobutyl group. Alternatively, $R^{1a}$ and $R^{1b}$ taken together with the carbon to which they are attached form an optionally substituted cyclopropyl group. Alternatively, $R^{1a}$ and $R^{1b}$ taken together with the carbon to which they are attached form an unsubstituted ($C_3$-$C_6$)cycloalkyl ring. Alternatively, $R^{1a}$ and $R^{1b}$ taken together with the carbon to which they are attached form an unsubstituted cyclopropy or cyclobutyl group. Alternatively, $R^{1a}$ and $R^{1b}$ taken together with the carbon to which they are attached form an unsubstituted cyclopropyl group.

Alternatively, $R^{1a}$ and $R^{1b}$ taken together with the carbon to which they are attached form a ($C_3$-$C_6$)cycloalkyl ring optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NS(=O)_2NR^4—$ and $R^4S(=O)_2NR^4—$. Alternatively, $R^{1a}$ and $R^{1b}$ taken together with the carbon to which they are attached form a cyclopropy or cyclobutyl group optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NS(=O)_2NR^4—$ and $R^4S(=O)_2NR^4—$. Alternatively, $R^{1a}$ and $R^{1b}$ taken together with the carbon to which they are attached form a cyclopropyl group optionally substituted with up to four groups independently selected from fluorine, cyano, oxo, $R^4$, $R^4O—$, $(R^4)_2N—$, $R^4O_2C—$, $R^4S$, $R^4S(=O)—$, $R^4S(=O)_2—$, $R^4C(=O)NR^4—$, $(R^4)_2NC(=O)—$, $(R^4)_2NC(=O)O—$, $(R^4)_2NC(=O)NR^4—$, $R^4OC(=O)NR^4—$, $(R^4)_2NS(=O)_2NR^4—$ and $R^4S(=O)_2NR^4—$.

DEFINITIONS

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

"Alkynyl" is an alkyl group in which at least one carbon-carbon bond has been replaced with a triple bond.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an carbocyclic aromatic radical with six to fourteen carbon atoms. Examples include phenyl, a naphthyl, indanyl or a tetrahydronaphthalene. A substituted aryl group has 1-4 substituents. Unless otherwise indicated, exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido. The term "aryl" may be used interchangeably with the terms "aryl ring" "carbocyclic aromatic ring", "aryl group" and "carbocyclic aromatic group".

The term "heteroaryl" means a 5- and 12-membered heteroaromatic radical containing 0-4 heteroatoms selected from N, O, and S. A heteroaryl can be monocyclic or bicyclic, for example, fused to an aryl, monocyclic heteroaryl, heterocyclyl or cycloalkyl group. Examples include 2- or 3-thienyl, 2- or 3-furanyl, 2- or 3-pyrrolyl, 2-, 3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A substituted heteroaryl has from 1-4 substitutents. Unless otherwise indicated, exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide. The term "heteroaryl", "heteroaromatic", "heteroaryl ring", "heteroaryl group", "heteroaromatic ring", and "heteroaromatic group" are used interchangeably.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2,2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1, 6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A substituted heterocyclyl has 1-4 substituents. Unless otherwise indicated, exemplary substituents include alkyl, haloalkyl, halogen and oxo.

The term "spirocycloalkyl" means a cycloalkyl group which shares one ring carbon with another alkyl or cycloalkyl group.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "compound" also includes labeling at one or more positions with deuterium. "Labeled with deuterium at a position" means that the amount deuterium at the position is greater than the amount that is present at natural abundance. In certain instances, the deuterium at each position in a "compound" is at natural abundance.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers, i.e., stereochemically pure. "Stereochemical purity" is the weight of the stereoisomer divided by the combined weight of all of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer divided by the combined weight of the enantiomer and the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
| --- | --- |
| A % | Area percentage |
| Boc | tert-butoxy carbonyl or t-butoxy carbonyl |
| (Boc)₂O | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo[5.4.0]undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |
| DIEA | N,N-diisopropylethylamine |
| DMAP | 4-(dimethylamino)pyridine |
| DMF | N,N-dimethylformamide |

| Abbreviation | Meaning |
|---|---|
| DMPU | 1,3-dimethyl-3,4,5,6-tetrahydro-2(1H)-pyrimidinone |
| 2,4-DNP | 2,4-dinitrophenylhydrazine |
| dppf | 1,1'-Bis(diphenylphosphino)ferrocene |
| DPTBS | Diphenyl-t-butylsilyl |
| dr | diastereomer ratio |
| EDC•HCl, EDCI | 1-[3-(dimethylamino)propyl]-3-ethylcarbodiimide hydrochloride |
| Equiv | equivalents |
| EtOAc | Ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-yl)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| T$_{ext}$ | External temperature |
| T$_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| t$_R$ | retention time |
| TsOH | p-toluenesulfonic acid |

GENERAL DESCRIPTION OF SYNTHETIC METHODS

Compounds of Formula I can be prepared by several processes. In the discussion below, $A^1$, $Cy^1$, $Cy^2$, Q, E, $R^{1a}$, $R^{1b}$, $R^2$, $R^3$, Y, m and n have the meanings indicated above unless otherwise noted. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I, wherein Q=O or $NR^5$, can be prepared by reaction of an aminoalcohol (Q=O) or diamine (Q=$NR^5$) intermediate of Formula 2 with a reagent of Formula 3, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at $-10°$ C. to $120°$ C.:

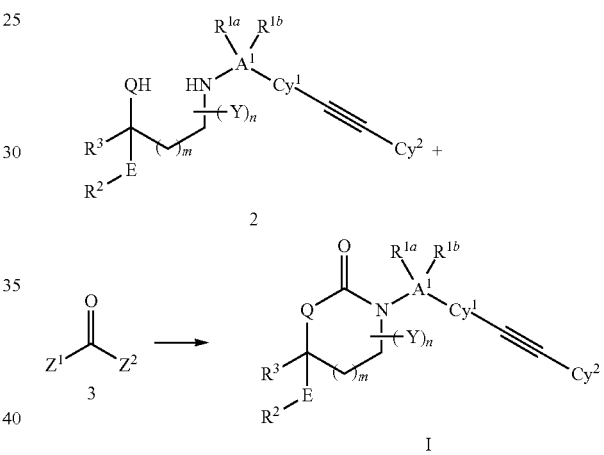

Certain instances of reagent 3 are especially convenient because they are commercially available. For example when $Z^1$ and $Z^2$ are both chloride, 3 is phosgene. When $Z^1$ and $Z^2$ are both 1-imidazolyl, 3 is carbonyl diimidazole. When $Z^1$ is chloride and $Z^2$ is p-nitrophenoxide, 3 is p-nitrophenyl chloroformate. When $Z^1$ and $Z^2$ are both $OCCl_3$, 3 is triphosgene and as little as one third of molar equivalent can be used.

Intermediates of Formula 2 can be prepared by reduction of amides of Formula 4 using a hydride reagent such as $BH_3$.THF solution, $BH_3.Me_2S$ or $LiAlH_4$ in an inert solvent ethereal such as THF or DME at $20°$ C. to $100°$ C. for between 1 h and 48 h:

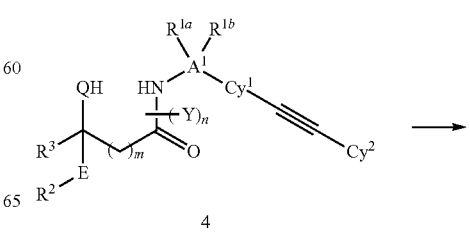

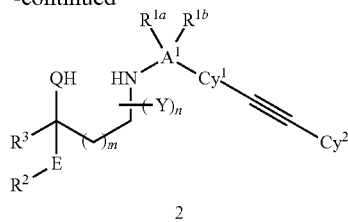

2

Intermediates of Formula 4, can be prepared by coupling of an α-, β- or γ-hydroxyacid of Formula 5 (Q=O) or a protected α-, β- or γ-amino acid of Formula 5 (Q=NR⁵) with an amine of Formula 6 using standard peptide coupling reagents such as EDC in the presence of HOBt and N,N-diisopropylethylamine in an inert solvent such as $CH_2Cl_2$ at 0-30° C. for between 1 h and 24 h:

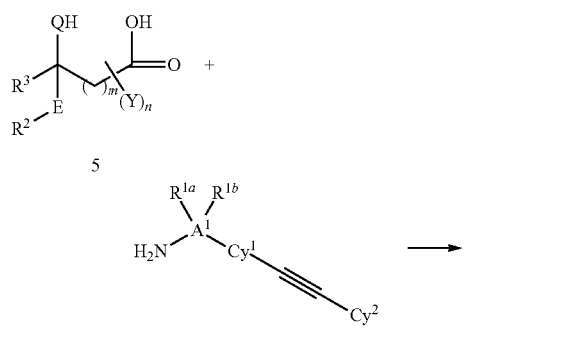

Amines of Formula 6 can be prepared by Ritter reaction of alcohols of Formula 7 with HCN:

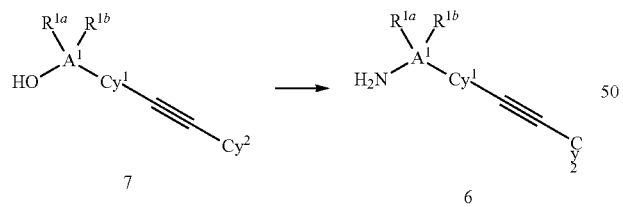

Amines of Formula 6, wherein $R^{1a}=R^{1b}$, can be prepared by double addition of organometallic reagents of Formula 8, wherein M is preferably Li, to nitriles of Formula 9:

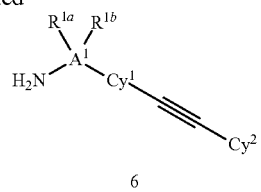

6

Amines of Formula 6 can also be prepared by Hoffman or Curtius rearrangement of carboxylic acids of Formula 10, using for example diphenylphosphoryl azide:

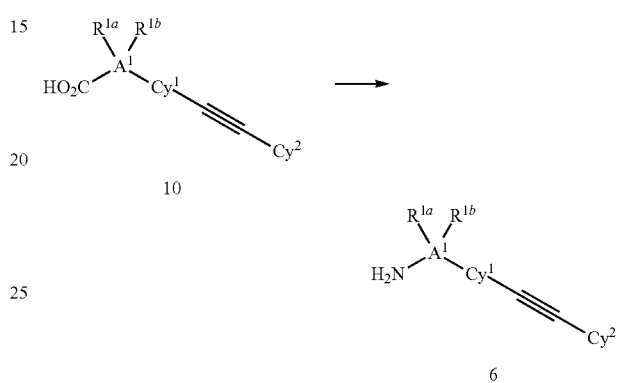

Intermediates of Formula 2, wherein Q=O, n=0 and m=0 or 1, can be prepared by reaction of epoxides (m=0) or oxetanes (m=1) of Formula 11 with amines of Formula 6:

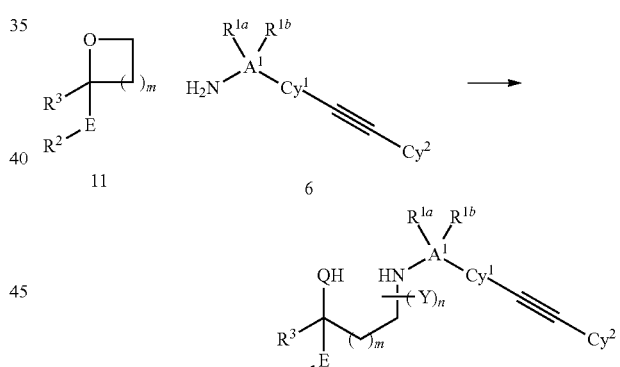

Intermediates of Formula 2, wherein Q=O or protected NR⁵, can also be prepared by reductive amination of aldehydes of Formula 12 with amines of Formula 6. Methods for the reductive amination of aldehydes are described in Baxter, E. W. and Reitz, A. B. "Organic Reactions" Volume 59, Ed. Overman, L. E., Wiley Interscience, 2002.

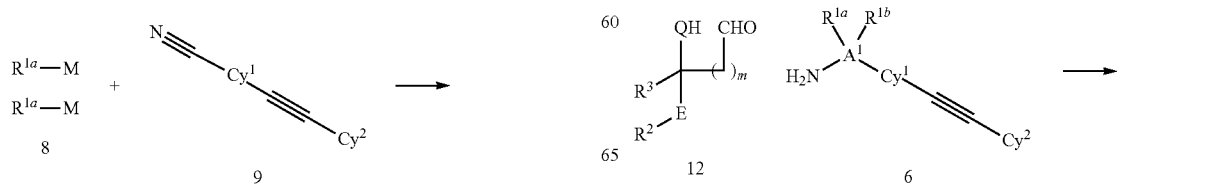

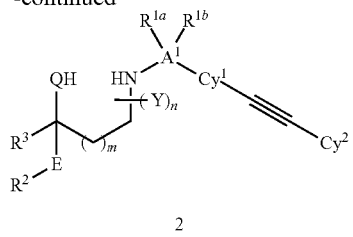

Amine intermediates of Formula 2, wherein Q=O or protected $NR^5$, can be prepared by reaction of halides or sulfonates of Formula 13, wherein $R^E$ is halide or $OSO_2R^A$ ($R^A$=alkyl, haloalkyl or arylalkyl), with amines of Formula 6:

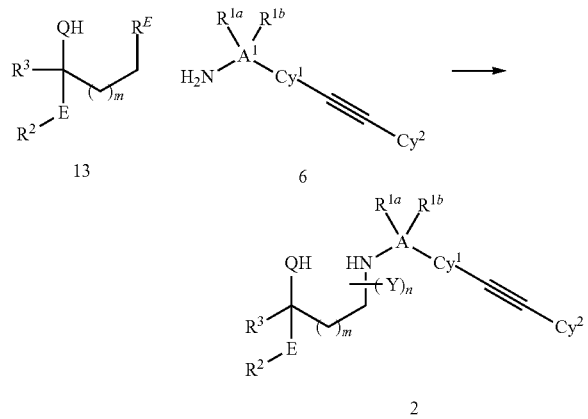

Sulfonate intermediates of Formula 13, wherein Q=O and $R^E=OSO_2R^A$, can be prepared from diol intermediates of Formula 14 with a sulfonyl chloride $R^ASO_2Cl$:

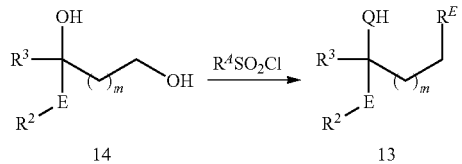

Diol intermediates of Formula 14, wherein m=1, can be prepared by hydroboration of allyl alcohols of Formula 15:

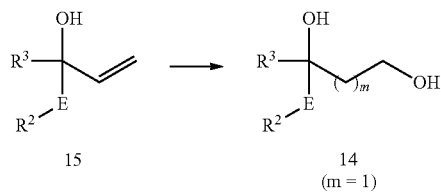

Diol intermediates of Formula 14, wherein m=0, can be prepared by ozonolysis and reduction of allyl alcohols of Formula 15:

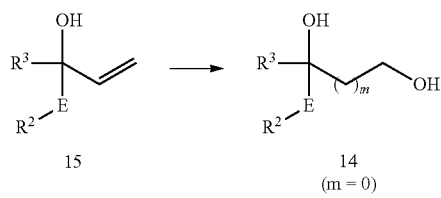

Halide intermediates of Formula 13, wherein Q=H, n=1 and $R^E$ is chloride can be prepared by addition of an organometallic reagent of Formula 16, wherein M is Li, MgCl, MgBr, MgI, ZnI optionally in the presence of $CeCl_3$, with a ketone intermediate of Formula 17:

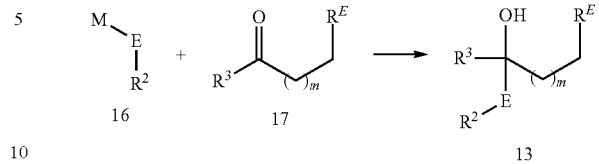

In a second process a compound of Formula I, wherein Q=O and n=0 or 1, can be prepared by reaction of a hydroxycarbamate of Formula 18, wherein $R^B$ is alkyl or arylalkyl group such as methyl, t-butyl or benzyl, with a strong base such as NaH:

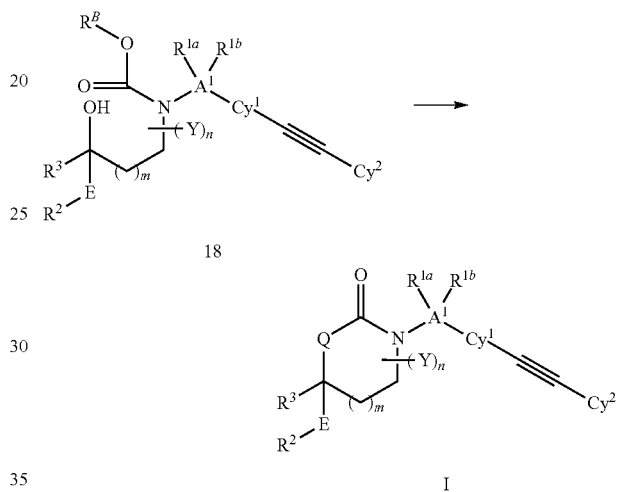

A hydroxycarbamate of Formula 18 can be prepared by reaction of an amine of Formula 2, wherein Q=O, with a chloroformate of Formula $R^BOCOCl$ or when $R^B$=t-Bu with $Boc_2O$.

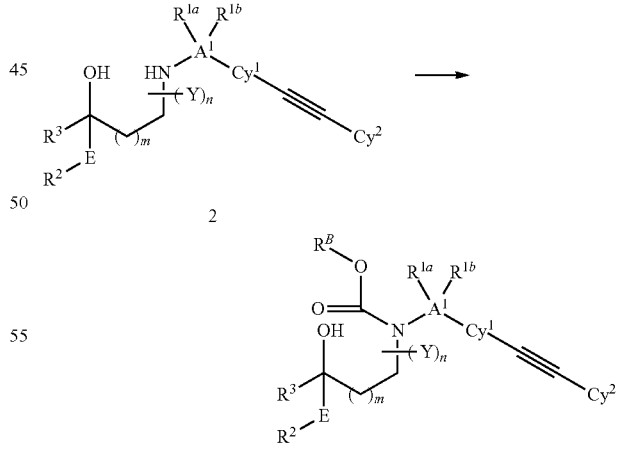

In a third process a compound of Formula I can be prepared by reaction of a ketocarbamate of Formula 19, wherein $R^B$ is alkyl or arylalkyl group such as methyl, t-butyl or benzyl, with an organometallic reagent of Formula 20 wherein M includes, but is not limited to, MgCl, MgBr, MgI or Li:

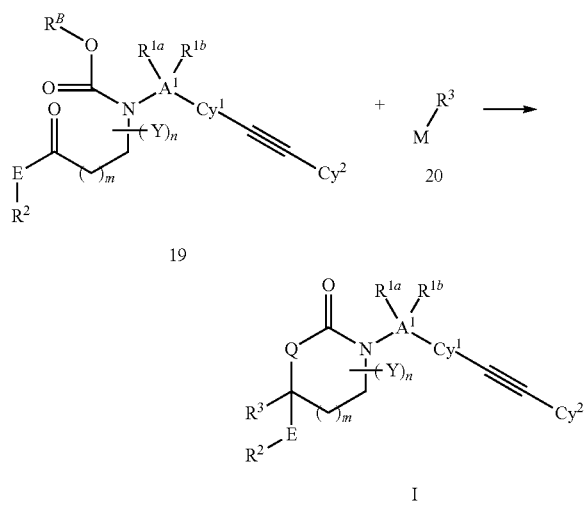

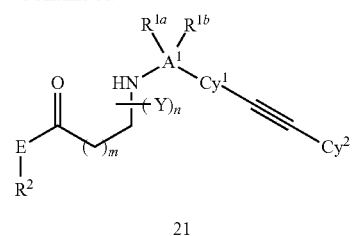

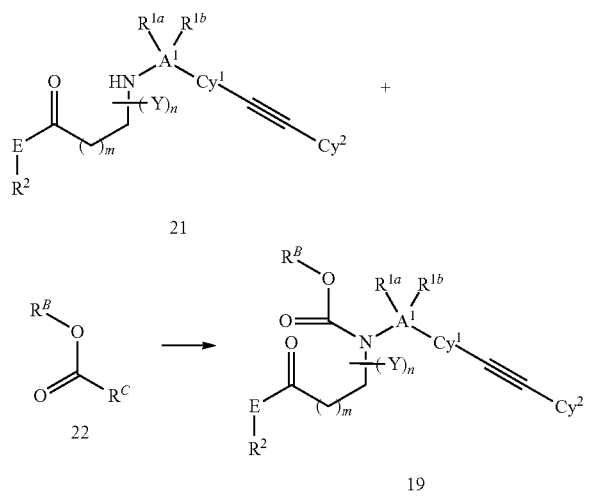

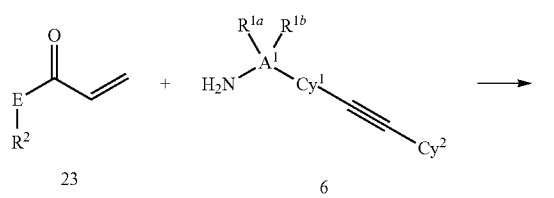

In specific examples, organometallic reagent 20 is allylmagnesium bromide, allylzinc(II) bromide, (2-methylallyl)magnesium chloride or (2-methoxy-2-oxoethyl)zinc(II) bromide. In certain cases when M is MgCl, MgBr or MgI, it is advantageous to add CeCl₃ to the reaction mixture.

Ketocarbamates of Formula 19 can be prepared by reaction of aminoketones of Formula 21 with intermediates of Formula 22 wherein $R^C$ is a leaving group such as chloride, succinyloxy, imidazolyl or t-butoxycarboxycarbonyl:

Aminoketones of Formula 21, wherein m=1, can be prepared by reaction of β-dialkylaminoketones of Formula 23a, wherein $R^F$ is lower alkyl especially methyl, with amines of Formula VI:

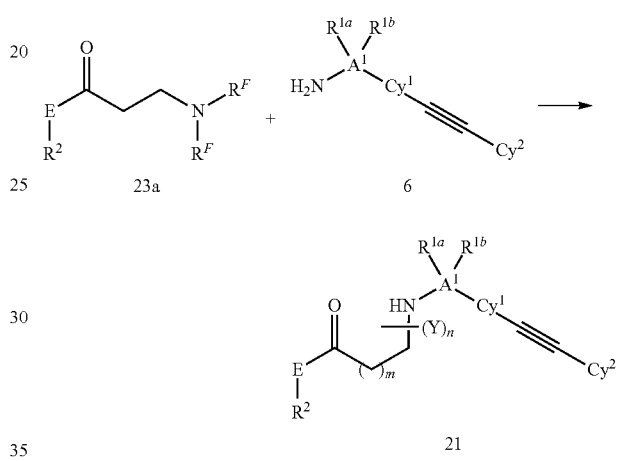

β-Dialkylaminoketones of Formula 23a are in turn derived from α, β-unsaturated ketones of Formula 23 with dialkylamines of Formula $R^F NHR^F$.

Aminoketones of Formula 21, wherein m=0 and n=0, can be prepared from α-haloketones of Formula 24 and amines of Formula 6:

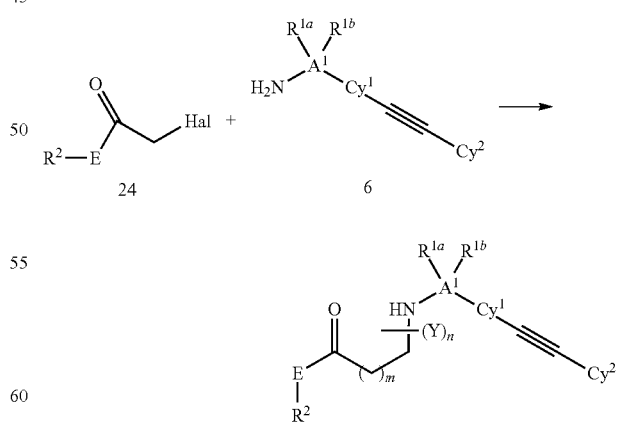

Aminoketones of Formula 21, wherein m=1, can be prepared by reaction of α,β-unsaturated ketones of Formula 23 with amines of Formula 6:

Diamine intermediates of Formula 2, wherein Q=NH, can be prepared by addition of organometallic reagents of Formula 20 to t-butylsulfinylimines of Formula 25:

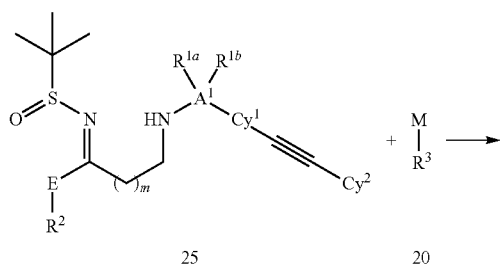

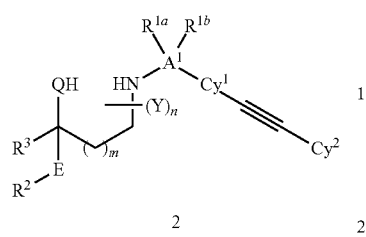

t-Butylsulfinylimines of Formula 25 can be prepared from aminoketones of Formula 21 by reaction with t-butylsulfinamide:

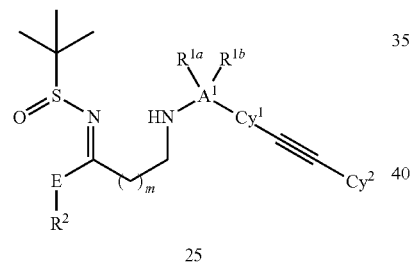

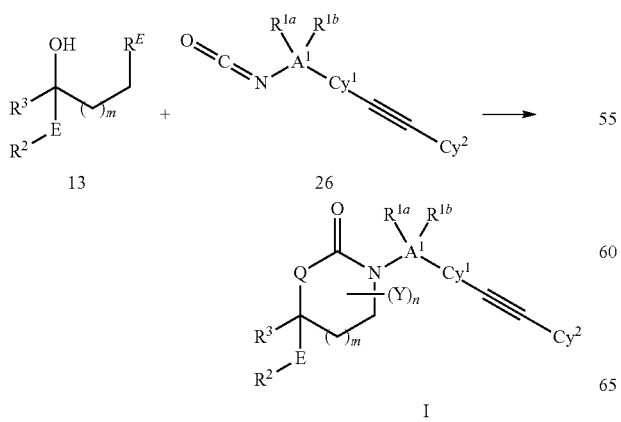

In some instances, use of 25 derived (R) or (S) t-BuSO$_2$NH$_2$ affords enantiomerically enriched 2.

In a fourth process a compound of Formula I, wherein Q=O, can be prepared by reaction of a compound of Formula 13 with an isocyanate of Formula 26 in the presence of a base:

Isocyanates of Formula 26 can be prepared from amines of Formula 6 by treatment with phosgene, diphosgene or triphosgene.

In a fifth process a compound of Formula I, wherein Q=CH$_2$, can be prepared from a compound of Formula 27, wherein R$^B$ is a alkyl or arylalkyl group, especially methyl or ethyl, and R$^E$ is a leaving group such as halide or OSO$_2$R$^A$ (R$^A$=alkyl, haloalkyl or arylalkyl), and an amine of Formula 6:

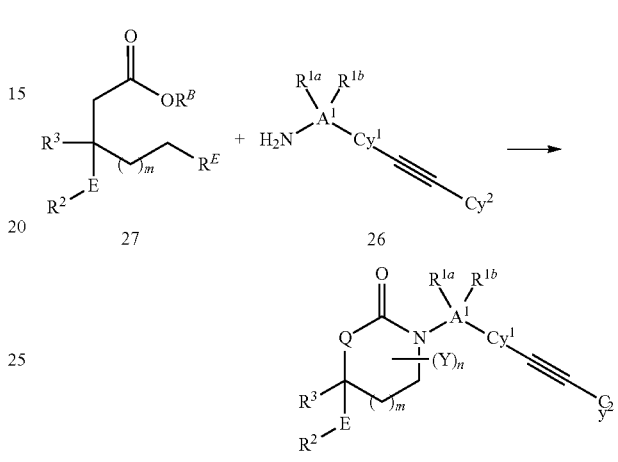

Intermediates of Formula 27, wherein E is a bond, R$^2$ is an aryl or heteroaryl group, R$^E$ is chloro and R$^3$ is allyl, can be prepared from alcohols of Formula 28 by treatment with allyltrimethylsilane in the presence of TiCl$_4$.

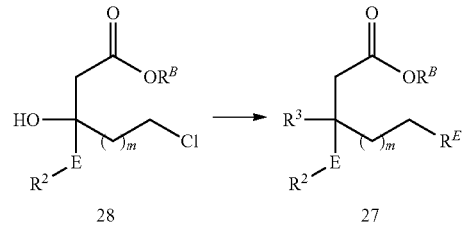

Alcohols of Formula 28 can be prepared by Reformatsky reaction of alkyl bromoacetates of Formula 29 with β-chloroketones of Formula 30.

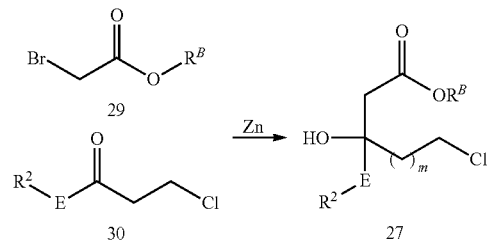

In a sixth process a compound of Formula I, wherein Q=CH$_2$ and R$^3$ is CH$_2$CH$_2$OH, can be prepared from an aminolactone of Formula 32 by heating,

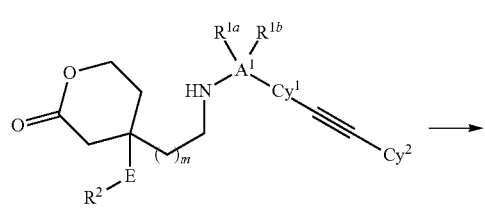

32

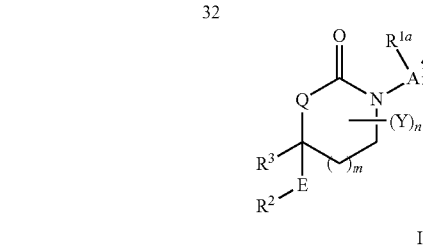

I

An aminolactone of Formula 32 can be prepared by reductive amination of an aldehyde of Formula 33 with an amine of Formula 6 using, for example, hydride reducing agents such as NaCNBH$_3$ or NaB(OAc)$_3$H.

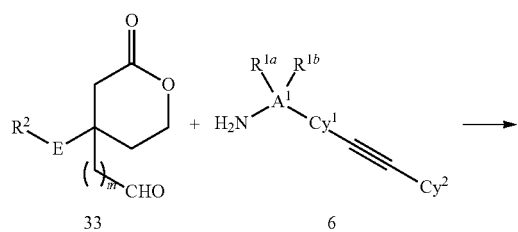

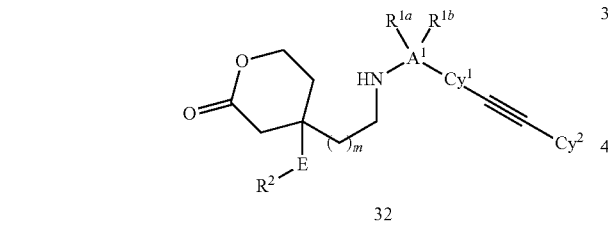

32

An aldehyde of Formula 33, wherein m=1, can be prepared from an allyl compound of Formula 34 by ozonolysis followed by mild oxidation with, for example, Dess-Martin reagent or DMSO/oxalyl chloride. An aldehyde of Formula 33, wherein m=2, can be prepared by hydroboration of an allyl lactone of Formula 34.

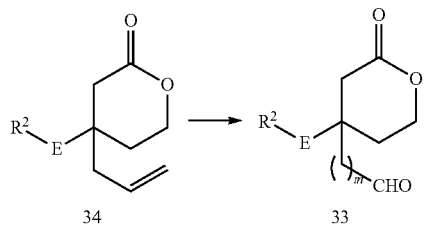

Allyl lactones of Formula 34 can be prepared by heating chloroesters of Formula 35. Chloroesters of Formula 35 can in turn be prepared from hydroxyesters of Formula 36 by treatment with allylsilane in the presence of TiCl$_4$. Hydroxyesters of Formula 36 are available by Reformatsky reaction of α-bromoacetates of Formula 37 and β-chloroketones of Formula 38.

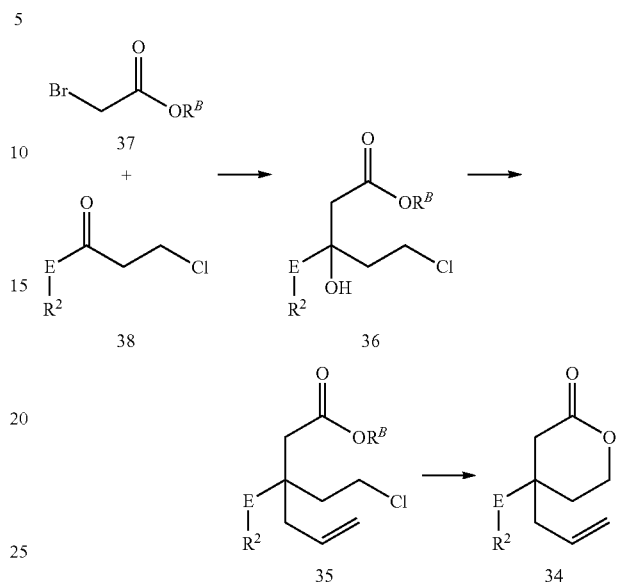

In a seventh process, a compound of Formula I can be prepared by Sonogashira reaction of a compound of Formula 39, wherein R$^J$ is bromo, iodo or trifluoromethanesulfonyloxy with an alkyne of Formula 40 in the presence of a palladium catalyst and the optional presence of a copper cocatalyst (Chinchilla, R.; Najera, C. *Chem. Rev.* 2007, 107, 874-922).

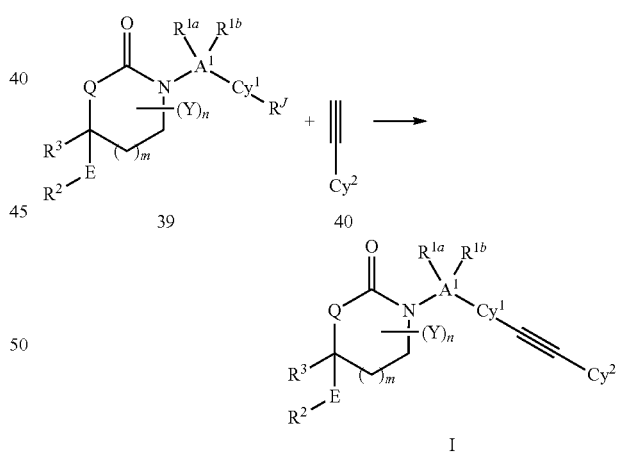

Compounds of Formula 39 can be prepared by adaptation of the first through sixth processes described above. For example a compound of Formula 39, wherein R$^3$ is 2-hydroxy-2-methylpropyl, E is a bond, R$^2$ is phenyl, m is 1, Q is O, R$^{1a}$ is methyl, A$^1$ is C, R$^{1b}$ is H, Cy$^1$ is 1,4-phenylene and R$^J$ is bromo can be prepared as described in WO 2009/017664. A compound of Formula 39, wherein R$^3$ is 2-hydroxy-2-methylpropyl, E is a bond, R$^2$ is phenyl, m is 1, Q is NH, R$^{1a}$ is methyl, A$^1$ is C, R$^{1b}$ is H, Cy$^1$ is 1,4-phenylene and R$^J$ is bromo can be prepared as described in WO 2009/061498.

51

A compound of Formula 39, wherein $R^3$ is 2-hydroxy-2-methylpropyl, E is a bond, $R^2$ is phenyl, m is 1, Q is $CH_2$, $R^{1a}$ is methyl, $A^1$ is C, $R^{1b}$ is H, $Cy^1$ is 1,4-phenylene and $R^J$ is bromo can be prepared as follows:

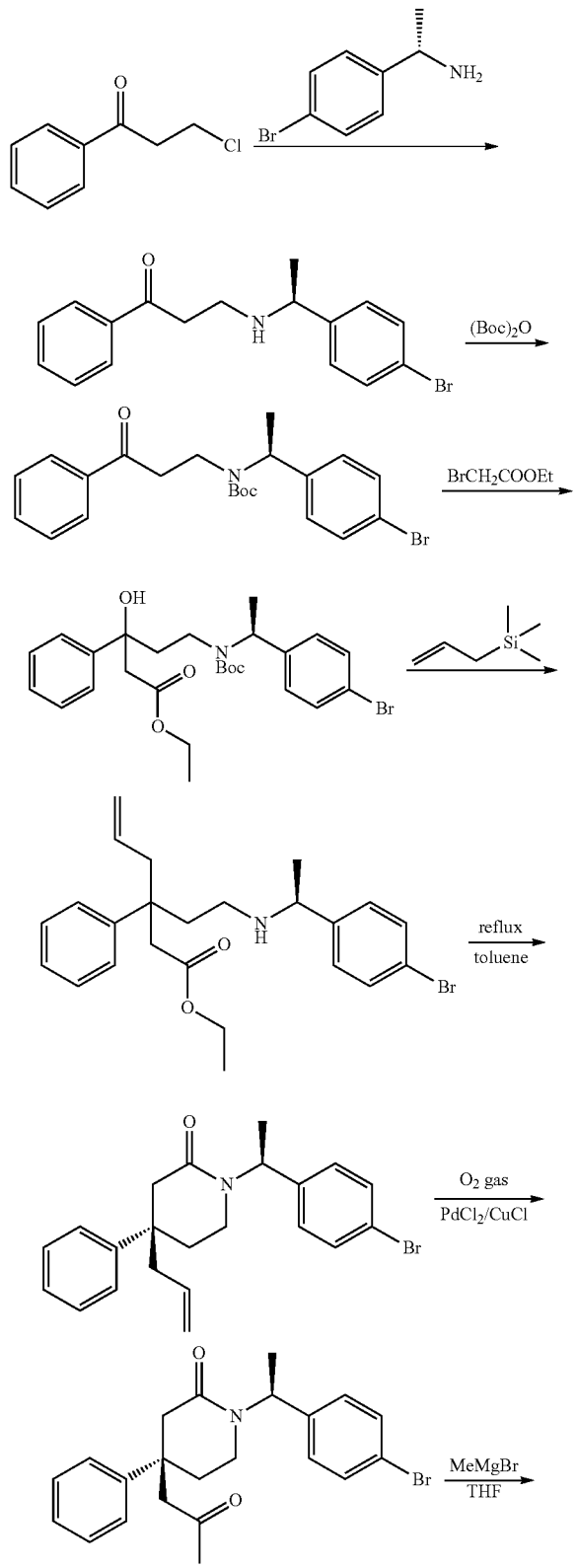

52

-continued

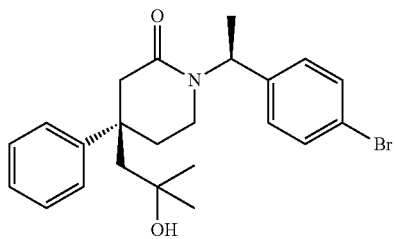 [SMILES: C[C@@H](c1ccc(Br)cc1)N1CC[C@](CC(C)(C)O)(c2ccccc2)CC1=O]

A compound of Formula 39, wherein $R^3$ is 3-hydroxypropyl, E is a bond, $R^2$ is phenyl, m is 2, Q is NH, $R^{1a}$ is methyl, $A^1$ is C, $R^{1b}$ is H, $Cy^1$ is 1,4-phenylene and $R^J$ is bromo can be prepared as described can be prepared as follows:

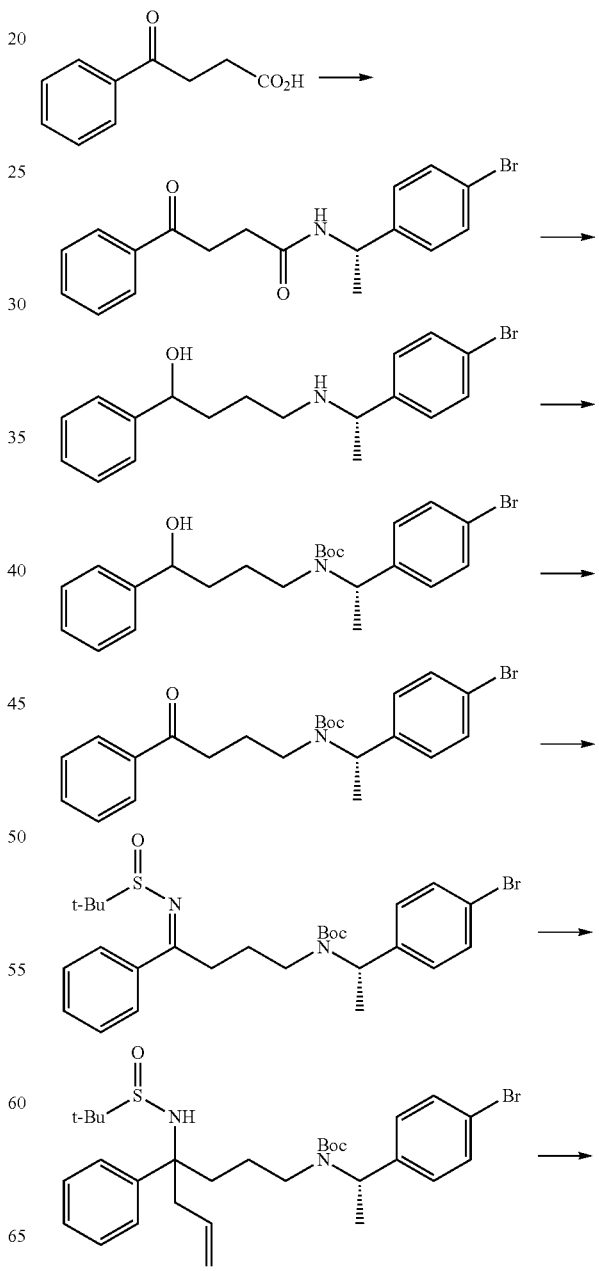

-continued

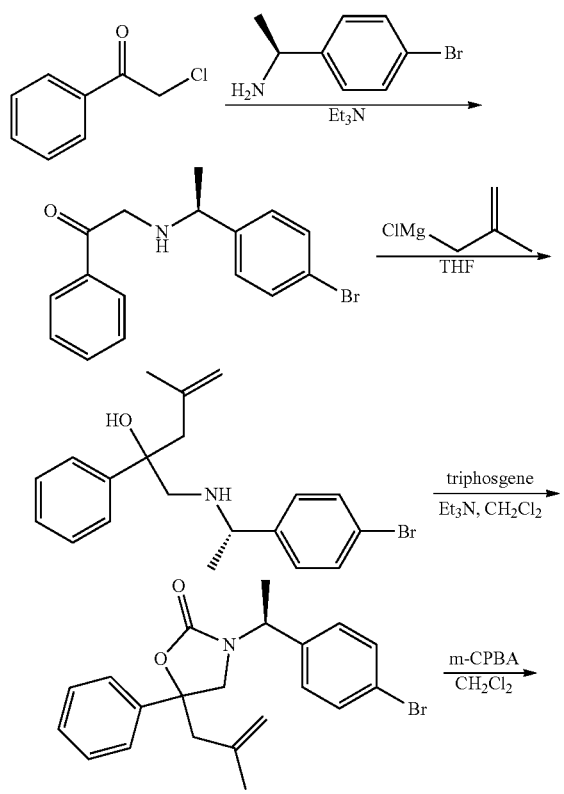

A compound of Formula 39, wherein $R^3$ is 2-hydroxy-2-methylpropyl, E is a bond, $R^2$ is phenyl, m is 0, Q is O, $R^{1a}$ is methyl, $A^1$ is C, $R^{1b}$ is H, $Cy^1$ is 1,4-phenylene and $R^J$ is bromo can be prepared as described can be prepared as follows:

-continued

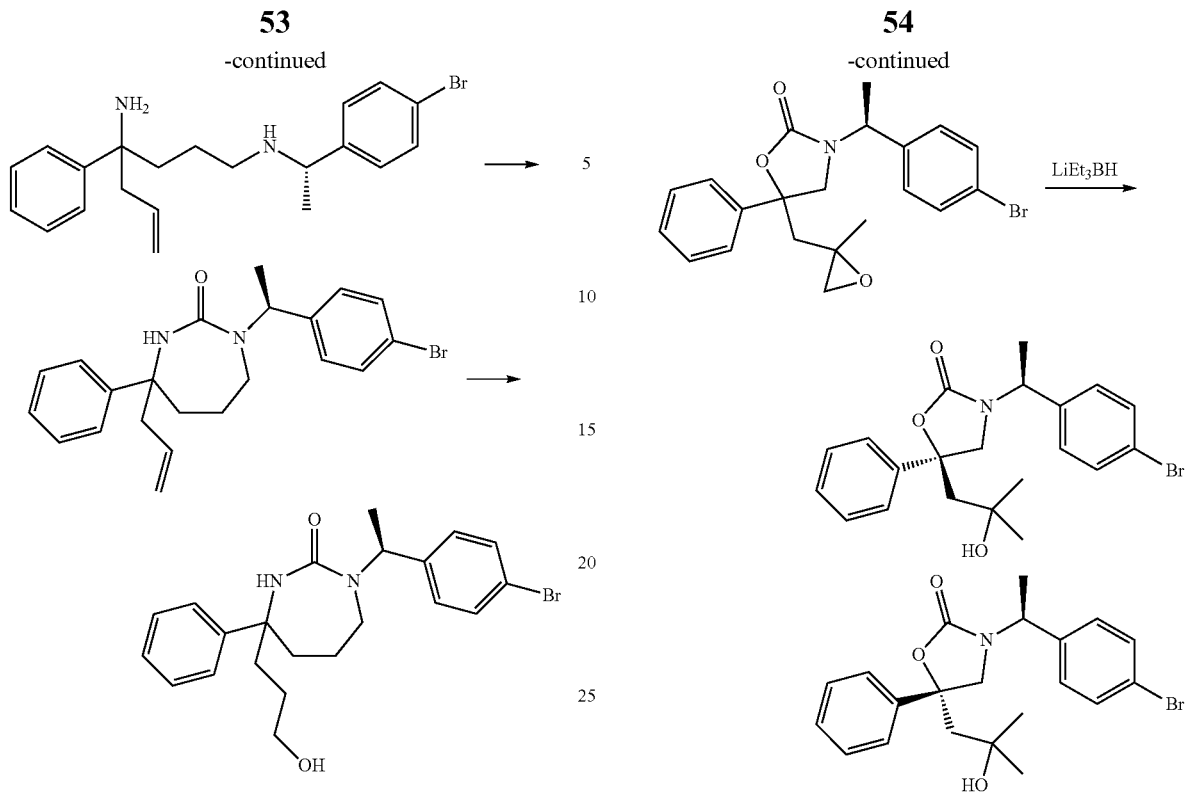

In an eighth process, a compound of Formula I, wherein $Cy^2$ is an aryl or heteroaryl ring, can be prepared by Sonogashira coupling of an alkyne of Formula 41 with a compound of Formula 42, wherein $R^J$ is bromo, iodo or trifluoromethanesulfonyloxy in the presence of a palladium catalyst and the optional presence of a copper cocatalyst (Chinchilla, R.; Najera, C. *Chem. Rev.* 2007, 107, 874-922).

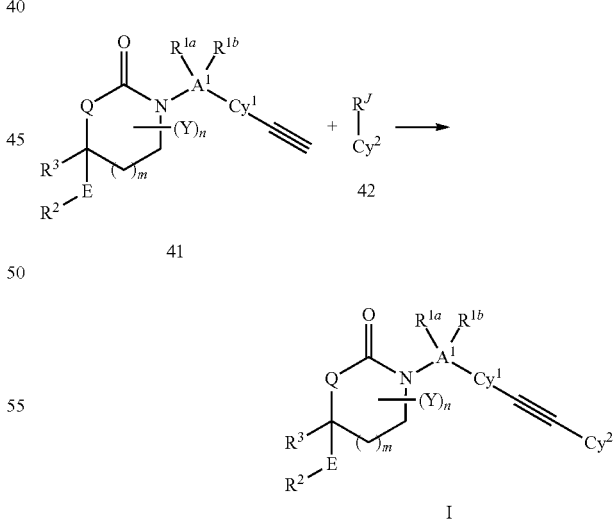

A compound of Formula 41 can be prepared from a compound of Formula 39 by Sonogashira reaction with an alkyne of Formula 43, wherein groups $R^K$ are independently selected from $(C_1$-$C_6)$alkyl and phenyl, in the presence of a palladium catalyst and the optional presence of a copper cocatalyst, followed by fluoride mediated removal of the silyl group.

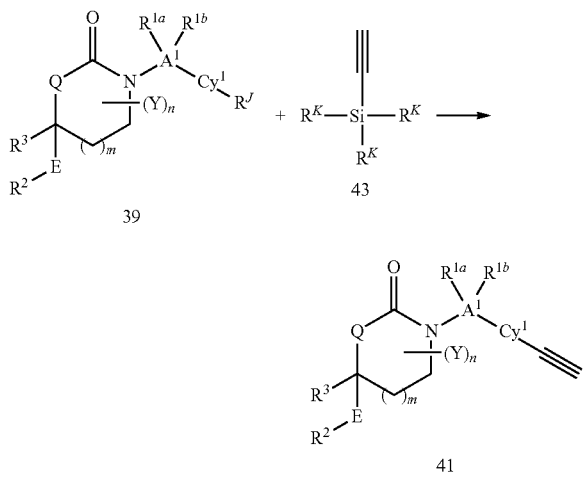

In a ninth process a compound of Formula I can be prepared from another compound of Formula I. For example:

(1) a compound of Formula I wherein $R^{1a}$, $R^{1b}$ or $R^3$ is ω-hydroxy($C_2$-$C_6$)alkyl can be oxidized to a compound of Formula I wherein $R^{1a}$, $R^{1b}$ or $R^3$ is ω-carboxy($C_1$-$C_5$)alkyl using Jones reagent.

(2) a compound of Formula I wherein $R^{1a}$, $R^{1b}$ or $R^3$ is ω-carboxy($C_1$-$C_6$)alkyl can be coupled with ammonia or a ($C_1$-$C_6$)alkylamine using a standard peptide coupling reagent such as EDC to afford a compound of Formula I wherein $R^{1a}$, $R^{1b}$ or $R^3$ is ω-$H_2$NC(=O)($C_1$-$C_6$)alkyl or ω-{($C_1$-$C_6$)alkylNHC(=O)}($C_1$-$C_6$)alkyl.

(3) a compound of Formula I wherein $R^{1a}$, $R^{1b}$ or $R^3$ is ω-hydroxy($C_1$-$C_6$)alkyl can be converted to its methanesulfonate or trifluoromethanesulfonate, treated with sodium azide and reduced to give a compound of Formula I, wherein $R^{1a}$, $R^{1b}$ or $R^3$ is ω-amino($C_1$-$C_6$)alkyl.

(4) a compound of Formula I wherein $R^{1a}$, $R^{1b}$ or $R^3$ is amino($C_1$-$C_6$)alkyl can be reacted with acetic anhydride or acetyl chloride to give a compound of Formula I wherein $R^{1a}$, $R^{1b}$ or $R^3$ is {acetylamino}($C_1$-$C_6$)alkyl.

(5) a compound of Formula I wherein $R^{1a}$, $R^{1b}$ or $R^3$ is amino($C_1$-$C_6$)alkyl can be reacted with methanesulfonyl chloride to give a compound of Formula I wherein $R^{1a}$, $R^{1b}$ or $R^3$ is {methanesulfonylamino}($C_1$-$C_6$)alkyl.

(6) a compound of Formula I, wherein $R^{1a}$ or $R^{1b}$ is ($O_2$—$C_6$)alkenyl is hydroborated to afford a compound of Formula I wherein $R^{1a}$ or $R^{1b}$ is hydroxy($C_2$-$C_6$)alkyl.

(7) a compound of Formula I, wherein $R^3$ is ($C_2$-$C_6$)alkenyl, is hydroborated to afford a compound of Formula I wherein $R^3$ is hydroxy($C_2$-$C_6$)alkyl.

(8) a compound of Formula I, wherein $R^{1a}$ or $R^{1b}$ is ($C_2$-$C_6$)alkenyl, can be reacted with osmium tetroxide and N-methylmorpholine-N-oxide to afford a compound of Formula I wherein $R^1$ is vicinal dihydroxy($C_2$-$C_6$)alkyl.

(9) a compound of Formula I, wherein $R^3$ is ($C_2$-$C_6$)alkenyl, can be reacted with osmium tetroxide and N-methylmorpholine-N-oxide to afford a vicinal diol compound of Formula I wherein $R^3$ is vicinal dihydroxy($C_2$-$C_6$)alkyl.

(10) a compound of Formula I, wherein $R^{1a}$ or $R^{1b}$ is ($C_2$-$C_6$)alkenyl, can be reacted with ozone followed by $NaBH_4$ to give a compound of Formula I wherein $R^{1a}$ or $R^{1b}$ is ω-hydroxy($C_1$-$C_5$)alkyl.

(11) a compound of Formula I, wherein $R^3$ is ($C_2$-$C_6$) alkenyl, can be reacted with ozone followed by $NaBH_4$ to give a compound of Formula I wherein $R^3$ is ω-hydroxy($C_1$-$C_5$) alkyl.

(12) a compound of Formula I wherein $R^{1a}$, $R^{1b}$ or $R^3$ is amino($C_1$-$C_6$)alkyl can be reacted with an ($C_1$-$C_6$)alkyl isocyanate to give a compound of Formula I wherein $R^{1a}$, $R^{1b}$ or $R^3$ is ($C_1$-$C_6$)alkylaminocarbonylamino($C_1$-$C_6$)alkyl.

(13) a compound of Formula I wherein $R^{1a}$, $R^{1b}$ or $R^3$ is amino($C_1$-$C_6$)alkyl can be reacted with an ($C_1$-$C_6$)alkyl chloroformate to give a compound of Formula I wherein $R^{1a}$, $R^{1b}$ or $R^3$ is ($C_1$-$C_6$)alkoxycarbonylamino($C_1$-$C_6$)alkyl.

(14) a compound of Formula I wherein $R^{1a}$, $R^{1b}$ or $R^3$ is amino($C_1$-$C_6$)alkyl can be reacted with chlorosulfonyl isocyanate or sulfamide to give a compound of Formula I wherein $R^{1a}$, $R^{1b}$ or $R^3$ is aminosulfonylamino($C_1$-$C_6$)alkyl.

(15) a compound of Formula I wherein $R^{1a}$, $R^{1b}$ or $R^3$ is amino($C_1$-$C_6$)alkyl can be reacted with a ($C_1$-$C_6$)alkylsulfamoyl chloride to give a compound of Formula I wherein $R^{1a}$, $R^{1b}$ or $R^3$ is ($C_1$-$C_6$)alkylaminosulfonylamino($C_1$-$C_6$)alkyl.

(16) a compound of Formula I wherein $R^{1a}$, $R^{1b}$ or $R^3$ is hydroxy($C_1$-$C_6$)alkyl can be reacted with chlorosulfonyl isocyanate to give a compound of Formula I wherein $R^{1a}$, $R^{1b}$ or $R^3$ is aminosulfonyloxy($C_1$-$C_6$)alkyl.

(17) a compound of Formula I wherein $R^{1a}$, $R^{1b}$ or $R^3$ is hydroxy($C_1$-$C_6$)alkyl can be reacted with p-nitrophenyl chloroformate, pentafluorophenyl chloroformate or carbonyl diimidazole, followed by ammonia, a ($C_1$-$C_6$)alkylamine or a di($C_1$-$C_6$)alkylamine to give a compound of Formula I wherein $R^{1a}$, $R^{1b}$ or $R^3$ is aminocarboxy($C_1$-$C_6$)alkyl, ($C_1$-$C_6$)alkyl aminocarboxy($C_1$-$C_6$)alkyl or di($C_1$-$C_6$)alkyl aminocarboxy($C_1$-$C_6$)alkyl.

(18) a compound of Formula I wherein $R^{1a}$, $R^{1b}$ or $R^3$ is hydroxy($C_1$-$C_6$)alkyl can be reacted with $POCl_3$ to give a compound of Formula I wherein $R^{1a}$, $R^{1b}$ or $R^3$ is $(HO)_2P(=O)O(C_1$-$C_6$)alkyl.

(19) a compound of Formula I, wherein $R^3$ is allyl or homoallyl can be reacted with oxygen in the presence of $PdCl_2$ and CuCl to afford a compound of Formula I, wherein $R^3$ is 2-oxopropyl or 3-oxobutyl respectively.

(20) a compound of Formula I, wherein $R^3$ is 2-oxopropyl or 3-oxobutyl can be reacted with MeMgX, wherein X is Cl, Br or I, to give a compound of Formula I, wherein $R^3$ is 2-hydroxy-2-methylpropyl or 3-hydroxy-3-methylpropyl respectively.

(21) a compound of Formula I, wherein $R^3$ is —$CH_2CO_2Me$ can be treated with MeMgX, wherein X is Cl, Br or I, to give a compound of Formula I, wherein $R^3$ is 2-hydroxy-2-methylpropyl.

(22) a compound of Formula I, wherein $R^3$ is allyl or —$CH_2C(Me)$=$CH_2$ can be hydrocyanated with TsCN in the presence of triphenylsilane and various cobalt catalysts to afford compounds of Formula I, wherein $R^3$ is —$CH_2CH(CN)Me$ or —$CH_2CMe_2CN$ respectively.

(23) a compound of Formula I, wherein $R^3$ is $CH_2C(Me)_2CN$, can be treated with acetamide in the presence of $PdCl_2$ to give a compound of Formula I, wherein $R^3$ is $CH_2CMe_2CONH_2$.

(24) a compound of Formula I, wherein $R^3$ is —$CH_2C(Me)$=$CH_2$ can be treated with m-CPBA followed by lithium triethylborohydride to afford a compound of Formula I, wherein $R^3$ is 2-hydroxy-2-methylpropyl.

Preparation 1

3-(2-methylbut-3-yn-2-yl)oxazolidin-2-one

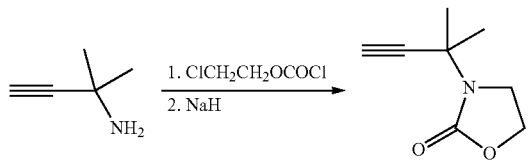

Step 1

A stirred solution of 1,1-dimethylpropargylamine (521 mg, 6.3 mmol) in MeCN (25 mL) was cooled in an ice bath and powdered K$_2$CO$_3$ (1.91 g, 13.8 mmol) was added. A solution of 2-chloroethyl chloroformate (0.68 mL, 6.6 mmol) in MeCN (10 mL) was added dropwise over 5 min. The cooling bath was allowed to melt and the mixture was stirred overnight at rt and then refluxed for 8 h. The mixture was concentrated and the residue was dissolved in EtOAc (100 mL), washed with water (15 mL) and brine (15 mL), and dried over Na$_2$SO$_4$. Removal of the solvent left crude 2-chloroethyl 2-methylbut-3-yn-2-ylcarbamate (1.05 g, 88%).

Step 2

Crude 2-chloroethyl 2-methylbut-3-yn-2-ylcarbamate (1.05 g, 5.5 mmol) was dissolved in dry THF (20 mL) and 60% NaH in oil (665 mg, 16.6 mmol) was added. The mixture was stirred under N$_2$ for 1 day and 5% aq HCl (25 mL) was added. The mixture was extracted with EtOAc (175 mL). The organic layer was washed with brine (25 mL) and dried over Na$_2$SO$_4$. Removal of the solvent left an oil (1.03 g) which was purified by chromatography on a 12-g cartridge eluted with a 0-80% EtOAc in hexanes gradient to afford 3-(2-methylbut-3-yn-2-yl)oxazolidin-2-one (567 mg, 67%) as a white solid. $^1$H NMR (CDCl$_3$) 1.72 (s, 6H), 2.43 (s, 1H), 3.74 (dd, 2H), 4.18 (dd, 2H).

Preparation 2

Butyl 2,2-dimethylbut-3-ynoate

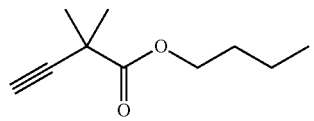

The title compound was prepared following the procedure described in Just, Z. W.; Larock, R. C. *J. Org. Chem.* 2008, 73, 2662-2667.

Preparation 3

1-(azetidin-1-yl)-2,2-dimethylbut-3-yn-1-one

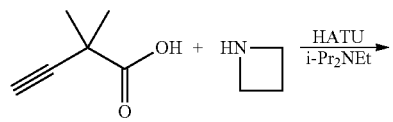

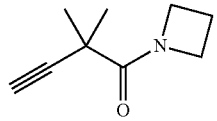

To a stirred solution of 1,1-dimethyl-3-butynoic acid (333 mg, 3.0 mmol), azetidine (250 mg, 4.5 mmol) and i-Pr$_2$NEt (1.6 mL, 8.9 mmol) in CH$_2$Cl$_2$ (20 mL) was added solid HATU (1.25 g, 3.3 mmol). The mixture was stirred at rt for 20 h and concentrated to leave a yellow oil. This oil was taken up in EtOAc (100 mL), washed with 5% aq HCl (2×15 mL), satd aq NaHCO$_3$ (15 mL) and brine (15 mL), and dried over Na$_2$SO$_4$. Removal of the solvent left an oil (819 mg) which was purified by chromatography on a 12-g silica cartridge, eluted with a 0-100% EtOAc in hexanes gradient, to afford 1-(azetidin-1-yl)-2,2-dimethylbut-3-yn-1-one (198 mg, 44%) as an oil. $^1$H NMR (CDCl$_3$) 1.40 (s, 6H), 2.23 (m, 2H), 2.34 (s, 1H), 4.05 (m, 2H), 4.52 (m, 2H).

Preparation 4

N-cyclopropyl-2,2-dimethylbut-3-ynamide

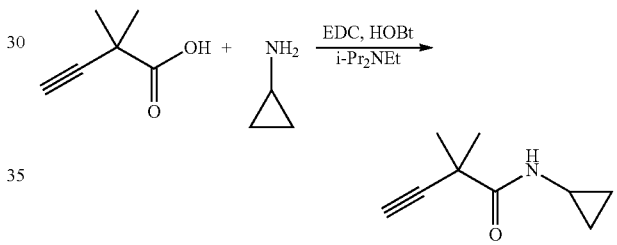

To a stirred solution of 1,1-dimethyl-3-butynoic acid (247 mg, 2.2 mmol), cyclopropylamine (0.23 mL, 3.3 mmol), HOBt.H$_2$O (506 mg, 3.3 mmol) and i-Pr$_2$NEt (1.2 mL, 6.6 mmol) in CH$_2$Cl$_2$ (10 mL) was added EDC.HCl (633 mg, 3.3 mmol). The mixture was stirred at rt for 18 h, diluted with ether (90 mL), washed with 5% aq HCl (15 mL) and satd aq NaHCO$_3$ (15 mL), and dried over Na$_2$SO$_4$. Removal of the solvent left N-cyclopropyl-2,2-dimethylbut-3-ynamide (187 mg, 56%). $^1$H NMR (CDCl$_3$) 0.53 (m, 2H), 0.79 (m, 2H), 1.44 (s, 6H), 2.45 (s, 1H), 2.73 (m, 1H), 6.76 (br s, 1H).

Preparation 5

N-(2-methylbut-3-yn-2-yl)cyclopropanecarboxamide

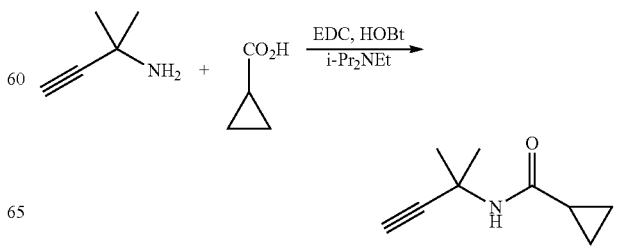

The title compound was prepared from 2-methylbut-3-yn-2-amine and cyclopropanecarboxylic acid following the procedure described in Preparation 4.

Preparation 6

4-ethynyltetrahydro-2H-pyran-4-ol

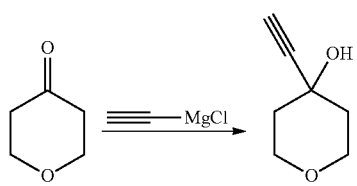

A stirred solution of dihydro-2H-pyran-4(3H)-one (500 mg, 5.0 mmol) in dry THF (20 mL) was cooled to −70° C. and 0.5 M ethynylmagnesium chloride in THF (20 mL, 10 mmol) was added in a slow stream. The cooling bath was allowed to expire and the mixture was stirred as it warmed to rt. After 6 h, satd aq NH₄Cl (20 mL) was added and the mixture was concentrated on the rotary evaporator. The aqueous residue was extracted with EtOAc (2×50 mL). The combined organic extracts were washed with brine, dried over Na₂SO₄ and concentrated to leave crude 4-ethynyltetrahydro-2H-pyran-4-ol (491 mg, 78%) as a brown oil. $^1$H NMR (CDCl$_3$) 1.80 (m, 2H), 1.92 (m, 2H), 2.57 (s, 1H), 3.68 (m, 2H), 3.90 (m, 2H).

Preparation 7 tert-Butyl 3-ethynyl-3-hydroxyazetidine-1-carboxylate

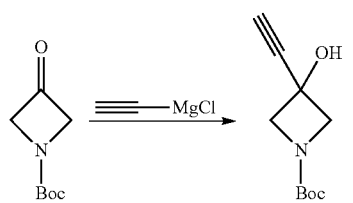

The title compound was prepared from tert-butyl 3-oxoazetidine-1-carboxylate following a procedure analogous to that described in Preparation 6. $^1$H NMR (CDCl$_3$) 1.42 (s, 9H), 2.66 (s, 1H), 4.05 (d, 2H), 4.19 (d, 2H).

Preparation 8

(S)-3-((S)-1-(4-bromophenyl)ethyl)-6-(2-hydroxy-2-methylpropyl)-6-phenyl-1,3-oxazinan-2-one Method 1

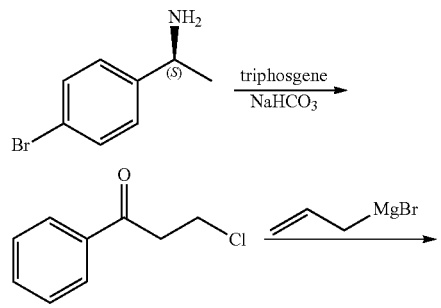

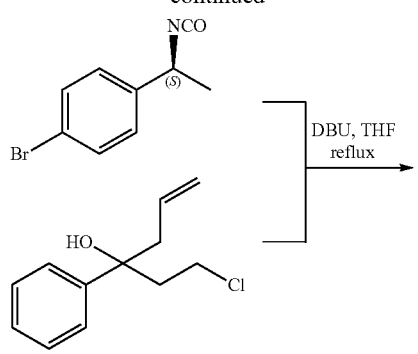

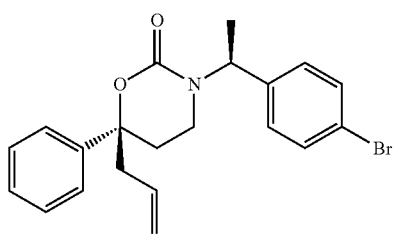

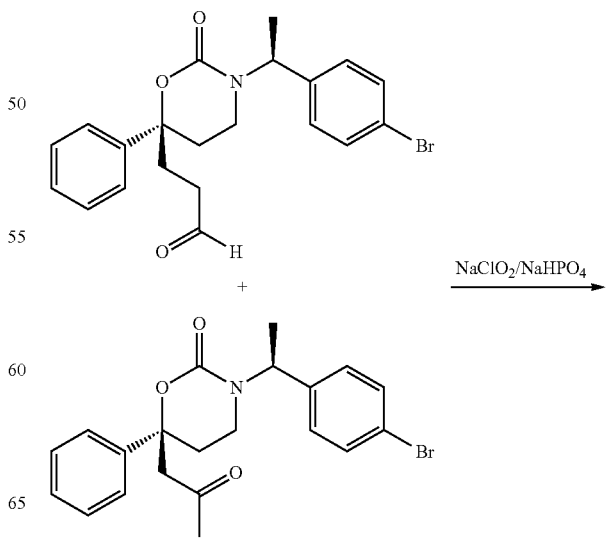

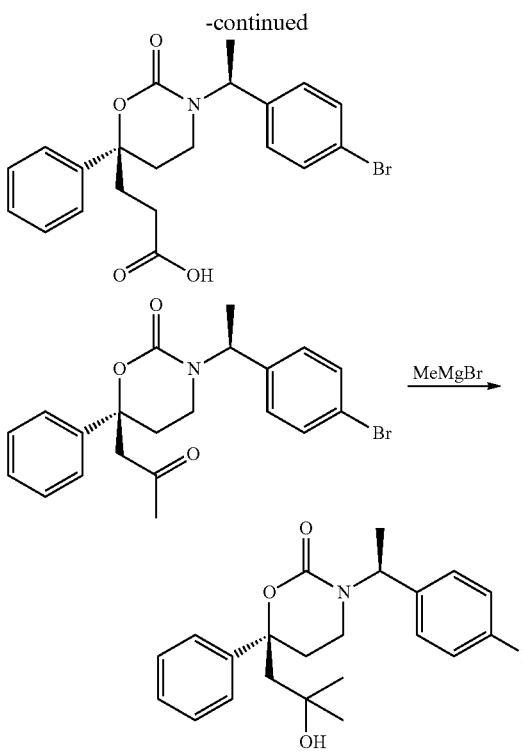

Step 1

(S)-1-bromo-4-(1-isocyanatoethyl)benzene

To a solution of (S)-1-(4-bromophenyl)ethanamine (240 g, 1.2 mol) in methylene chloride (3 L) and satd aq NaHCO$_3$ (3 L) solution was added triphosgene (118 g, 0.396 mol) at 0° C. The mixture was stirred for 15 min. The organic phase was separated, dried over Na$_2$SO$_4$ and concentrated to give 1-bromo-4-(1-isocyanato-ethyl)-benzene (170 g, 63%).

Step 2

1-chloro-3-phenylhex-5-en-3-ol

To a solution of 3-chloro-1-phenylpropan-1-one (170 g, 1.01 mol) in anhydrous THF (1200 mL) was added allylmagnesium bromide (1.2 L, 1 mol/L) at −78° C. under nitrogen. The formed mixture was stirred for 30 min at −78° C. The reaction was quenched with aqueous NaHCO$_3$ solution. The organic phase was separated, dried over Na$_2$SO$_4$ and concentrated to give the crude product, which was purified by column chromatography (petroleum ether/EtOAc=100:1) to afford 1-chloro-3-phenylhex-5-en-3-ol (180 g, 86%). $^1$H NMR (CDCl$_3$): 2.27 (m, 2H), 2.51 (m, 1H), 2.74 (m, 1H), 3.22 (m, 1H), 3.58 (m, 1H), 5.16 (m, 2H), 5.53 (m, 1H), 7.23 (m, 1H), 7.39 (m, 4H).

Step 3

(R)-6-allyl-3-((S)-1-(4-bromophenyl)ethyl)-6-phenyl-1,3-oxazinan-2-one

A mixture of 1-chloro-3-phenyl-hex-5-en-3-ol (105 g, 0.050 mmol), (S)-(−)-1-(-bromophenyl)ethyl isocyanate (170 g, 0.752 mol), and DBU (228 g, 1.5 mol) in THF (1700 mL) was heated to reflux overnight. The mixture was diluted with EtOAc and washed with 1N aq HCl. The aqueous phase was extracted with EtOAc (3×). The combined organic phase was dried over Na$_2$SO$_4$. After the solvents were evaporated, the crude product was purified by column chromatography (petroleum ether/EtOAc=20:1 to 5:1) to give (R)-6-allyl-3-((S)-1-(4-bromophenyl)ethyl)-6-phenyl-1,3-oxazinan-2-one (100 g, 34%). $^1$H NMR (CDCl$_3$): 1.39 (d, 3H), 2.14 (m, 1H), 2.24 (m, 2H), 2.48-2.61 (m, 3H), 2.82 (m, 2H), 5.01 (m, 2H), 5.52 (q, 1H), 5.73 (m, 1H), 6.62 (d, 2H), 7.12 (m, 2H), 7.28 (m, 2H).

Step 4

(S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal To a solution of (R)-6-allyl-3-((S)-1-(4-bromophenyl) ethyl)-6-phenyl-1,3-oxazinan-2-one (31 g, 78 mmol) and CuCl (19.3 g, 195 mmol) in dry DMF (150 mL) was added H$_2$O (50 mL) and PdCl$_2$ (4.10 g, 23 mmol) at rt. After addition, the mixture was stirred overnight under oxygen. After TLC showed the starting material had disappeared, the solid was filtered off. Water (200 mL) and EtOAc (200 mL) was added, the organic layers were separated and the aqueous layer was extracted with EtOAc (3×40 mL). The combined organic layer was washed with brine, dried over Na$_2$SO$_4$, filtered and concentrated to give a residue which was purified by column chromatography (petroleum ether/EtOAc=5:1 to 1:1) to give a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal, (26 g, 81%).

Step 5

(S)-3-((S)-1-(4-bromophenyl)ethyl)-6-(2-oxopropyl)-6-phenyl-1,3-oxazinan-2-one

To a mixture of (S)-3-((S)-1-(4-bromophenyl)ethyl)-6-(2-oxopropyl)-6-phenyl-1,3-oxazinan-2-one and 3-((R)-3-((S)-1-(4-bromophenyl)ethyl)-2-oxo-6-phenyl-1,3-oxazinan-6-yl)propanal (20 g, 48.2 mmol) in t-BuOH (250 mL) and 2-methyl-2-butene (50 mL) was added a solution of NaClO$_2$ (19.3 g, 0.213 mol) and NaH$_2$PO$_4$ (28 g, 0.179 mol) in H$_2$O (300 mL) at 0° C. The formed mixture was stirred for 1 h at 0° C. The mixture was treated with water (100 mL) and extracted with CH$_2$Cl$_2$. The combined organic layer was dried over Na$_2$SO$_4$, filtered and concentrated to leave a residue, which was purified by column chromatography (petroleum ether/EtOAc=5:1 to 2.5:1) to afford (S)-3-((S)-1-(4-bromophenyl)ethyl)-6-(2-oxopropyl)-6-phenyl-1,3-oxazinan-2-one (10.0 g, 83%). $^1$H NMR (CDCl$_3$): 1.49 (d, 3H), 2.12 (s, 3H), 2.33 (m, 2H), 2.63 (m, 1H), 2.86-3.08 (m, 3H), 5.57 (q, 1H), 6.66 (d, 2H), 7.19 (m, 2H), 7.33 (m, 5H).

Step 6

(S)-3-((S)-1-(4-bromophenyl)ethyl)-6-(2-hydroxy-2-methylpropyl)-6-phenyl-1,3-oxazinan-2-one To a solution of (S)-3-((S)-1-(4-bromophenyl)ethyl)-6-(2-oxopropyl)-6-phenyl-1,3-oxazinan-2-one (20 g, 46.4 mmol) in anhydrous THF (200 mL) was added dropwise methylmagnesium bromide (31 mL, 144 mmol) at −78° C. under nitrogen. Then the mixture was stirred at rt for 1 h. The reaction mixture was quenched with aq NaHCO₃ (50 mL) under ice water bath. The organic layers were separated. The aqueous layer was extracted with EtOAc (150 mL). The combined organic layers were washed with brine, dried over Na₂SO₄ and concentrated in vacuo to give the crude product, which was purified column chromatography (petroleum ether/EtOAc=5:1 to 2:1) to afford (S)-3-((S)-1-(4-bromophenyl)ethyl)-6-(2-hydroxy-2-methylpropyl)-6-phenyl-1,3-oxazinan-2-one (13 g, 65%). After re-crystallization from EtOH, 4 g of the pure compound was obtained. ¹H NMR (CDCl₃): 1.06 (s, 3H), 1.12 (s, 3H), 1.44 (d, 3H), 2.14 (m, 3H), 2.21 (m, 1H), 2.33 (m, 1H), 2.76 (m, 1H), 5.54 (q, 1H), 6.74 (d, 2H), 7.16 (d, 2H), 7.28 (m, 5H).

Alternative Procedure for Method 1 Step 2

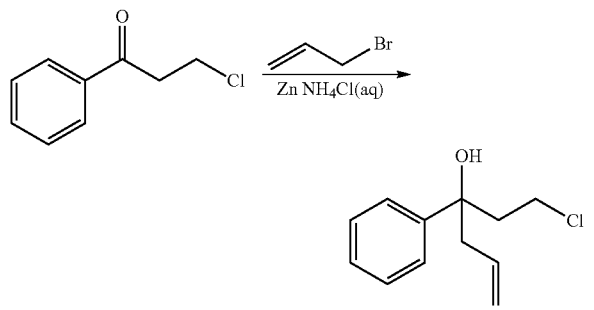

A solution of 3-chloro-1-phenylpropan-1-one (100 g, 0.595 mol) in THF (280 ml) was added dropwise to a well-stirred mixture of zinc powder (need not be activated) (40 g, 1.231 mol, satd aq NH₄Cl solution (1500 ml) and THF (400 ml). Allyl bromide (143 g, 1.19 mol) was dissolved in THF (200 ml) was slowly added to the reaction mixture. The reaction was mildly exothermic, and the mixture began to reflux spontaneously. After refluxing had ceased, the mixture was stirred for 1 h. The mixture was extracted with EtOAc, dried over anhydrous Na₂SO₄, and concentrated to give 1-chloro-3-phenylhex-5-en-3-ol (122 g, 97%). ¹H NMR: (400 MHz, CDCl₃): δ=2.24 (s, 1H), 2.34 (m, 2H), 2.53 (m, 1H), 2.75 (m, 1H), 3.20 (m, 1H), 3.58 (m, 1H), 5.18 (t, 1H), 5.51 (m, 1H), 7.26 (m, 1H), 7.26-7.39 (m, 3H).

(R)-6-allyl-3-((S)-1-(4-bromophenyl)propyl)-6-phenyl-1,3-oxazinan-2-one was prepared from (S)-1-(4-bromophenyl)propan-1-amine following procedures analogous to those described in Preparation 1 Method 1 Steps 1 to 3 above.

(S)-3-((S)-1-(4-bromophenyl)ethyl)-6-(4-fluorophenyl)-6-(2-hydroxy-2-methylpropyl)-1,3-oxazinan-2-one was prepared from (R)-6-allyl-3-((S)-1-(4-bromophenyl)ethyl)-6-(4-fluorophenyl)-1,3-oxazinan-2-one following procedures analogous to those described in Preparation 1 Method 1 Steps 4 and 6.

Method 2

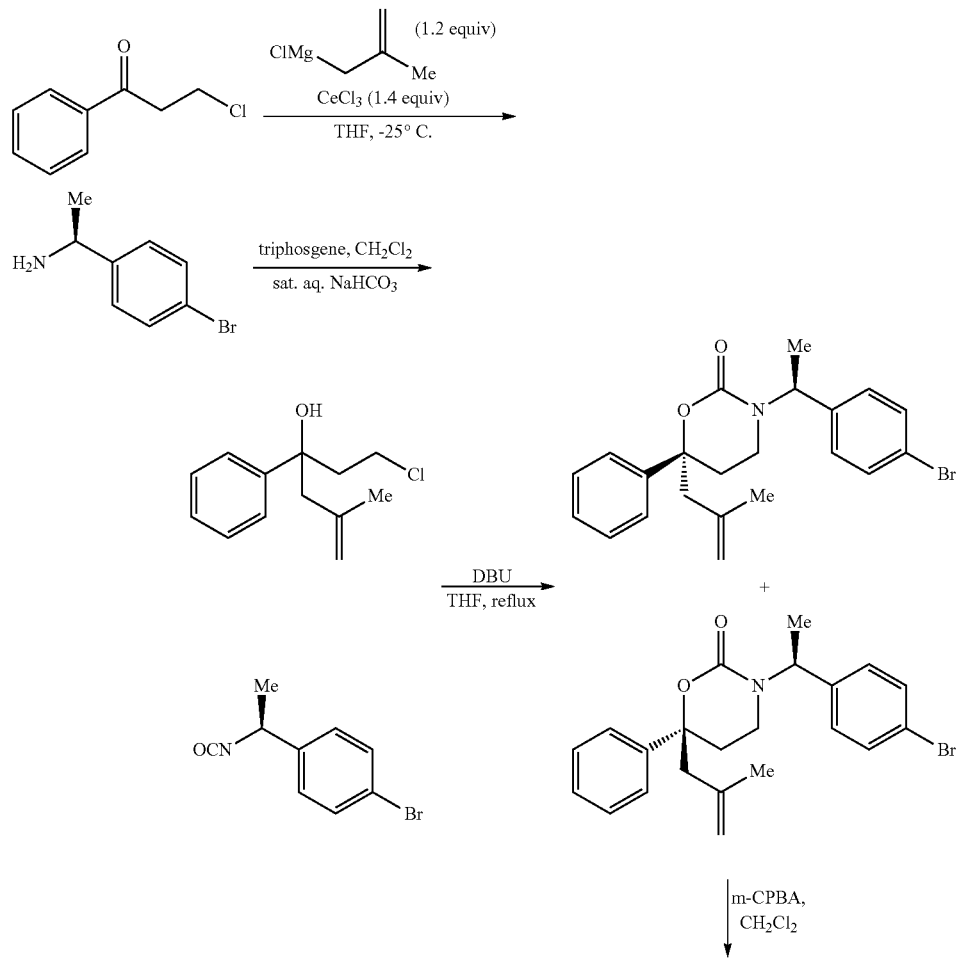

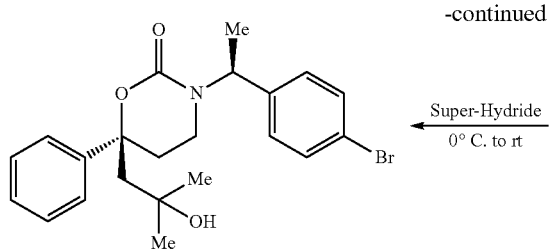 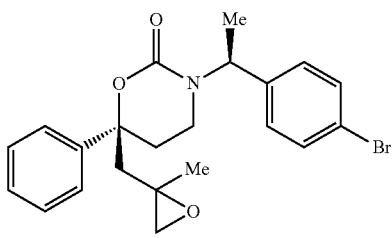

-continued

Super-Hydride
0° C. to rt

Step 1

1-Chloro-5-methyl-3-phenyl-hex-5-en-3-ol

To a stirred suspension of magnesium turnings (46.7 g, 1.94 mol) in 1500 mL of THF ($H_2O$<100 ppm based on Karl Fischer titration) was charged 53.0 mL of 1 M DIBAL-H in hexane under nitrogen at rt. Then 3-chloro-2-methylprop-1-ene (160 g, 1.77 mol) was introduced while maintaining the internal temperature below 30° C. The resulting solution was agitated for 2 h at rt. The solution was titrated in the presence of 1.1'-bipyridine to indicate 0.8 M of the corresponding Grignard reagent. To a dry flask containing 307.0 g of anhydrous $CeCl_3$ (1.25 mol) at rt under nitrogen was added 1556.8 mL of the Grignard reagent (0.8 M, 1.25 mol). The resulting slurry was cooled to −10° C. and agitated for 0.5 h. To the slurry was added 200 g of 3-chloro-1-phenylpropan-1-one (1.19 mol) in 200 mL of THF while maintaining the internal temperature below 0° C. After the mixture was stirred for 0.5 h, 1200 mL of 1 M aq HCl was added to obtain a clear solution while maintaining the internal temperature below 30° C. After the phase cut, the aqueous layer was extracted with EtOAc (500 mL). The combined organic layers were washed with brine and dried over sodium sulfate. Removal of the solvent under vacuum produced crude 1-chloro-5-methyl-3-phenyl-hex-5-en-3-ol, which was chased with THF to achieve $H_2O$<500 ppm based on Karl Fischer titration. The crude product (306 g, 83 wt %, 95% yield) was used directly in Step 3. $^1$H-NMR spectroscopy (500 MHz, $CDCl_3$) δ 7.38-7.37 (d. J=7.8 Hz, 2H), 7.33 (t, J=7.9 Hz, 2H), 7.24 (t, J=7.4 Hz, 1H), 4.91 (s, 1H), 4.76 (s, 1H), 3.57 (ddd, J=5.6, 10.7, and 10.7, 1H), 3.13 (ddd, J=4.7, 10.7 and 10.7 Hz, 1H), 2.66 (d, J=13.3 Hz, 1H), 2.54 (d, J=11.3 Hz, 1H), 2.53 (s, 1H), 2.36 (ddd, J=5.4, 10.6 and 13.9 Hz. 1H), 2.29 (ddd, J=5.6, 11.3 and 13.3 Hz, 1H), 1.29 (s, 3H). $^{13}$C-NMR spectroscopy (125 MHz, $CDCl_3$) δ 144.3, 141.4, 128.0, 126.6, 124.8, 116.1, 74.2, 51.2, 46.0, 39.9, 23.9.

Step 2

1-Bromo-4-((S)-1-isocyanato-ethyl)-benzene

To a 10 L jacketed reactor was charged 241 g of sodium bicarbonate (2.87 mol, 2.30 equiv) and 5 L of deionized water. The resulting solution was agitated for 10-20 min, until the solids dissolved (homogeneous). To the clear solution was charged 250 g (1.25 mol, 1.00 equiv) of (S)-(−)-1-(4-bromophenyl)ethylamine as a solution in 1.00 L of dichloromethane. An additional 4 L of dichloromethane was charged to the reactor. The biphasic solution was agitated and cooled to $T_{int}$=2-3° C. Triphosgene (126 g, 424 mmol, 0.340 equiv) was charged to the reactor in approximately two equal portions ~6 min apart. It should be noted that a slight exotherm was noted upon the addition of triphosgene. The resulting murky solution was agitated at $T_{int}$=2-5° C. for 30 min, at which point HPLC analysis indicates >99 A % conversion (220 nm). The dichloromethane layer was cut and dried with anhydrous sulfate. The resulting solution was passed through a celite plug and concentrated to ~1.5 L which fine particles of a white solid developed. The solution was filtered and concentrated to a thick oil via reduced pressure to produce 239 g of 1-bromo-4-((S)-1-isocyanato-ethyl)-benzene (93.7 wt %, 79.4% yield). $^1$H-NMR spectroscopy (400 MHz, $CD_2Cl_2$) δ 7.53 (d, J=11.4 Hz, 2H), 7.26 (d, J=8.2 Hz, 2H), 4.80 (q, J=6.7 Hz, 1H), 1.59 (d, J=6.7 Hz, 3H). The material was used in Step 3 without further purification.

Step 3

(R)-3-((S)-1-(4-bromophenyl)ethyl)-6-(2-methylallyl)-6-phenyl-1,3-oxazinan-2-one To a dried 10 L jacketed reactor under a nitrogen atmosphere was charged 1-chloro-5-methyl-3-phenyl-hex-5-en-3-ol (167 g, 81.7 wt %, 610 mmol, 1.00 equiv), 1-bromo-4-((S)-1-isocyanato-ethyl)-benzene (219 g, 93.7 wt %, 911 mmol, 1.50 equiv), anhydrous tetrahydrofuran (3.00 L), and then 1,8-diazabicyclo[5.4.0]undec-7-ene (DBU, 409 mL, 2.73 mol, 4.50 equiv). The resulting solution was agitated and refluxed ($T_{int}$=67-69° C., $T_{ext}$=75° C.) for 19 h, at which point HPLC analysis indicated ~1A % (220 nm) of the 1-chloro-5-methyl-3-phenyl-hex-5-en-3-ol remained. The dark solution was cooled to $T_{int}$=20-25° C. Two liters of tetrahydrofuran were removed by distillation under reduced pressure. The remaining dark solution was diluted with 4.0 L of ethyl acetate and 1.0 L of hexanes. The resulting solution was washed with 4.0 L of a 1.0 M aqueous solution of hydrogen chloride (note: the wash is slightly exothermic). The aqueous solution was cut and the remaining organic solution was dried with anhydrous sodium sulfate, filtered and then concentrated to an oil via reduced pressure. The resulting material was subjected to flash silica chromatography (5-30% ethyl acetate/hexanes, 1.74 kg of silica) to produce 137.8 g of material (59 wt %, 3.1:1 diastereomeric ratio favoring the desired diastereomer (R)-3-((S)-1-(4-bromophenyl)ethyl)-6-(2-methylallyl)-6-phenyl-1,3-oxazinan-2-one, 32.3% yield). The material was used in Step 4 without further purification.

Analytical data for (R)-3-((S)-1-(4-bromophenyl)ethyl)-6-(2-methylallyl)-6-phenyl-1,3-oxazinan-2-one: $^1$H-NMR spectroscopy (500 MHz, $CD_2Cl_2$) δ 7.42-7.35 (m, 3H), 7.33-7.31 (m, 2H), 7.25-7.23 (m, 2H), 6.80-6.74 (m, 2), 5.55 (q, J=7.1 Hz, 1H), 5.37-5.36 (m, 1H), 4.89 (s, 1H), 4.69 (s, 1H), 2.96-2.93 (m, 1H), 2.61 (dd, J=13.8 and 26.4 Hz, 2H), 2.37-2.25 (m, 3H), 1.68 (s, 3H), 1.50 (d, J=7.1 Hz, 3H). $^{13}$C-NMR spectroscopy (125 MHz, $CD_2Cl_2$) δ 152.5, 141.5, 140.1, 138.3, 130.6, 128.1, 128.0, 126.9, 124.4, 120.2, 115.3, 82.4, 52.1, 50.1, 35.6, 29.8, 23.4, 14.5.

Analytical data for (S)-3-((S)-1-(4-bromophenyl)ethyl)-6-(2-methylallyl)-6-phenyl-1,3-oxazinan-2-one: $^1$H-NMR spectroscopy (400 MHz, CD$_2$Cl$_2$) δ 7.50-7.48 (m, 2H), 7.43-7.39 (m, 2H), 7.35-7.32 (m, 3H), 7.20-7.18 (m, 2H), 5.60 (q, J=7.1 Hz, 1H), 4.85 (s, 1H), 4.66 (s, 1H), 2.73-2.67 (m, 2H), 2.60 (dd, J=13.9 and 19.4 Hz, 2H), 2.28 (dt, J=3.3 and 13.7 Hz, 1H), 2.14-2.05 (m, 1H), 1.66 (s, 3H), 1.24 (d, J=7.2 Hz, 3H). $^{13}$C-NMR spectroscopy (100 MHz, CD$_2$Cl$_2$) δ 153.4, 142.5, 141.0, 140.1, 131.8, 129.3, 128.9, 127.8, 125.3, 121.5, 116.3, 83.9, 53.2, 51.0, 36.6, 31.3, 24.3, 15.4.

Step 4

(6S)-3-((S)-1-(4-bromophenyl)ethyl)-6-((2-methyloxiran-2-yl)methyl)-6-phenyl-1,3-oxazinan-2-one To a 1.0 L 2-neck RBF was charged (R)-3-((S)-1-(4-bromophenyl)ethyl)-6-(2-methylallyl)-6-phenyl-1,3-oxazinan-2-one (135.8 g, 59 wt %, 3.1:1 dr, 193 mmol, 1.00 equiv), dichloromethane (700 mL), and then 3-chloroperbenzoic acid (m-CPBA, 70%, 95.3 g, 386 mmol, 2.0 equiv). The resulting solution was agitated at rt (T$_{int}$=20-25° C.) for 1 h, which HPLC analysis indicates >99 A % (220 nm) conversion. The resulting solution was diluted with 700 mL of methyl tert-butyl ether (MTBE) and washed with 1×500 mL of 30 wt % solution of sodium thiosulfate and 1×500 mL of saturated aqueous solution of sodium bicarbonate. The wash sequence was repeated until the peak on an HPLC trace of the organic solution that corresponds to a HPLC sample peak of m-CPBA is <2.5 A % (220 nm), which in this example the wash sequence was repeated 3 times. The resulting organic layer was dried with anhydrous sodium sulfate, filtered and then concentrated to an oil via reduced pressure. The resulting material was diluted with 200 mL of anhydrous tetrahydrofuran and then concentrated to a thick oil via reduced pressure to provide (6S)-3-((S)-1-(4-bromophenyl)ethyl)-6-((2-methyloxiran-2-yl)methyl)-6-phenyl-1,3-oxazinan-2-one which was used directly in Step 5.

Step 5

(S)-3-((S)-1-(4-bromophenyl)ethyl)-6-(2-hydroxy-2-methylpropyl)-6-phenyl-1,3-oxazinan-2-one To a 2.0 L 3-neck oven-dried RBF was charged the crude (6S)-3-((S)-1-(4-bromophenyl)ethyl)-6-((2-methyloxiran-2-yl)methyl)-6-phenyl-1,3-oxazinan-2-one and 750 mL of anhydrous THF. The resulting solution was agitated and cooled to T$_{int}$=2-3° C. To the agitated clear solution was charged 1.0 M lithium triethylborohydride in tetrahydrofuran (Super Hydride, 348 mL, 348 mmol, 1.8 equiv). The addition is exothermic and addition was controlled to maintain T$_{int}$=<8° C. The resulting solution was agitated at T$_{int}$=2-3° C. for 1.5 h and then allowed to warm to T$_{int}$=10-13° C. over a 2.5 h, which HPLC analysis indicates ~94 A % (220 nm) conversion. To the agitated solution was charged a solution of hydrogen peroxide (95.7 mL of a 35 wt % aqueous solution diluted with 400 mL of water, 1.08 mol, 5.60 equiv). The addition is highly exothermic and addition was controlled to maintain T$_{int}$=<25° C. The resulting solution was diluted with 1.00 L of methyl tert-butyl ether (MTBE) and washed with 1.00 L of water followed by 500 mL of a ~30 wt % solution of sodium thiosulfate. The organic solution was dried with anhydrous sodium sulfate, filtered, and then concentrated via reduced pressure. The resulting material was subjected to flash silica chromatography (10-60% ethyl acetate, 600 g of silica) to produce 68 g of material consisting of both diastereomers (1.98:1 dr) and 41 g of the desired diastereomer (>99:1 dr). The material consisting of the mixed fractions was recrystallized from 250 mL of isopropyl acetate (IPAC) and 200 mL of heptane (anti-solvent) to produce upon filtration 31.3 g of product (95.7 A % at 220 nm, 74:1 dr). The two samples were combined to produce 72.3 g of (S)-3-((S)-1-(4-bromophenyl)ethyl)-6-(2-hydroxy-2-methylpropyl)-6-phenyl-1,3-oxazinan-2-one (83.6% yield for the two step operation). $^1$H-NMR spectroscopy (400 MHz, CDCl$_3$) δ 7.37-7.29 (m, 5H), 7.25-7.21 (m, 2H), 6.82-6.79 (m, 2H), 5.61 (q, J=6.9 Hz, 1H), 2.83 (ddd, J=2.5, 5.4 and 11.6 Hz, 1H), 2.39 (ddd, J=5.7, 12.0 and 14.1 Hz, 1H), 2.27 (ddd, J=2.6, 4.8 and 14.0 Hz, 1H), 2.21-2.14 (m, 3H), 2.08 (s, 1H), 1.49 (d, J=7.0 Hz, 3H), 1.18 (s, 3H), 1.13 (s, 3H). $^{13}$C-NMR spectroscopy (100 MHz, CDCl$_3$) δ 153.2, 142.6, 138.5, 131.6, 129.13, 129.10, 128.0, 125.3, 121.6, 84.2, 71.4, 54.1, 53.3, 36.4, 33.6, 32.1, 30.8, 15.6.

LC-MS Methods

Method 1: Agilent 1200

| Column | Waters Xbridge C18 30 × 4.6 mm, 2.5 µm | |
|---|---|---|
| Mobile Phase | A: water + 0.1% F$_3$CCO$_2$H B: acetonitrile | |
| | TIME (min) | A % | B % |
| | 0 | 90 | 10 |
| | 0.15 | 90 | 10 |
| | 3.15 | 10 | 90 |
| | 4.50 | 10 | 90 |
| | 4.75 | 20 | 10 |
| | 5.00 | 20 | 10 |
| Flow Rate | 1.2 mL/min | |
| Wavelength | UV 220, 230, or 254 nm | |

Example 1

(S)-6-(2-hydroxy-2-methylpropyl)-3-((S)-1-(4-(3-hydroxy-3-methylbut-1-ynyl)phenyl)ethyl)-6-phenyl-1,3-oxazinan-2-one

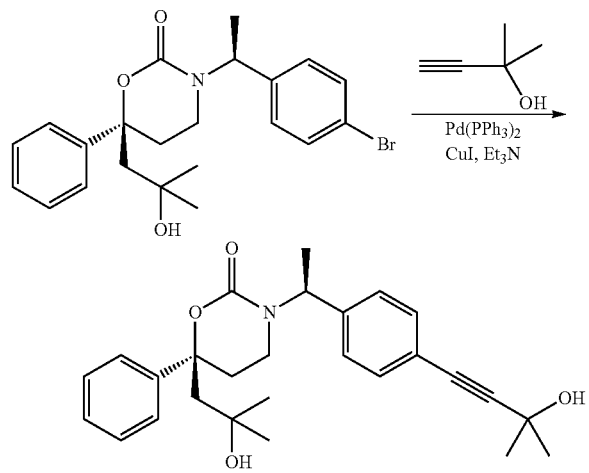

A microwave vial was charged with (S)-3-((S)-1-(4-bromophenyl)ethyl)-6-(2-hydroxy-2-methylpropyl)-6-phenyl-1,3-oxazinan-2-one (216 mg, 0.50 mmol), 3-hydroxy-3-methyl-1-butyne (0.24 mL, 2.50 mmol), CuI (9.5 mg, 0.05 mmol) and Et$_3$N (4 mL). The mixture was sparged with N$_2$ for 5 min and PdCl$_2$(PPh$_3$)$_2$ (21 mg, 0.03 mmol) was added. The mixture was sparged with N₂ for 5 min and heated at 100° C. for 2 h in the microwave. The mixture was diluted with EtOAc (200 mL), washed with 5% aq HCl (2×30 mL), satd aq NaHCO₃ (30 mL) and brine (30 mL), and dried over Na₂SO₄. Removal of the solvent left a dark oil (379 mg) which was applied to a 2 g silica SPE Cartridge. The cartridge was eluted with 0, 25, 50 and 75% EtOAc in hexanes (20 mL) of each and EtOAc (2×20 mL) to give six fractions. Fractions 4 and 5 were pooled and concentrated to afford the title compound (193 mg, 89%) as an oil. LC-MS Method 1 $t_R$=1.53 min, m/z=436, 378; ¹H NMR (CDCl₃) 1.12 (s, 3H), 1.18 (s, 3H), 1.52 (d, 3H), 1.60 (s, 6H), 2.15 (m, 1H), 2.19 (s, 2H), 2.20-2.45 (2H), 2.80 (m, 1H), 5.66 (q, 1H), 6.86 (d, 2H), 7.17 (d, 2H), 7.30-7.40 (5H)

Example 2

(S)-6-(2-hydroxy-2-methylpropyl)-3-((S)-1-(4-((1-hydroxycyclopentyl)ethynyl)phenyl)ethyl)-6-phenyl-1,3-oxazinan-2-one

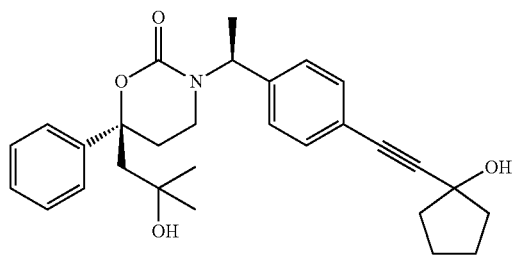 [SMILES: C[C@@H](c1ccc(C#CC2(O)CCCC2)cc1)N1CC[C@](CC(C)(C)O)(c2ccccc2)OC1=O]

The title compound was prepared following a procedure analogous to that described in Example 1 using 1-ethynylcyclopentanol. LC-MS Method 1 $t_R$=1.68 min, m/z=462, 404; ¹H NMR (CD₃OD) 0.93 (s, 3H), 1.25 (s, 3H), 1.48 (d, 3H), 1.80 (4H), 1.95 (4H), 2.13 (s, 2H), 2.20 (m, 1H), 2.44 (2H), 2.98 (m, 1H), 5.52 (q, 1H), 6.87 (d, 2H), 7.12 (d, 2H), 7.30-7.40 (5H)

Example 3

(S)-6-(2-hydroxy-2-methylpropyl)-3-((S)-1-(4-(3-methyl-3-(2-oxooxazolidin-3-yl)but-1-ynyl)phenyl)ethyl)-6-phenyl-1,3-oxazinan-2-one

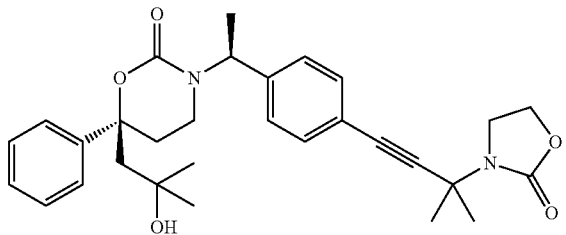 [SMILES: C[C@@H](c1ccc(C#CC(C)(C)N2CCOC2=O)cc1)N1CC[C@](CC(C)(C)O)(c2ccccc2)OC1=O]

The title compound was prepared following a procedure analogous to that described in Example 1 using 3-(2-methylbut-3-yn-2-yl)oxazolidin-2-one. LC-MS Method 1 $t_R$=1.6 min, m/z=527, 447; ¹H NMR (CDCl₃) 1.12 (s, 3H), 1.18 (s, 3H), 1.51 (d, 3H), 1.78 (6H), 2.10-2.40 (5H), 2.82 (m, 1H), 3.77 (dd, 2H), 4.27 (dd, 2H), 5.66 (q, 1H), 6.88 (d, 2H), 7.17 (d, 2H), 7.30-7.40 (5H))

Example 4

4-(4-((S)-1-((S)-6-(2-hydroxy-2-methylpropyl)-2-oxo-6-phenyl-1,3-oxazinan-3-yl)ethyl)phenyl)-2,2-dimethylbut-3-ynoic acid

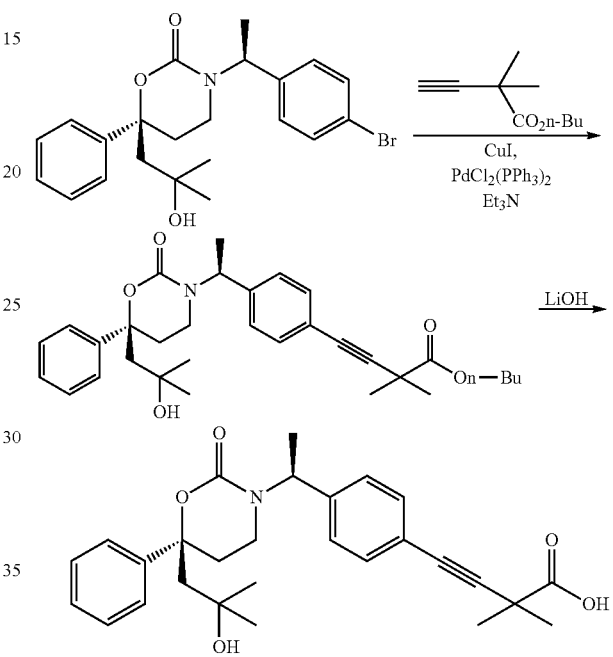

Step 1

A microwave vial was charged with (S)-3-((S)-1-(4-bromophenyl)ethyl)-6-(2-hydroxy-2-methylpropyl)-6-phenyl-1,3-oxazinan-2-one (50 mg, 0.12 mmol), butyl 2,2-dimethylbut-3-ynoate (40 mg, 0.23 mmol), CuI (2.2 mg, 0.012 mmol), PdCl₂(PPh₃)₂ (5 mg, 0.008 mmol), Et₃N (2 mL) and Et₂NH (0.2 mL). The mixture was sparged with N₂ for 10 min and heated at 100 C for 2 h. The mixture was concentrated, redissolved in EtOAc (90 mL), washed with 5% aq HCl (20 mL) and brine (20 mL), and dried over Na₂SO₄. Removal of the solvent left an oil (75 mg) which was purified by prep HPLC to afford butyl 4-(4-((S)-1-((S)-6-(2-hydroxy-2-methylpropyl)-2-oxo-6-phenyl-1,3-oxazinan-3-yl)ethyl)phenyl)-2,2-dimethylbut-3-ynoate (11 mg, 19%). LC-MS Method 1 $t_R$=2.13 min, m/z=520, 462.

Step 2

To a stirred solution of butyl 4-(4-((S)-1-((S)-6-(2-hydroxy-2-methylpropyl)-2-oxo-6-phenyl-1,3-oxazinan-3-yl)ethyl)phenyl)-2,2-dimethylbut-3-ynoate (11.3 mg, 0.022 mmol) in 1:1:2 THF/H₂O/MeOH (2 mL) was added LiOH.H₂O (60 mg, 1.4 mmol). The mixture was stirred at rt for 1 day and concentrated. The residue was purified by prep HPLC to afford 4-(4-((S)-1-((S)-6-(2-hydroxy-2-methylpropyl)-2-oxo-6-phenyl-1,3-oxazinan-3-yl)ethyl)phenyl)-2,2-dimethylbut-3-ynoic acid (7 mg, 72%) as a solid. LC-MS Method 1 $t_R$=1.58 min, m/z=464, 406; ¹H NMR (CDCl₃) 1.12

(s, 3H), 1.18 (s, 3H), 1.51 (d, 3H), 1.58 (s, 6H), 2.10-2.40 (5H), 2.90 (m, 1H), 5.67 (q, 1H), 6.86 (d, 2H), 7.18 (d, 2H), 7.30-7.40 (5H).

Example 5

4-(4-((S)-1-((S)-6-(2-hydroxy-2-methylpropyl)-2-oxo-6-phenyl-1,3-oxazinan-3-yl)ethyl)phenyl)-N,N,2,2-tetramethylbut-3-ynamide

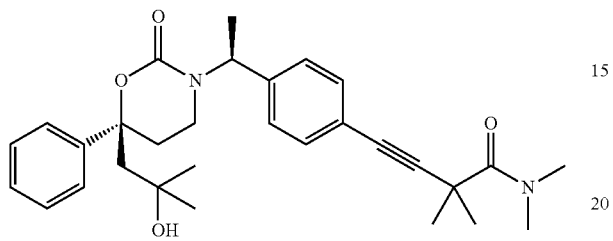 [SMILES: C[C@@H](c1ccc(C#CC(C)(C)C(=O)NC2CC2)cc1)N1CC[C@](CC(C)(C)O)(c2ccccc2)OC1=O]

To a stirred solution of 4-(4-((S)-1-((S)-6-(2-hydroxy-2-methylpropyl)-2-oxo-6-phenyl-1,3-oxazinan-3-yl)ethyl)phenyl)-2,2-dimethylbut-3-ynoic acid (5.0 mg, 0.011 mmol) and i-Pr2NEt (0.01 mL) in CH$_2$Cl$_2$ (1 mL) were added 2 M Me$_2$NH in THF (0.1 mL, 0.2 mmol) and solid HATU (8.5 mg, 0.022 mmol). The mixture was stirred overnight at rt, concentrated and the residue purified by prep HPLC to afford 4-(4-((S)-1-((S)-6-(2-hydroxy-2-methylpropyl)-2-oxo-6-phenyl-1,3-oxazinan-3-yl)ethyl)phenyl)-N,N,2,2-tetramethylbut-3-ynamide (1.0 mg, 19%). LC-MS Method 1 t$_R$=1.65 min, m/z=491, 433; $^1$H NMR (CDCl$_3$) 1.13 (s, 3H), 1.18 (s, 3H), 1.52 (d, 3H), 1.55 (s, 6H), 2.10-2.40 (5H), 2.82 (m, 1H), 5.64 (q, 1H), 6.88 (d, 2H), 7.13 (d, 2H), 7.30-7.40 (5H)

Example 6

(S)-3-((S)-1-(4-(4-(azetidin-1-yl)-3,3-dimethyl-4-oxobut-1-ynyl)phenyl)ethyl)-6-(2-hydroxy-2-methylpropyl)-6-phenyl-1,3-oxazinan-2-one

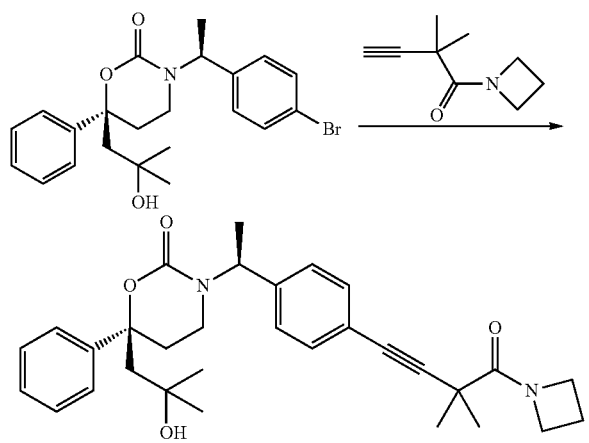

A microwave vial equipped with a stir bar was charged with (S)-3-((S)-1-(4-bromophenyl)ethyl)-6-(2-hydroxy-2-methylpropyl)-6-phenyl-1,3-oxazinan-2-one (51 mg, 0.12 mmol), 1-(azetidin-1-yl)-2,2-dimethylbut-3-yn-1-one (35 mg, 0.24 mmol), Pd(OAc)$_2$ (2.6 mg, 0.1 mmol), tri(ortho-tolyl)phosphine (7.2 mg, 0.2 mmol) and powdered K$_2$CO$_3$ (32.6 mg, 0.24 mmol). The vial was capped and flushed with N$_2$. Water (0.1 mL) and toluene (1 mL) were added and the mixture was heated in a 100° C. oil bath for 18 h. The reaction mixture was applied to a 10-mL ChemElut cartridge, which had been prewetted with water (5 mL), and eluted with EtOAc (40 mL). The eluate was concentrated to leave an amber solid (72 mg) which was purified by prep HPLC to afford (S)-3-((S)-1-(4-(4-(azetidin-1-yl)-3,3-dimethyl-4-oxobut-1-ynyl)phenyl)ethyl)-6-(2-hydroxy-2-methylpropyl)-6-phenyl-1,3-oxazinan-2-one (35 mg, 60%) as a white solid. LC-MS Method 1 t$_R$=1.62 min, m/z=503, 445; $^1$H NMR (CDCl$_3$) 1.12 (s, 3H), 1.18 (s, 3H), 1.46 (s, 6H), 1.50 (d, 3H), 2.10-2.45 (5H0, 2.70-2.90 (2H), 4.08 (m, 2H), 4.53 (m, 2H), 5.65 (q, 1H), 6.90 (d, 2H), 7.14 (d, 2H), 7.30-7.40 (5H).

Example 7

N-cyclopropyl-4-(4-((S)-1-((S)-6-(2-hydroxy-2-methylpropyl)-2-oxo-6-phenyl-1,3-oxazinan-3-yl)ethyl)phenyl)-2,2-dimethylbut-3-ynamide

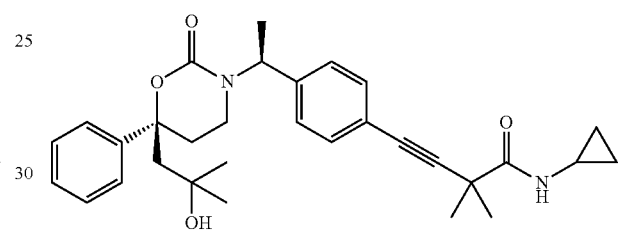

The title compound was prepared following a procedure analogous to that described in Example 1 using N-cyclopropyl-2,2-dimethylbut-3-ynamide. LC-MS Method 1 t$_R$=1.63 min, m/z=503, 445; $^1$H NMR (CDCl$_3$) 0.52 (m, 2h), 0.80 (m, 2H), 1.13 (s, 3H), 1.19 (s, 3H), 1.48 (s, 6H), 1.53 (d, 3H), 2.18 (m, 1H), 2.22 (s, 2H), 2.25-2.45 (2H), 2.72 (m, 1H), 2.84 (m, 1H), 5.66 (q, 1H), 6.92 (d, 2H), 7.17 (d, 2H), 7.30-7.40 (5H).

Example 8

N-(4-(4-((S)-1-((S)-6-(2-hydroxy-2-methylpropyl)-2-oxo-6-phenyl-1,3-oxazinan-3-yl)ethyl)phenyl)-2-methylbut-3-yn-2-yl)cyclopropanecarboxamide

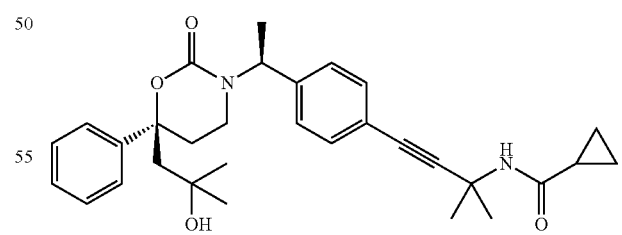

The title compound was prepared following a procedure analogous to that described in Example 1 using N-(2-methylbut-3-yn-2-yl)cyclopropanecarboxamide. LC-MS Method 1 t$_R$=1.6 min, m/z=503, 445; $^1$H NMR (CDCl$_3$) 0.72 (m, 2H), 0.95 (m, 2H), 1.12 (s, 3H), 1.18 (s, 3H), 1.30 (m, 1H), 1.51 (d, 3H), 1.68 (s, 6H), 2.15 (m, 1H), 2.21 (s, 2H), 2.25-2.40 (2H), 2.78 (m, 1H), 5.63 (q, 1H), 6.84 (d, 2H), 7.17 (d, 2H), 7.25-7.40 (5H).

Example 9

(S)-6-(2-hydroxy-2-methylpropyl)-6-phenyl-3-((S)-1-(4-(pyridin-2-ylethynyl)phenyl)ethyl)-1,3-oxazinan-2-one

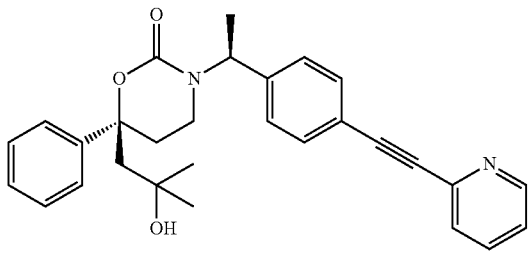 [SMILES: C[C@@H](c1ccc(C#Cc2ccccn2)cc1)N1CC[C@](CC(C)(C)O)(c2ccccc2)OC1=O]

The title compound was prepared following a procedure analogous to that described in Example 1 using 2-ethynylpyridine. LC-MS Method 1 $t_R$=1.58 min, m/z=455, 397; $^1$H NMR (CDCl$_3$) 1.14 (s, 3H), 1.19 (s, 3H), 1.51 (d, 3H), 2.15 (m, 1H), 22.20 (s, 2H), 2.27 (m, 1H), 2.39 (m, 1H), 2.83 (m, 1H), 6.67 (q, 1H), 6.92 (d, 2H), 7.25-7.40 (8H), 7.53 (d, 1H), 7.71 (m, 1H), 8.64 (d, 1H).

Example 10

(S)-6-(2-hydroxy-2-methylpropyl)-3-((S)-1-(4-((4-hydroxytetrahydro-2H-pyran-4-yl)ethynyl)phenyl)ethyl)-6-phenyl-1,3-oxazinan-2-one

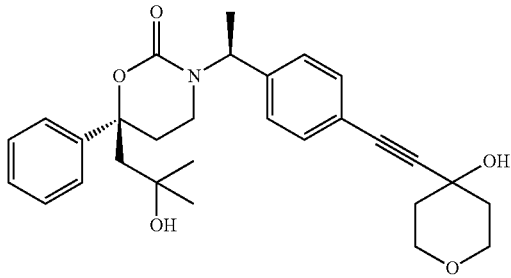 [SMILES: C[C@@H](c1ccc(C#CC2(O)CCOCC2)cc1)N1CC[C@](CC(C)(C)O)(c2ccccc2)OC1=O]

The title compound was prepared following a procedure analogous to that described in Example 1 using 4-ethynyltetrahydro-2H-pyran-4-ol. LC-MS Method 1 $t_R$=1.4 min, m/z=478, 420; $^1$H NMR (CDCl$_3$) 1.12 (s, 3H), 1.19 (s, 3H), 1.50 (d, 3H), 1.87 (m, 2H), 2.00 (m, 2H), 2.10-2.30 (4H), 2.38 (m, 1H), 2.81 (m, 1H), 3.70 (m, 2H), 3.96 (m, 2H), 5.66 (q, 1H), 6.88 (d, 2H), 7.18 (d, 2H), 7.30-7.40 (5H).

Example 11

(S)-3-((S)-1-(4-((4-hydroxy-1-methylpiperidin-4-yl)ethynyl)phenyl)ethyl)-6-(2-hydroxy-2-methylpropyl)-6-phenyl-1,3-oxazinan-2-one

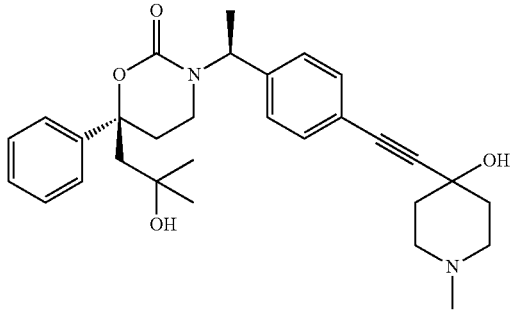 [SMILES: C[C@@H](c1ccc(C#CC2(O)CCN(C)CC2)cc1)N1CC[C@](CC(C)(C)O)(c2ccccc2)OC1=O]

The title compound was prepared following a procedure analogous to that described in Example 1 using 4-ethynyl-1-methylpiperidin-4-ol. LC-MS Method 1 $t_R$=1.05 min, m/z=491.

Example 12

(S)-3-((S)-1-(4-(3-amino-3-methylbut-1-ynyl)phenyl)ethyl)-6-(2-hydroxy-2-methylpropyl)-6-phenyl-1,3-oxazinan-2-one

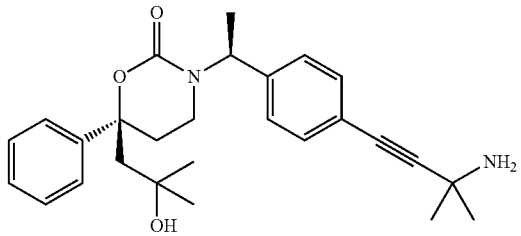 [SMILES: C[C@@H](c1ccc(C#CC(C)(C)N)cc1)N1CC[C@](CC(C)(C)O)(c2ccccc2)OC1=O]

The title compound was prepared following a procedure analogous to that described in Example 1 using 2-methylbut-3-yn-2-amine. LC-MS Method 1 $t_R$=1.12 min, m/z=435; $^1$H NMR (CD$_3$OD) 0.95 (s, 3H), 1.25 (s, 3H), 1.52 (d, 3H), 1.68 (s, 6H), 2.15 (s, 2H), 2.19 (m, 1H), 2.47 (m, 2H), 3.03 (m, 1H), 5.52 (q, 1H), 6.93 (d, 2H), 7.20 (d, 2H), 7.25-7.40 (5H).

Example 13

(S)-3-((S)-1-(4-((1-aminocyclohexyl)ethynyl)phenyl)ethyl)-6-(2-hydroxy-2-methylpropyl)-6-phenyl-1,3-oxazinan-2-one

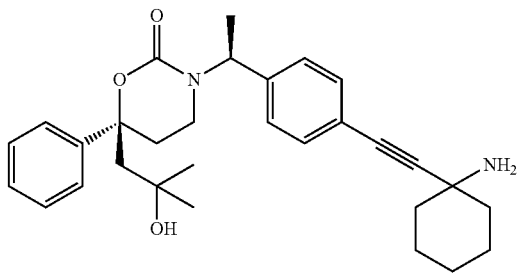 [SMILES: C[C@@H](c1ccc(C#CC2(N)CCCCC2)cc1)N1CC[C@](CC(C)(C)O)(c2ccccc2)OC1=O]

The title compound was prepared following a procedure analogous to that described in Example 1 using 1-ethynylcyclohexanamine. LC-MS Method 1 $t_R$=1.23 min, m/z=475; $^1$H NMR (CD$_3$OD) 0.94 (s, 3H), 1.25 (s, 3H), 1.51 (d, 3H), 1.65-1.90 (8H), 2.10-2.25 (4H), 2.18 (m, 1H), 2.48 (m, 2H), 3.02 (m, 1H), 5.53 (q, 1H), 6.94 (d, 2H), 7.22 (d, 2H), 7.25-7.40 (5H).

Example 14

N-(1-((4-((S)-1-((S)-6-(2-hydroxy-2-methylpropyl)-2-oxo-6-phenyl-1,3-oxazinan-3-yl)ethyl)phenyl)ethynyl)cyclohexyl)acetamide

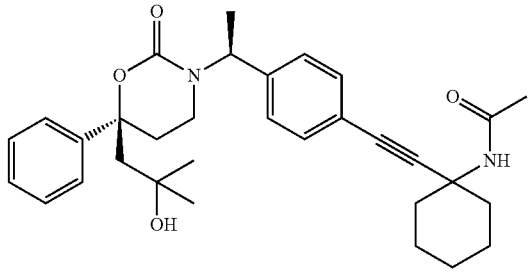 [SMILES: CC(=O)NC1(C#Cc2ccc([C@H](C)N3CC[C@](CC(C)(C)O)(c4ccccc4)OC3=O)cc2)CCCCC1]

A vial equipped with a flea stir bar was charged with (S)-3-((S)-1-(4-((1-aminocyclohexyl)ethynyl)phenyl)ethyl)-6-(2-hydroxy-2-methylpropyl)-6-phenyl-1,3-oxazinan-2-one (12 mg, 0.025 mmol), i-Pr₂NEt (0.015 mL, 0.08 mmol) and CH₂Cl₂ (2 mL). Acetic anhydride (0.005 mL, 0.043 mmol) was added. The mixture was stirred overnight at rt and evaporated to dryness. The residue was purified by prep HPLC to afford the title compound (6.1 mg, 47%). LC-MS Method 1 $t_R$=1.65 min, m/z=517, 459; ¹H NMR (CDCl₃) 1.12 (s, 3H), 1.18 (s, 3H), 1.30 (m, 1H), 1.51 (d, 3H), 1.65 (m, 6H), 1.87 (m, 2H), 1.99 (s, 3H), 2.14 (m, 3H), 2.21 (s, 2H), 2.35 (m, 1H), 2.78 (m, 1H), 5.65 (q, 1H), 6.88 (d, 2H), 7.18 (d, 2H), 7.30-7.40 (5H)

Example 15

Methyl 1-((4-((S)-1-((S)-6-(2-hydroxy-2-methylpropyl)-2-oxo-6-phenyl-1,3-oxazinan-3-yl)ethyl)phenyl)ethynyl)cyclohexylcarbamate

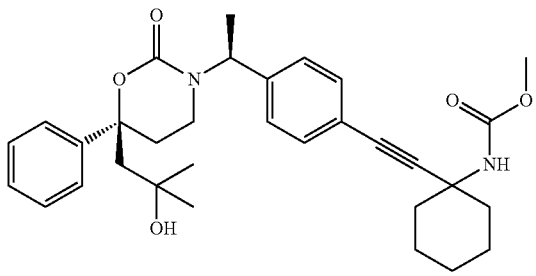 [SMILES: COC(=O)NC1(C#Cc2ccc([C@H](C)N3CC[C@](CC(C)(C)O)(c4ccccc4)OC3=O)cc2)CCCCC1]

The title compound was prepared following a procedure analogous to that described in Example 15 using methyl chloroformate. LC-MS Method 1 $t_R$=1.85 min, m/z=533, 475; ¹H NMR (CDCl₃) 1.12 (s, 3H), 1.19 (s, 3H), 1.31 (m, 1H), 1.50 (d, 3H), 1.62 (m, 6H), 1.78 (m, 2H), 2.12 (m, 3H), 2.20 (s, 2H), 2.38 (m, 1H), 2.78 (m, 1H), 3.66 (s, 3H), 4.88 (s, 1H), 5.64 (q, 1H), 6.86 (d, 2H), 7.18 (d, 2H), 7.25-7.40 (5H).

Example 16

1-(1-((4-((S)-1-((S)-6-(2-hydroxy-2-methylpropyl)-2-oxo-6-phenyl-1,3-oxazinan-3-yl)ethyl)phenyl)ethynyl)cyclohexyl)urea

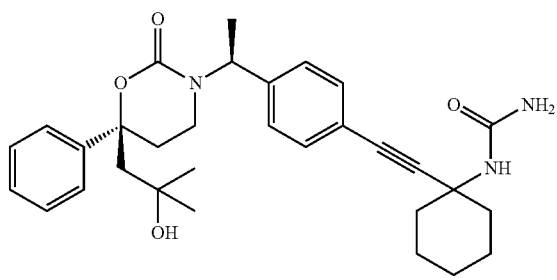 [SMILES: C[C@@H](c1ccc(C#CC2(NC(N)=O)CCCCC2)cc1)N1CC[C@](CC(C)(C)O)(c2ccccc2)OC1=O]

The title compound was prepared following a procedure analogous to that described in Example 15 using trimethylsilyl isocyanate. LC-MS Method 1 $t_R$=1.6 min, m/z=503, 400; ¹H NMR (CDCl₃) [selected resonances] 1.12 (s, 3H), 1.18 (s, 3H), 1.33 (m, 1H), 1.48 (d, 3H), 1.81 (m, 2H), 2.20 (s, 2H), 2.37 (m, 1H), 2.79 (m, 1H), 5.61 (q, 1H), 6.84 (d, 2H), 7.14 (d, 2H).

Example 17

N-(4-(4-((S)-1-((S)-6-(2-hydroxy-2-methylpropyl)-2-oxo-6-phenyl-1,3-oxazinan-3-yl)ethyl)phenyl)-2-methylbut-3-yn-2-yl)acetamide

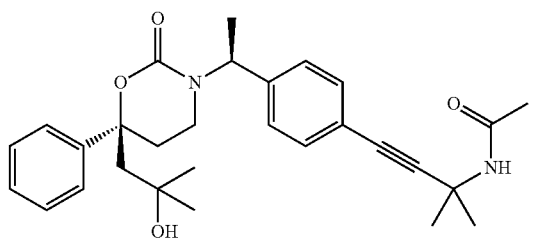 [SMILES: CC(=O)NC(C)(C)C#Cc1ccc([C@H](C)N2CC[C@](CC(C)(C)O)(c3ccccc3)OC2=O)cc1]

The title compound was prepared following a procedure analogous to that described in Example 15 using (S)-3-((S)-1-(4-(3-amino-3-methylbut-1-ynyl)phenyl)ethyl)-6-(2-hydroxy-2-methylpropyl)-6-phenyl-1,3-oxazinan-2-one. LC-MS Method 1 $t_R$=1.45 min, m/z=477, 419; ¹H NMR (CDCl₃) 1.11 (s, 3H), 1.19 (s, 3H), 1.48 (d, 3H), 1.67 (s, 6H), 1.99 (s, 3H), 2.14 (m, 1H), 2.21 (s, 2H), 2.20-2.40 (2H), 2.78 (m, 1H), 5.64 (q, 1H), 6.86 (d, 2H), 7.17 (d, 2H), 7.30-7.40 (5H)

Example 18 methyl 4-(4-((S)-1-((S)-6-(2-hydroxy-2-methylpropyl)-2-oxo-6-phenyl-1,3-oxazinan-3-yl)ethyl)phenyl)-2-methylbut-3-yn-2-ylcarbamate

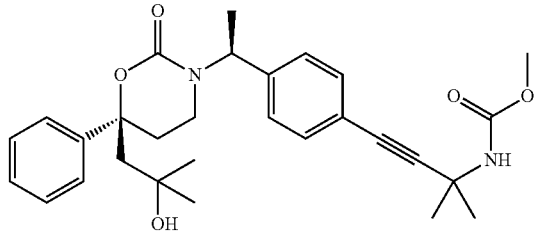 [SMILES: COC(=O)NC(C)(C)C#Cc1ccc([C@H](C)N2CC[C@](CC(C)(C)O)(c3ccccc3)OC2=O)cc1]

The title compound was prepared following a procedure analogous to that described in Example 15 using (S)-3-((S)-1-(4-(3-amino-3-methylbut-1-ynyl)phenyl)ethyl)-6-(2-hydroxy-2-methylpropyl)-6-phenyl-1,3-oxazinan-2-one and methyl chloroformate. LC-MS Method 1 $t_R$=1.65 min, m/z=493, 435; ¹H NMR (CDCl₃) 1.12 (s, 3H), 1.18 (s, 3H), 1.49 (d, 3H), 1.67 (s, 6H), 2.14 (m, 1H), 2.21 (s, 2H), 2.25-2.40 (2H), 2.78 (m, 1H), 5.65 (q, 1H), 6.88 (d, 2H), 7.17 (d, 2H), 7.30-7.40 (5H).

Example 19

1-(4-(4-((S)-1-((S)-6-(2-hydroxy-2-methylpropyl)-2-oxo-6-phenyl-1,3-oxazinan-3-yl)ethyl)phenyl)-2-methylbut-3-yn-2-yl)urea

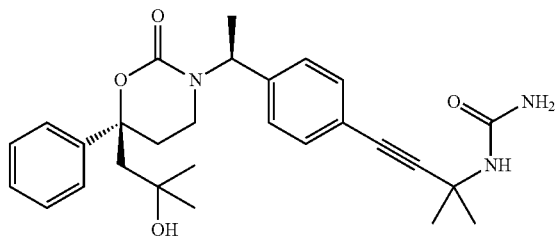 [SMILES: C[C@@H](c1ccc(C#CC(C)(C)NC(N)=O)cc1)N1CC[C@](CC(C)(C)O)(c2ccccc2)OC1=O]

The title compound was prepared following a procedure analogous to that described in Example 15 using (S)-3-((S)-1-(4-(3-amino-3-methylbut-1-ynyl)phenyl)ethyl)-6-(2-hydroxy-2-methylpropyl)-6-phenyl-1,3-oxazinan-2-one and trimethylsilyl isocyanate. LC-MS Method 1 $t_R$=1.43 min, m/z=463; $^1$H NMR (CDCl$_3$) 1.12 (s, 3H), 1.18 (s, 3H), 1.47 (d, 3H), 1.67 (s, 6H), 2.10-2.30 (4H), 2.38 (m, 1H), 2.77 (m, 1H), 5.58 (q, 1H), 6.78 (d, 1H), 7.08 (d, 1H), 7.30-7.40 (5H).

Example 20

1-(4-(4-((S)-1-((S)-6-(2-hydroxy-2-methylpropyl)-2-oxo-6-phenyl-1,3-oxazinan-3-yl)ethyl)phenyl)-2-methylbut-3-yn-2-yl)-3-methylurea

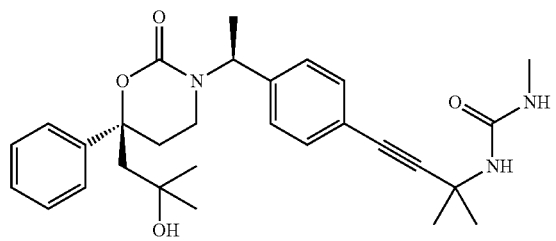 [SMILES: CNC(=O)NC(C)(C)C#Cc1ccc([C@H](C)N2CC[C@](CC(C)(C)O)(c3ccccc3)OC2=O)cc1]

The title compound was prepared following a procedure analogous to that described in Example 15 using (S)-3-((S)-1-(4-(3-amino-3-methylbut-1-ynyl)phenyl)ethyl)-6-(2-hydroxy-2-methylpropyl)-6-phenyl-1,3-oxazinan-2-one and methyl isocyanate. LC-MS Method 1 $t_R$=1.45 min, m/z=492, 434; $^1$H NMR (CDCl$_3$) 1.13 (s, 3H), 1.19 (s, 3H), 1.49 (d, 3H), 1.64 (s, 6H), 2.10-2.50 (5H), 2.81 (m, 1H), 2.82 (s, 3H), 5.66 (q, 1H), 6.88 (d, 2H), 7.17 (d, 2H), 7.30-7.40 (5H).

Example 21

N-(4-(4-((S)-1-((S)-6-(2-hydroxy-2-methylpropyl)-2-oxo-6-phenyl-1,3-oxazinan-3-yl)ethyl)phenyl)-2-methylbut-3-yn-2-yl)methanesulfonamide

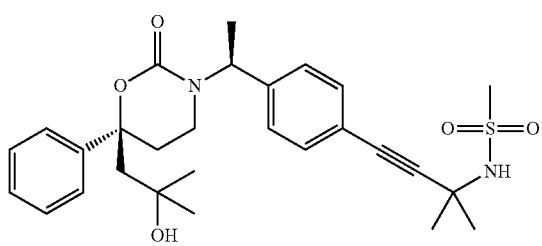 [SMILES: C[C@@H](c1ccc(C#CC(C)(C)NS(C)(=O)=O)cc1)N1CC[C@](CC(C)(C)O)(c2ccccc2)OC1=O]

The title compound was prepared following a procedure analogous to that described in Example 15 using (S)-3-((S)-1-(4-(3-amino-3-methylbut-1-ynyl)phenyl)ethyl)-6-(2-hydroxy-2-methylpropyl)-6-phenyl-1,3-oxazinan-2-one and methanesulfonyl chloride. LC-MS Method 1 $t_R$=1.53 min, m/z=513, 455; $^1$H NMR (CDCl$_3$) 1.13 (s, 3H), 1.18 (s, 3H), 1.49 (d, 3H), 1.69 (s, 6H), 2.10-2.45 (5H), 2.83 (m, 1H), 3.14 (s, 3H), 5.66 (q, 1H), 6.92 (d, 2H), 7.17 (d, 2H), 7.30-7.40 (5H)

Example 22

N-(2-methyl-4-(4-((S)-1-((R)-6-(2-methylallyl)-2-oxo-6-phenyl-1,3-oxazinan-3-yl)ethyl)phenyl)but-3-yn-2-yl)methanesulfonamide

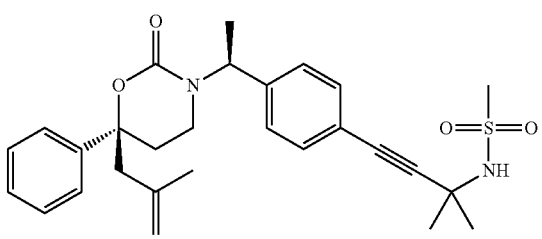 [SMILES: C=C(C)C[C@]1(c2ccccc2)CCN([C@@H](C)c2ccc(C#CC(C)(C)NS(C)(=O)=O)cc2)C(=O)O1]

The title compound was isolated as a byproduct from the procedure used to prepare Example 21. LC-MS Method 1 $t_R$=1.84 min, m/z=495; $^1$H NMR (CDCl$_3$) 1.50 (d, 3H), 1.64 (s, 3H0, 1.68 (s, 6H), 2.15-2.35 (m, 3H), 2.53 (d, 1H), 2.61 (d, 1H), 2.88 (m, 1H), 3.16 (s, 3H), 4.47 (s, 1H), 4.65 (s, 1H), 4.85 (s, 1H), 5.62 (q, 1H), 6.75 9d, 2H), 7.11 (d, 2H), 7.30-7.40 (5H).

Example 23

3-(4-(4-((S)-1-((S)-6-(2-hydroxy-2-methylpropyl)-2-oxo-6-phenyl-1,3-oxazinan-3-yl)ethyl)phenyl)-2-methylbut-3-yn-2-yl)-1,1-dimethylurea

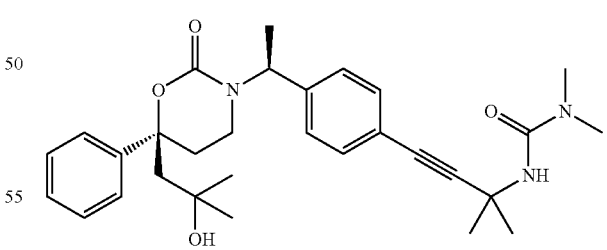

The title compound was prepared following a procedure analogous to that described in Example 15 using (S)-3-((S)-1-(4-(3-amino-3-methylbut-1-ynyl)phenyl)ethyl)-6-(2-hydroxy-2-methylpropyl)-6-phenyl-1,3-oxazinan-2-one and dimethylcarbamyl chloride with the addition of DMAP. LC-MS Method 1 $t_R$=1.53 min, m/z=506, 448; $^1$H NMR (CDCl$_3$) 1.12 (s, 3H), 1.19 (s, 3H), 1.48 (d, 3H), 1.71 (s, 6H), 2.10-2.40 (5H), 2.78 (m, 1H), 2.91 (s, 6H), 5.63 (q, 1H), 6.86 (d, 2H), 7.18 (d, 2H), 7.30-7.40 (5H).

Example 24

(S)-6-(2-hydroxy-2-methylpropyl)-3-((S)-1-(4-((3-hydroxyazetidin-3-yl)ethynyl)phenyl)ethyl)-6-phenyl-1,3-oxazinan-2-one

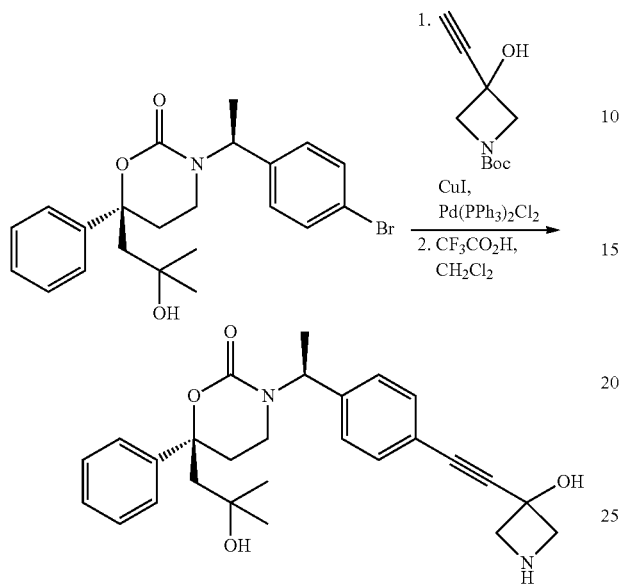

Step 1
tert-butyl 3-hydroxy-3-((4-((S)-1-((S)-6-(2-hydroxy-2-methylpropyl)-2-oxo-6-phenyl-1,3-oxazinan-3-yl)ethyl)phenyl)ethynyl)azetidine-1-carboxylate was prepared following a procedure analogous to that described in Example 1 using tert-butyl 3-ethynyl-3-hydroxyazetidine-1-carboxylate.

Step 2
To an ice-cold, stirred solution of tert-butyl 3-hydroxy-3-((4-((S)-1-((S)-6-(2-hydroxy-2-methylpropyl)-2-oxo-6-phenyl-1,3-oxazinan-3-yl)ethyl)phenyl)ethynyl)azetidine-1-carboxylate (97 mg, mmol) in CH$_2$Cl$_2$ (4 mL) and CF$_3$CO$_2$H (1 mL) was added. The mixture was stirred in the ice bath for 0.5 h and concentrated to leave an amber oil (137 mg) which was purified by prep HPLC to afford the title compound as its TFA salt (29 mg, 29%). LC-MS Method 1 t$_R$=1.03 min, m/z=449; $^1$H NMR (CD$_3$OD) 0.96 (s, 3H), 1.27 (s, 3H), 1.51 (d, 3H), 2.14 (s, 2H), 2.19 (m, 1H), 2.46 (m, 2H), 3.03 (m, 1H), 4.14 (d, 2H), 4.37 (d, 2H), 5.53 (q, 1H), 6.94 (d, 2H), 7.23 (d, 2H), 7.25-7.40 (5H)

Example 25

(S)-3-((S)-1-(4-((1-acetyl-3-hydroxyazetidin-3-yl)ethynyl)phenyl)ethyl)-6-(2-hydroxy-2-methylpropyl)-6-phenyl-1,3-oxazinan-2-one

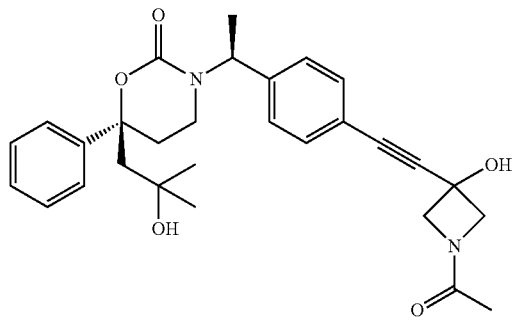 [SMILES: CC(=O)N1CC(O)(C#Cc2ccc([C@H](C)N3CC[C@](CC(C)(C)O)(c4ccccc4)OC3=O)cc2)C1]

The title compound was prepared from (S)-6-(2-hydroxy-2-methylpropyl)-3-((S)-1-(4-((3-hydroxyazetidin-3-yl)ethynyl)phenyl)ethyl)-6-phenyl-1,3-oxazinan-2-one and acetic anhydride following a procedure analogous to that described in Example 14. LC-MS Method 1 t$_R$=1.27 min, m/z=491, 433; $^1$H NMR (CDCl$_3$) 1.12 (s, 3H), 1.18 (s, 3H), 1.52 (d, 3H), 1.97 (s, 3H), 2.15-2.45 (5H), 2.84 (m, 1H), 4.20 (d, 1H), 4.36 (m, 2h), 4.44 (d, 1H), 5.65 (q, 1H), 6.88 (d, 2H), 7.17 (d, 2H), 7.30-7.40 (5H).

Example 26

Methyl 3-hydroxy-3-((4-((S)-1-((S)-6-(2-hydroxy-2-methylpropyl)-2-oxo-6-phenyl-1,3-oxazinan-3-yl)ethyl)phenyl)ethynyl)azetidine-1-carboxylate

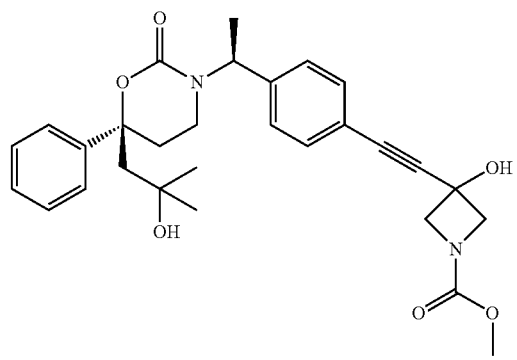 [SMILES: COC(=O)N1CC(O)(C#Cc2ccc([C@H](C)N3CC[C@](CC(C)(C)O)(c4ccccc4)OC3=O)cc2)C1]

The title compound was prepared from (S)-6-(2-hydroxy-2-methylpropyl)-3-((S)-1-(4-((3-hydroxyazetidin-3-yl)ethynyl)phenyl)ethyl)-6-phenyl-1,3-oxazinan-2-one and methyl chloroformate following a procedure analogous to that described in Example 14. LC-MS Method 1 t$_R$=1.43 min, m/z=507, 449; $^1$H NMR (CDCl$_3$) 1.12 (s, 3H), 1.19 (s, 3H), 1.52 (d, 3H), 2.10-2.45 (5H), 2.83 (m, 1H), 3.69 (s, 3H), 4.15 (d, 2H), 4.33 (d, 2H), 5.66 (q, 1H), 6.87 (d, 2H), 7.17 (d, 2H), 7.30-7.40 (5H).

Example 27

Methyl 3-((4-((S)-1-((S)-6-(2-hydroxy-2-methylpropyl)-2-oxo-6-phenyl-1,3-oxazinan-3-yl)ethyl)phenyl)ethynyl)-3-(methoxycarbonyloxy)azetidine-1-carboxylate

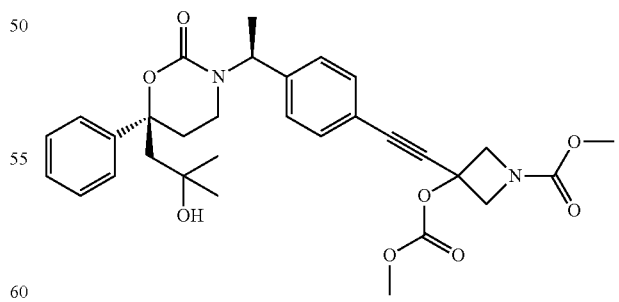

The title compound was isolated as a byproduct from the procedure of Example 26. LC-MS Method 1 t$_R$=1.65 min, m/z=507; $^1$H NMR (CDCl$_3$) 1.12 (s, 3H), 1.19 (s, 3H), 1.52 (d, 3H), 2.10-2.45 (5H), 2.83 (m, 1H), 3.70 (s, 3H), 3.84 (s, 3H), 4.33 (d, 2H), 4.42 (d, 2H), 5.65 (q, 1H), 6.90 9d, 2H), 7.22 (d, 2H), 7.27-7.40 (5H).

Example 28

(S)-6-(2-hydroxy-2-methylpropyl)-3-((S)-1-(4-((2-methoxypyridin-4-yl)ethynyl)phenyl)ethyl)-6-phenyl-1,3-oxazinan-2-one

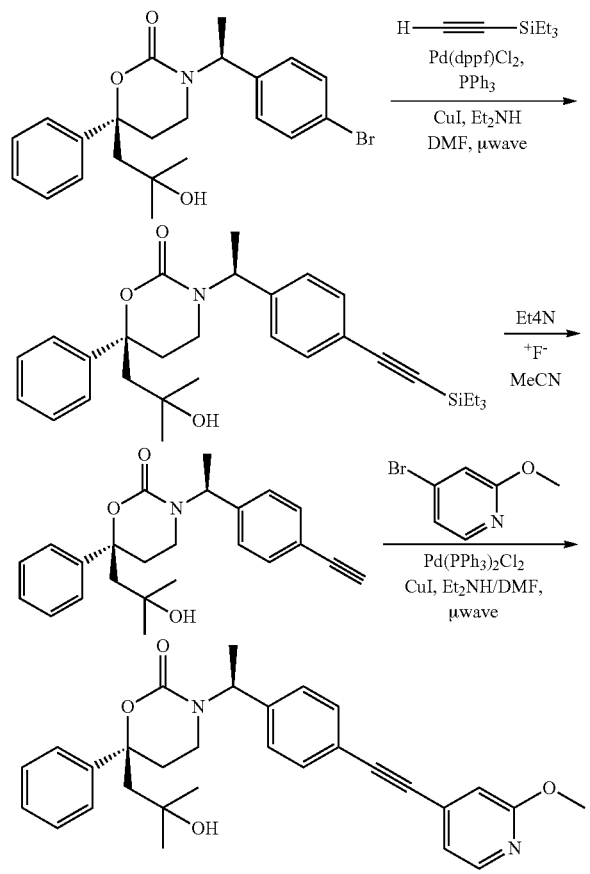

Step 1.

(S)-3-((S)-1-(4-bromophenyl)ethyl)-6-(2-hydroxy-2-methylpropyl)-6-phenyl-1,3-oxazinan-2-one (50 mg, 0.116 mmol), CuI (7 mg, 30% mol), Pd(dppf)Cl₂.CH₂Cl₂ (14 mg, 15% mol), Et₂NH (1 mL, excess), dry DMF (1.5 mL), PPh₃ (5 mg, cat qty) were mixed, degassed, refilled with nitrogen gas (3×). Triethyl(ethynyl)silane (500 µL, excess) was added via a syringe and the mixture was heated in the microwave for 30 min at 120° C. LC-MS showed the reaction was complete. The mixture was filtered, diluted with ether (60 mL), washed with satd aq NH₄Cl (2×10 mL) and brine (10 mL), and dried over Na₂SO₄. After filtration and concentration, the residue was purified by chromatography on a 12 g silica cartridge eluted with a 0-50% EtOAc in hexanes gradient to afford (S)-6-(2-hydroxy-2-methylpropyl)-6-phenyl-3-((S)-1-(4-((triethylsilyl)ethynyl)phenyl)ethyl)-1,3-oxazinan-2-one (54.8 mg, 96%) as a dark oil.

Step 2.

To a solution of (S)-6-(2-hydroxy-2-methylpropyl)-6-phenyl-3-((S)-1-(4-((triethylsilyl)ethynyl)phenyl)ethyl)-1,3-oxazinan-2-one (184 mg, 0.375 mmol) in acetonitrile (5 mL) was added tetraethylammonium fluoride (112 mg, 2 equiv). The mixture was stirred for 3 h at rt and LC-MS showed the reaction was complete. The mixture was concentrated and purified by chromatography on a 12 g silica cartridge, eluted with a 70-100% EtOAc in hexanes gradient, to afford (S)-3-((S)-1-(4-ethynylphenyl)ethyl)-6-(2-hydroxy-2-methylpropyl)-6-phenyl-1,3-oxazinan-2-one (128 mg, 91%) as a white solid.

Step 3.

A mixture of (S)-3-((S)-1-(4-ethynylphenyl)ethyl)-6-(2-hydroxy-2-methylpropyl)-6-phenyl-1,3-oxazinan-2-one (10 mg, 0.027 mmol), 4-bromo-2-methoxypyridine (10 mg, 2 equiv), CuI (0.5 mg, 10% mol), Pd(PPh₃)₂Cl₂ (1.9 mg, 10% mol), diethylamine (1 mL), dry DMF (1 mL) was degassed, refilled with nitrogen gas (3×). The mixture was then heated in the microwave for 45 min at 120° C. LC-MS found the reaction was complete. The mixture was filtered, concentrated, acidified with 5% aq HCl and purified by prep HPLC to afford (S)-6-(2-hydroxy-2-methylpropyl)-3-((S)-1-(4-((2-methoxypyridin-4-yl)ethynyl)phenyl)ethyl)-6-phenyl-1,3-oxazinan-2-one (1.4 mg). LC-MS Method 1 $t_R$=1.92 min, m/z 485 (M+1); ¹H NMR (CD₃OD) 7.41-7.27 (m, 7H), 6.97 (m, 4H), 5.55 (q, 1H), 3.92 (s, 3H), 3.04 (m, 1H), 2.49 (m, 2H), 2.21 (m, 1H), 2.14 (s, 2H), 1.53 (d, 3H), 1.28 (t, 1H), 1.26 (s, 3H), 0.96 (s, 3H).

Example 29

(S)-6-(2-hydroxy-2-methylpropyl)-3-((S)-1-(4-((2-oxo-1,2-dihydropyridin-4-yl)ethynyl)phenyl)ethyl)-6-phenyl-1,3-oxazinan-2-one

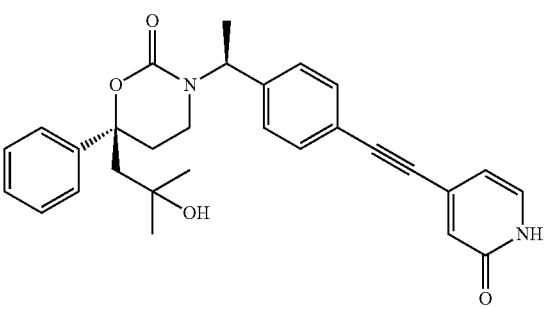 [SMILES: C[C@@H](c1ccc(C#Cc2cc[nH]c(=O)c2)cc1)N1CC[C@](CC(C)(C)O)(c2ccccc2)OC1=O]

The title compound was prepared from (S)-3-((S)-1-(4-ethynylphenyl)ethyl)-6-(2-hydroxy-2-methylpropyl)-6-phenyl-1,3-oxazinan-2-one and 4-iodopyridin-2(1H)-one following a procedure analogous to that described in Example 28 Step 3. LC-MS Method 1 $t_R$=1.3 min, m/z=471 (M+1). ¹H NMR (CD₃OD) 7.44-7.28 (m, 8H), 6.97 (d, 2H), 6.64 (s, 1H), 6.44 (dd, 1H), 5.54 (q, 1H), 3.02 (dt, 1H), 2.49 (m, 2H), 2.21 (m, 1H), 2.15 (s, 2H), 1.53 (d, 3H), 1.26 (s, 3H), 0.96 (s, 3H).

Example 30

(S)-6-(2-Hydroxy-2-methyl-propyl)-3-{(S)-1-[4-(1-methyl-2-oxo-1,2-dihydro-pyridin-4-ylethynyl)-phenyl]ethyl}-6-phenyl-[1,3]oxazinan-2-one

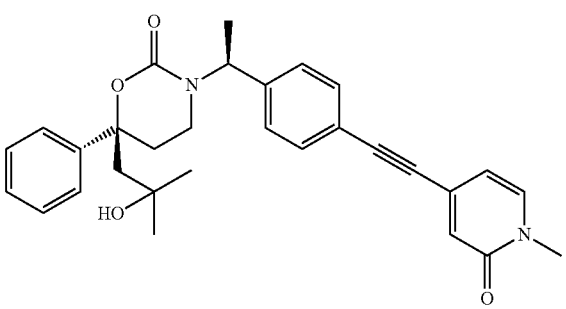

CuI (68 mg), Pd(PPh₃)₂Cl₂ (125 mg), and NEt₃ (0.82 mL) were added successively to a flask charged with a stir bar, 4-bromo-1-methyl-1H-pyridin-2-one (0.38 g), 3-[(S)-1-(4-ethynyl-phenyl)-ethyl]-(S)-6-(2-hydroxy-2-methyl-propyl)-6-phenyl-[1,3]oxazinan-2-one (0.61 g), and N,N-dimethylformamide (3 mL) and kept at room temperature under argon atmosphere. The resulting mixture was heated to 100° C. and stirred at this temperature for 4 h. After cooling the mixture to ambient temperature, water was added and the resulting mixture was extracted with ethyl acetate. The combined organic extracts were washed with water and brine and dried (MgSO$_4$). The solvent was evaporated and the residue was chromatographed on silica gel twice (first chromatography: ethyl acetate/methanol 1:0->4:1; second chromatography: dichloromethane/methanol 19:1->9:1) to afford the title compound as an oil which crystallized from ethyl acetate. Yield: 0.27 g (34% of theory); LC-MS (Method 1): t$_R$=3.41 min; Mass spectrum (ESI$^+$): m/z=485 [M+H]$^+$.

3-[(S)-1-(4-Ethynyl-phenyl)-ethyl]-(S)-6-(2-hydroxy-2-methyl-propyl)-6-phenyl-[1,3]oxazinan-2-one

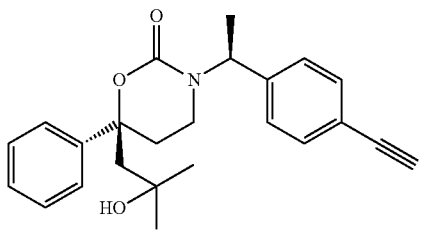

nBu$_4$NF (1 mol/L in tetrahydrofuran, 4.90 mL) was added to a solution of (S)-6-(2-hydroxy-2-methyl-propyl)-6-phenyl-3-[(S)-1-(4-trimethylsilylethynyl-phenyl)-ethyl]-[1,3]oxazinan-2-one (2.00 g) in tetrahydrofuran (20 mL) at room temperature. The solution was stirred for 1 h at room temperature and then concentrated under reduced pressure. Ethyl acetate was added to the residue and the resulting mixture was washed with water and brine. The organic phase was dried (MgSO$_4$) and the solvent was evaporated to afford the title compound as an oil that solidified on standing. Yield: 1.60 g (95% of theory); LC-MS (Method 1): t$_R$=3.64 min; Mass spectrum (ESI$^+$): m/z=378 [M+H]$^+$.

(S)-6-(2-Hydroxy-2-methyl-propyl)-6-phenyl-3-[(S)-1-(4-trimethylsilylethynyl-phenyl)-ethyl]-[1,3]oxazinan-2-one

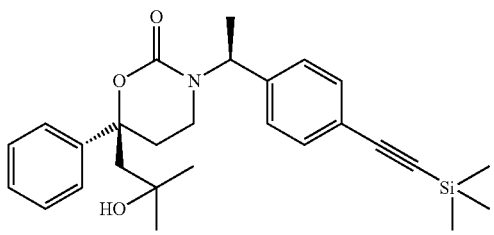

CuI (0.18 g), Pd(PPh$_3$)$_2$Cl$_2$ (0.33 g), and NEt$_3$ (2.22 mL) were added successively to a flask charged with a stir bar, trimethylsilylacetylene (1.31 mL), (S)-3-[1-(4-bromo-phenyl)-ethyl]-6-(2-hydroxy-2-methyl-propyl)-6-phenyl-[1,3]oxazinan-2-one (2.00 g), and N,N-dimethylformamide (15 mL) and kept at room temperature under argon atmosphere. The flask was tightly sealed and the mixture was heated to 90° C. The mixture was stirred at 90° C. overnight and then cooled to ambient temperature. Water (80 mL) and ethyl acetate (200 mL) were added and the resulting mixture was filtered over Celite. The organic phase of the filtrate was separated and washed with brine and dried (MgSO$_4$). The solvent was evaporated and the residue was chromatographed on silica gel (cyclohexane/ethyl acetate 3:1->0:1) to afford the title compound as an oil. Yield: 0.27 g (34% of theory); LC-MS (Method 1): t$_R$=4.27 min; Mass spectrum (ESI$^+$): m/z=450 [M+H]$^+$.

Example 31

(S)-6-(2-Hydroxy-2-methyl-propyl)-3-{(S)-1-[4-(1-methyl-6-oxo-1,6-dihydro-pyridin-3-ylethynyl)-phenyl]ethyl}-6-phenyl-[1,3]oxazinan-2-one

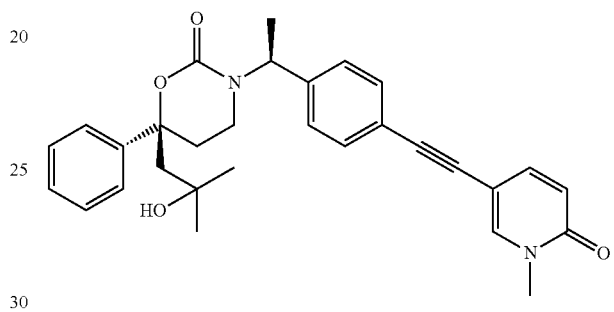

The title compound was prepared from 3-[(S)-1-(4-ethynyl-phenyl)-ethyl]-(S)-6-(2-hydroxy-2-methyl-propyl)-6-phenyl-[1,3]oxazinan-2-one and 5-bromo-1-methyl-1H-pyridin-2-one following a procedure analogous to that described in Example 31. LC-MS (Method 1): t$_R$=3.46 min; Mass spectrum (ESI$^+$): m/z=485 [M+H]$^+$.

BIOLOGICAL TEST EXAMPLE 1

The inhibition of a microsomal preparation of 11β-HSD1 by compounds of the invention was measured essentially as previously described (K. Solly, S. S. Mundt, H. J. Zokian, G. J. Ding, A. Hermanowski—Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 µl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 µL of the test compounds in DMSO previously diluted in half-log increments (8 points) starting at 0.1 mM. After a 10 minute pre-incubation, 50 µL of enzyme solution containing microsomes isolated from CHO cells overexpressing human 11β-HSD1 (10-20 µg/ml of total protein) was added, and the plates were incubated for 90 minutes at rt. The reaction was stopped by adding 50 µl of the SPA beads suspension containing 10 µM 18β-glycyrrhetinic acid, 5 mg/ml protein A coated YSi SPA beads (GE Healthcare) and 3.3 µg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader. Data for compounds tested are shown below in Table 1.

TABLE 1 OF BIOLOGICAL ASSAY RESULTS

| Compound | IC$_{50}$ Range$^a$ | Average % inhibition at 100 nM | IC$_{50}$ (nM) |
|---|---|---|---|
| EXAMPLE 1 | ++ | 90.7 | 3.9 |
| EXAMPLE 2 | ++ | 89.1 | 1.9 |
| EXAMPLE 3 | ++ | 99.8 | 1.1 |
| EXAMPLE 4 | ++ | 86.0 | 13.4 |
| EXAMPLE 5 | ++ | 97.0 | 1.1 |
| EXAMPLE 6 | ++ | 96.7 | 1.2 |
| EXAMPLE 7 | ++ | 93.5 | 5.2 |
| EXAMPLE 8 | ++ | 92.2 | 7.5 |
| EXAMPLE 9 | ++ | 96.6 | 1.0 |
| EXAMPLE 10 | ++ | 84.7 | 6.9 |
| EXAMPLE 11 | ++ | 50.5 | 86.3 |
| EXAMPLE 12 | ++ | 63.7 | 53.4 |
| EXAMPLE 13 | ++ | 82.5 | 12.4 |
| EXAMPLE 14 | ++ | 89.8 | 4.2 |
| EXAMPLE 15 | ++ | 92.4 | 2.4 |
| EXAMPLE 16 | ++ | 95.6 | 3.1 |
| EXAMPLE 17 | ++ | 84.9 | 11.9 |
| EXAMPLE 18 | ++ | 94.5 | 3.7 |
| EXAMPLE 19 | ++ | 97.6 | 2.4 |
| EXAMPLE 20 | ++ | 92.2 | 4.2 |
| EXAMPLE 21 | ++ | 93.7 | 3.4 |
| EXAMPLE 22 | ++ | 93.6 | 1.8 |
| EXAMPLE 23 | ++ | 86.0 | 12.3 |
| EXAMPLE 24 | ++ | 56.1 | 62.3 |
| EXAMPLE 25 | ++ | 94.1 | 3.6 |
| EXAMPLE 26 | ++ | 95.9 | 2.8 |
| EXAMPLE 27 | ++ | 95.8 | 2.4 |
| EXAMPLE 28 | ++ | 102.7 | 1.7 |
| EXAMPLE 29 | ++ | 97.9 | 1.4 |

BIOLOGICAL TEST EXAMPLE 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% CO$_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 μL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% CO$_2$. Negative controls were incubated without radioactive substrate and received the same amount of [$^3$H] cortisone at the end of the incubation. Formation of [$^3$H] cortisol was monitored by analyzing 25 μL of each supernatant in a scintillation proximity assay (SPA). (Solly, K.; Mundt, S. S.; Zokian, H. J.; Ding, G. J.; Hermanowski—Vosatka, A.; Strulovici, B.; Zheng, W. Assay Drug Dev. Technol. 2005, 3, 377-384). Many compounds of the invention showed significant activity in this assay.

BIOLOGICAL TEST EXAMPLE 3

In vitro inhibition of 11 β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 μM) and cortisone (80 nM). Cortisol generated in the reaction is then detected with a competitive immunoassay, involving two HTRF conjugates: cortisol linked to XL665 and anti-cortisol antibody labeled with Europium cryptate. The incubation period for detection reaction was typically 2 hours. The amount of cortisol was determined by reading the time-resolved fluorescence of the wells (Ex 320/75 nm; Em 615/8.5 nm and 665/7.5 nm). The ratio of the two emission signals was then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal.

In the below Table 2, the 11β-HSD 1 inhibitory activities, determined as described above, for Examples 30 and 31 are shown.

TABLE 2

| Example | IC$_{50}$ [nM] |
|---|---|
| 30 | 29 |
| 31 | 30 |

The compounds of the invention are useful for ameliorating or treating disorders or diseases in which decreasing the level of cortisol is effective in treating a disease state. Thus, the compounds of the invention can be used in the treatment or prevention of diabetes mellitus (e.g., type II diabetes), obesity, symptoms of metabolic syndrome, glucose intolerance, hyperglycemia, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypertriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to an 11β-HSD1 inhibitor of the invention, comprise a pharmaceutically acceptable salt of a an 11β-HSD1 inhibitor of the invention and one or more pharmaceutically acceptable carriers therefore. Alternatively, a pharmaceutical composition of the invention may comprise a compound of an 11β-HSD1 inhibitor of the invention or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of an 11β-HSD1 inhibitor of the invention, or an enantiomer, diastereomer, or pharmaceutically acceptable salt thereof or composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of the invention or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitzone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of the invention or composition thereof in a combination therapy with one or more other 11β-HSD1 inhibitors, or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

While this invention has been particularly shown and described with references to example embodiments thereof, it will be understood by those skilled in the art that various changes in form and details may be made therein without departing from the scope of the invention encompassed by the appended claims.

What is claimed is:

1. A compound of Formula (I):

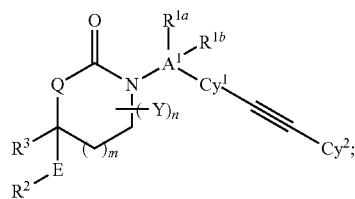

wherein:
R$^{1a}$ and R$^{1b}$ are (a) absent if A$^1$ is a bond, or (b) independently selected from —H, (C$_1$-C$_6$)alkyl, (C$_2$-C$_6$)alkenyl, (C$_2$-C$_6$)alkynyl, or (C$_1$-C$_3$)alkoxy(C$_1$-C$_3$)alkyl, (C$_3$-C$_6$)cycloalkyl or R$^{1a}$ and R$^{1b}$ taken together with the carbon to which they are attached form a (C$_3$-C$_6$)cycloalkyl ring, and the (C$_1$-C$_6$)alkyl, (C$_2$-C$_6$)alkenyl, (C$_2$-C$_6$)alkynyl, (C$_1$-C$_3$)alkoxy(C$_1$-C$_3$)alkoxy, (C$_1$-C$_3$)alkoxy(C$_1$-C$_3$)alkyl, (C$_3$-C$_6$)cycloalkyl, or the cycloalkyl ring formed from R$^{1a}$, R$^{1b}$ and the carbon to which R$^{1a}$ and R$^{1b}$ are attached, are, independently, optionally substituted with up to four groups selected from H, fluorine, cyano, oxo, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl, (C$_1$-C$_6$)alkoxy(C$_1$-C$_6$)alkyl, R$^4$O—, (R$^4$)$_2$N—, R$^4$O$_2$C—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, heterocyclyl, heteroaryl, aryl-amino and heteroarylamino;

A$^1$ is absent or a carbon atom;

Cy$^1$ is aryl, heteroaryl, monocyclic cycloalkyl or monocyclic heterocyclyl and is optionally substituted with 1 to 4 groups independently selected from halogen, —CN, —NO$_2$, —NH$_2$, —OH, —COOH, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl, hydroxy(C$_1$-C$_6$)alkoxy, (C$_4$-C$_7$)cycloalkylalkyl, (C$_4$-C$_7$)cycloalkylalkoxy, (C$_3$-C$_6$)cycloalkyl(C$_2$-C$_4$)alkynyl, halo(C$_1$-C$_6$)alkyl, halo(C$_2$-C$_6$)alkenyl, halo(C$_3$-C$_6$)cycloalkyl, halo(C$_4$-C$_7$)cycloalkylalkyl, halo(C$_1$-C$_6$)alkoxy, halo(C$_3$-C$_6$)cycloalkoxy, halo(C$_4$-C$_7$)cycloalkylalkoxy, (C$_1$-C$_6$)alkoxy(C$_1$-C$_6$)alkoxy, halo(C$_1$-C$_6$)alkoxy(C$_1$-C$_6$)alkoxy, (C$_1$-C$_6$)alkoxy(C$_1$-C$_6$)alkyl or halo(C$_1$-C$_6$)alkoxy(C$_1$-C$_6$)alkyl (C$_1$-C$_6$)alkylthio, (C$_3$-C$_6$)cycloalkylthio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH$_2$, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano(C$_1$-C$_6$)alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$;

Cy$^2$ is (C$_1$-C$_6$)alkyl, (C$_2$-C$_6$)alkenyl, (C$_2$-C$_6$)alkynyl, (C$_1$-C$_3$)alkoxy(C$_1$-C$_3$)alkoxy, (C$_1$-C$_3$)alkoxy(C$_1$-C$_3$)alkyl, aryl, heteroaryl, cycloalkyl or heterocyclyl, and is optionally substituted with 1 to 4 groups independently selected from halogen, —CN, —NO$_2$, —NH$_2$, —OH, —COOH, —COOR$^6$, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, (C$_3$-C$_6$)cycloalkoxy, hydroxy(C$_1$-C$_6$)alkyl, hydroxy(C$_3$-C$_6$)cycloalkyl, hydroxy(C$_2$-C$_6$)alkenyl, hydroxy(C$_1$-C$_6$)alkoxy, (C$_4$-C$_7$)cycloalkylalkyl, (C$_4$-C$_7$)cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkylthio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NHR$^7$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH$_2$, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano$(C_1-C_6)$alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$;

E is (a) a bond or (b) $(C_1-C_3)$alkylene or $(C_1-C_2)$alkylenyloxy, wherein the O is attached to R$^2$, each of which is optionally substituted with 1 to 4 groups independently selected from methyl, ethyl, trifluoromethyl and oxo;

R$^2$ is $(C_1-C_6)$alkyl, aryl, heteroaryl, cycloalkyl or heterocyclyl and is optionally substituted with up to 4 groups independently selected from halogen, —CN, —NO$_2$, —NH$_2$, —OH, —COOH, $(C_1-C_6)$alkyl, $(C_2-C_6)$alkenyl, $(C_2-C_6)$alkynyl, $(C_1-C_6)$alkoxy, $(C_3-C_6)$cycloalkyl, $(C_3-C_6)$cycloalkoxy, hydroxy$(C_1-C_6)$alkyl, hydroxy$(C_3-C_6)$cycloalkyl, hydroxy$(C_2-C_6)$alkenyl, hydroxy$(C_1-C_6)$alkoxy, $(C_4-C_7)$cycloalkylalkyl, $(C_4-C_7)$cycloalkylalkoxy, $(C_3-C_6)$cycloalkyl$(C_2-C_4)$alkynyl, halo$(C_1-C_6)$alkyl, halo$(C_2-C_6)$alkenyl, halo$(C_3-C_6)$cycloalkyl, halo$(C_4-C_7)$cycloalkylalkyl, halo$(C_1-C_6)$alkoxy, halo$(C_3-C_6)$cycloalkoxy, halo$(C_4-C_7)$cycloalkylalkoxy, $(C_1-C_6)$alkoxy$(C_1-C_6)$alkoxy, halo$(C_1-C_6)$alkoxy$(C_1-C_6)$alkoxy, $(C_1-C_6)$alkoxy$(C_1-C_6)$alkyl, halo$(C_1-C_6)$alkoxy$(C_1-C_6)$alkyl, $(C_1-C_6)$alkylthio, $(C_3-C_6)$cycloalkylthio, —SR$^9$, —S(=O)R$^6$, —S(=O)R$^7$, —S(=O)R$^9$, —S(=O)$_2$R$^6$, —S(=O)$_2$R$^7$, —S(=O)$_2$R$^9$, —NHR$^6$, —N(R$^6$), —C(=O)R$^6$, —C(=O)NH$_2$, —S(=O)$_2$NH$_2$, —C(=O)NHR$^6$, —C(=O)NR$^6$R$^6$, —C(=O)R$^8$, —S(=O)$_2$NHR$^6$, —S(=O)$_2$N(R$^6$)$_2$, —S(=O)$_2$R$^8$, —NHC(=O)R$^6$, —V$^1$—NHC(=O)R$^6$, —NHS(=O)$_2$R$^6$, —V$^1$—NHS(=O)$_2$R$^6$, —V$^1$—C(=O)R$^6$, heteroaryl, aryl, heterocyclyl, oxo, —V$^1$—NH$_2$, —V$^1$—NHR$^6$, —V$^1$—N(R$^6$)$_2$, —C(=O)R$^7$, —C(=O)NHR$^7$, —C(=O)NR$^6$R$^7$, —C(=O)N(R$^7$)$_2$, —S(=O)$_2$NHR$^7$, —S(=O)$_2$NR$^6$R$^7$, —S(=O)$_2$N(R$^7$)$_2$, cyano$(C_1-C_6)$alkyl, —V$^1$—C(=O)NH$_2$, —V$^1$—C(=O)NHR$^6$, —V$^1$—C(=O)N(R$^6$)$_2$, —V$^1$—C(=O)NHR$^7$, —V$^1$—C(=O)NR$^6$R$^7$ and —V$^1$—C(=O)N(R$^7$)$_2$;

R$^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, and $(C_1-C_3)$alkoxy$(C_1-C_3)$alkyl and is optionally substituted with up to four groups independently selected from H, —F, —CN, oxo, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl, R$^4$O—, (R$^4$)$_2$N—, R$^4$O$_2$C—, R$^4$C(=O)O—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, spirocycloalkyl, heterocyclyl (which in turn is optionally substituted with alkyl, haloalkyl, halogen or oxo), heteroaryl (which in turn is optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo), arylamino (which in turn is optionally substituted with alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido) and heteroarylamino (which in turn is optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo);

Y is $(C_1-C_6)$alkyl, halo$(C_1-C_6)$alkyl or oxo;

n is 0, 1 or 2;

m is 1;

Q is O;

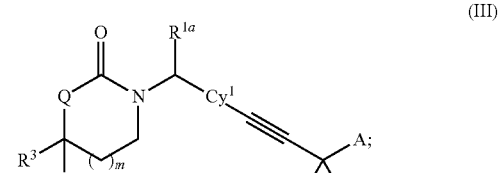

(III)

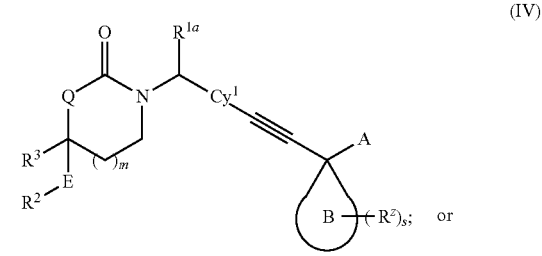

(IV)

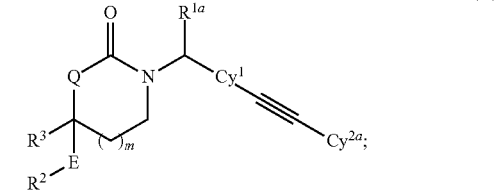

(V)

wherein:

R$^{1a}$ is optionally substituted $(C_1-C_6)$alkyl;

R$^x$ and R$^y$ are, independently, optionally substituted $(C_1-C_6)$alkyl;

A is selected from —CN, —NO$_2$, —NH$_2$, —OH, —COOH, —COOR$^6$, $(C_1-C_6)$alkyl, $(C_2-C_6)$alkenyl, $(C_2-C_6)$alkynyl, $(C_1-C_6)$alkoxy, $(C_3-C_6)$cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, ($C_3$-$C_6$)cycloalkylhio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)_2$, —$C(=O)R^6$, —$C(=O)NH_2$, —$S(=O)_2NH_2$, —$C(=O)NHR^6$, —$C(=O)NHR^7$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)R^7$, —$NHC(=O)NH_2$, —$NHC(=O)NHR^6$, —$NHC(=O)NR^6R^6$, oxooxazolidinyl, —$OC(=O)OR^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano($C_1$-$C_6$)alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$;

B is cycloalkyl or heterocyclyl;

s is 0, 1, 2 or 3;

each $R^z$ is independently selected from —CN, —$NO_2$, —$NH_2$, —OH, —COOH, —$COOR^6$, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, ($C_3$-$C_6$)cycloalkylhio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)_2$, —$C(=O)R^6$, —$C(=O)NH_2$, —$S(=O)_2NH_2$, —$C(=O)NHR^6$, —$C(=O)NHR^7$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)R^7$, —$NHC(=O)NH_2$, —$NHC(=O)NHR^6$, —$NHC(=O)NR^6R^6$, oxooxazolidinyl, —$OC(=O)OR^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano($C_1$-$C_6$)alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$;

each $R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl;

each $R^6$ is independently ($C_1$-$C_6$)alkyl, ($C_2$-$C_6$)alkenyl, ($C_2$-$C_6$)alkynyl or ($C_1$-$C_6$)alkoxy;

$V^1$ is ($C_1$-$C_6$)alkylene, ($C_1$-$C_6$)alkenylene, ($C_1$-$C_6$)alkynylene or ($C_1$-$C_6$)alkyleneoxy;

each $R^7$ is independently ($C_3$-$C_6$)cycloalkyl or ($C_3$-$C_6$)cycloalkoxy;

$R^8$ is heterocyclyl; and $R^9$ is ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl or halo($C_1$-$C_6$)alkoxy($C_1$-$C_6$)alkyl;

or a pharmaceutically acceptable salt, enantiomer or diastereomer thereof.

2. The compound of claim 1, wherein the compound is represented by structural formula (II), (III), (IV) or (V):

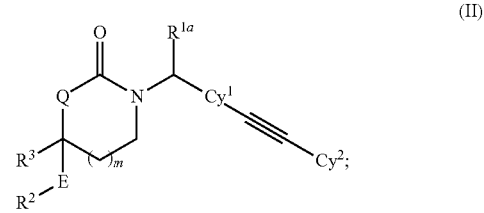

(II)

$R^{1a}$ is optionally substituted ($C_1$-$C_6$)alkyl; and $Cy^{2a}$ is an aryl, heteroaryl or heterocyclyl group, and is optionally substituted with 1 to 4 groups independently selected from halogen, —CN, —$NO_2$, —$NH_2$, —OH, —COOH, —$COOR^6$, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, ($C_3$-$C_6$)cycloalkoxy, hydroxy($C_1$-$C_6$)alkyl, hydroxy($C_3$-$C_6$)cycloalkyl, hydroxy($C_2$-$C_6$)alkenyl, hydroxy($C_1$-$C_6$)alkoxy, ($C_4$-$C_7$)cycloalkylalkyl, ($C_4$-$C_7$)cycloalkylalkoxy, ($C_3$-$C_6$)cycloalkyl($C_2$-$C_4$)alkynyl, halo($C_1$-$C_6$)alkyl, halo($C_2$-$C_6$)alkenyl, halo($C_3$-$C_6$)cycloalkyl, halo($C_4$-$C_7$)cycloalkylalkyl, halo($C_1$-$C_6$)alkoxy, halo($C_3$-$C_6$)cycloalkoxy, halo($C_4$-$C_7$)cycloalkylalkoxy, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxy($C_1$-$C_6$)alkyl, halo($C_1$-$C_6$)alkoxy($C_1$-$C_6$)alkyl, ($C_1$-$C_6$)alkylthio, ($C_3$-$C_6$)cycloalkylhio, —$SR^9$, —$S(=O)R^6$, —$S(=O)R^7$, —$S(=O)R^9$, —$S(=O)_2R^6$, —$S(=O)_2R^7$, —$S(=O)_2R^9$, —$NHR^6$, —$N(R^6)_2$, —$C(=O)R^6$, —$C(=O)NH_2$, —$S(=O)_2NH_2$, —$C(=O)NHR^6$, —$C(=O)NHR^7$, —$C(=O)NR^6R^6$, —$C(=O)R^8$, —$S(=O)_2NHR^6$, —$S(=O)_2N(R^6)_2$, —$S(=O)_2R^8$, —$NHC(=O)R^6$, —$NHC(=O)R^7$, —$NHC(=O)NH_2$, —$NHC(=O)NHR^6$, —$NHC(=O)NR^6R^6$, oxooxazolidinyl, —$OC(=O)OR^6$, —$V^1$—$NHC(=O)R^6$, —$NHS(=O)_2R^6$, —$V^1$—$NHS(=O)_2R^6$, —$V^1$—$C(=O)R^6$, heteroaryl, aryl, heterocyclyl, oxo, —$V^1$—$NH_2$, —$V^1$—$NHR^6$, —$V^1$—$N(R^6)_2$, —$C(=O)R^7$, —$C(=O)NHR^7$, —$C(=O)NR^6R^7$, —$C(=O)N(R^7)_2$, —$S(=O)_2NHR^7$, —$S(=O)_2NR^6R^7$, —$S(=O)_2N(R^7)_2$, cyano($C_1$-$C_6$)alkyl, —$V^1$—$C(=O)NH_2$, —$V^1$—$C(=O)NHR^6$, —$V^1$—$C(=O)N(R^6)_2$, —$V^1$—$C(=O)NHR^7$, —$V^1$—$C(=O)NR^6R^7$ and —$V^1$—$C(=O)N(R^7)_2$;

or a pharmaceutically acceptable salt, enantiomer or diastereomer thereof.

3. The compound of claim 2, wherein $Cy^1$ is an optionally cyclohexyl, phenyl, pyridyl, pyrimidinyl, thiazolyl, triazolyl, or benzothiazolyl group; $R^{1a}$ is an optionally substituted methyl or ethyl group; and Q is O.

4. The compound of claim 3, wherein the compound is represented by structural formula (II-C), (III-D), (IV-C) or (V-C):

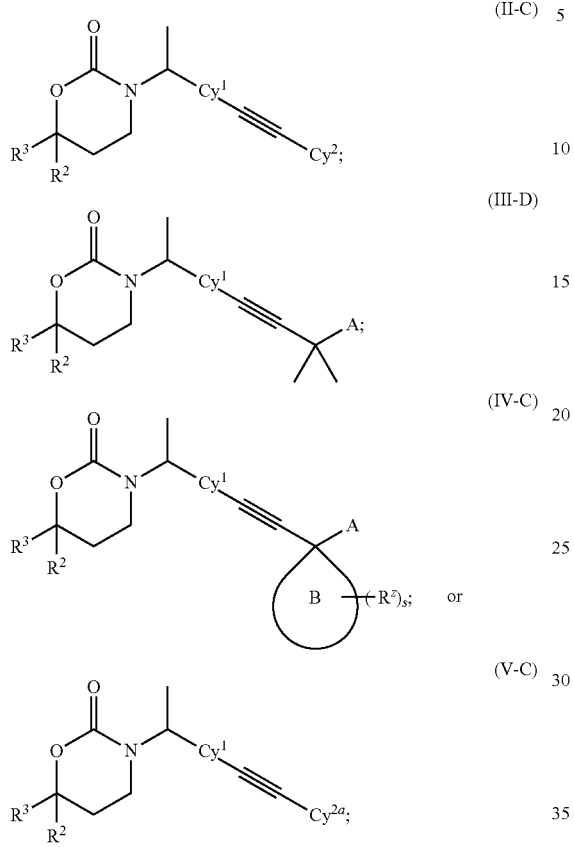

or a pharmaceutically acceptable salt, enantiomer or diastereomer thereof;
wherein:
- $Cy^2$ is an optionally substituted methyl, ethyl, propyl, butyl, pentyl, hexyl, cyclopropyl, cyclobutyl, cyclopentyl, cyclohexyl, phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl, piperidinyl, pyrrolidinyl, azetidinyl, morpholinyl, tetrahydropyranyl, dihydropyranyl, tetrahydrofuranyl, oxetanyl, indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, oxodihydrobenzimidazolyl, piperazinyl, oxodihydropyrrolyl, or 1,1-dioxo-hexahydro-1,2-thiazinyl group;
- B is an optionally substituted cyclobutyl, cyclopentyl, cyclohexyl, piperidinyl, pyrrolidinyl, azetidinyl, morpholinyl, tetrahydropyranyl, dihydropyranyl, tetrahydrofuranyl or oxetanyl group; and
- $Cy^{2a}$ is an optionally substituted phenyl, pyridyl, pyridazinyl, pyrimidinyl, pyrazinyl, thiazolyl, oxazolyl, isoxazolyl, pyrazolyl, oxadiazolyl, thiadiazolyl, triazolyl, furyl, thienyl, benzimidazolyl, benzotriazolyl, benzothiazolyl, imidazopyridazinyl, triazolopyridinyl, oxodihydropyridyl, oxodihydropyridazinyl, oxodihydropyrimidinyl, oxodihydropyrazinyl, oxoindolinyl, oxodihydroquinolinyl, oxodihydropyrrolopyridinyl indazolyl, imidazopyridinyl, imidazopyrimidinyl, pyrrolopyridinyl, tetrazolopyridinyl, tetrazolopyridazinyl, triazolopyrimidinyl, triazolopyridazinyl, oxodihydropurinyl, or oxodihydrobenzimidazolyl group.

5. The compound of claim 4, wherein $Cy^1$ is optionally substituted phenyl.

6. The compound of claim 5, wherein $Cy^2$ is methyl, ethyl, cyclopentyl, cyclohexyl, phenyl, pyridyl, oxodihydropyridyl, piperidinyl, azetidinyl or tetrahydropyranyl group, each optionally substituted with one to three groups independently selected from —$NH_2$, —OH, —COOH, —COOMe, —OMe, cyclopropylcarbamoyl; —C(=O)$NMe_2$, azetidinylcarbonyl, —NHC(=O)Me, —NHC(=O)OMe, cyclopropanecarboxamido, —NHC(=O)$NH_2$, —NHC(=O)NHMe, —NHC(=O)$NMe_2$, oxooxazolidinyl, —OC(=O)OMe, and —NHS(=O)$_2$Me;
- A is selected from —$NH_2$, —OH, —COOH, —COO($C_1$-$C_6$)alkyl, ($C_1$-$C_6$)alkoxy, —C(=O)NH($C_3$-$C_6$)cycloalkyl, —C(=O)N{($C_1$-$C_6$)alkyl}{($C_1$-$C_6$)alkyl}, azetidinylcarbonyl, —NHC(=O)($C_1$-$C_6$)alkyl, —NHC(=O)O($C_1$-$C_6$)alkyl, —NHC(=O)($C_3$-$C_6$)cycloalkyl, —NHC(=O)$NH_2$, —NHC(=O)NH($C_1$-$C_6$)alkyl, —NHC(=O)N{($C_1$-$C_6$)alkyl}{($C_1$-$C_6$)alkyl}, oxooxazolidinyl, —OC(=O)O($C_1$-$C_6$)alkyl, and —NHS(=O)$_2$($C_1$-$C_6$)alkyl; and
- $Cy^{2a}$ is pyridyl or oxodihydropyridyl each optionally substituted with one to three groups independently selected from —$NH_2$, —OH, —COOH, —COOMe, —OMe, cyclopropylcarbamoyl, —C(=O)$NMe_2$, azetidinylcarbonyl, —NHC(=O)Me, —NHC(=O)OMe, cyclopropanecarboxamido, —NHC(=O)$NH_2$, —NHC(=O)NHMe, —NHC(=O)$NMe_2$, oxooxazolidinyl, —OC(=O)OMe, and —NHS(=O)$_2$Me.

7. The compound of claim 6, wherein the compound is represented by structural formula (II-D), (III-E), (IV-D) or (V-C):

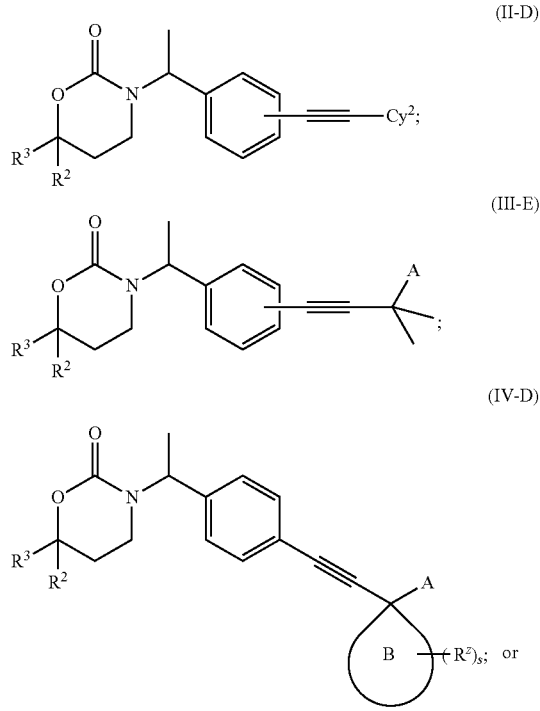

-continued

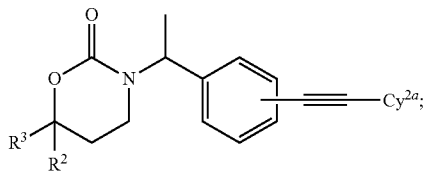

(V-D)

or a pharmaceutically acceptable salt, enantiomer or diastereomer thereof.

8. The compound of claim 7, wherein $R^3$ is $(C_3-C_6)$alkenyl, hydroxy$(C_2-C_5)$alkyl, cyano$(C_2-C_5)$alkyl, dihydroxy$(C_3-C_5)$alkyl, ω-H$_2$NCO$(C_1-C_5)$alkyl, $(C_1-C_2)$alkoxy$(C_1-C_4)$alkyl, H$_2$NSO$_2$O$(C_2-C_5)$alkyl, H$_2$NSO$_2$NH$(C_2-C_5)$alkyl, oxo$(C_2-C_5)$alkyl, MeC(=O)NH$(C_2-C_5)$alkyl, MeSO$_2$NH$(C_2-C_5)$alkyl, or MeSO$_2$NH$(C_2-C_5)$alkyl.

9. The compound of claim 8, wherein $R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC≡N)NH—, MeS—, MeSO$_2$—, MeSO$_2$N(Me)—, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe.

10. The compound of claim 9, wherein $R^2$ is an optionally substituted $(C_1-C_6)$alkyl, aryl, heteroaryl or cycloalkyl group; and $R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC≡N)NH—, MeS—, MeSO$_2$—, MeSO$_2$N(Me)—, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe.

11. The compound of claim 10, wherein
$R^2$ is phenyl, fluorophenyl, isopropyl, cyclopropyl, t-butyl or trifluoroethyl, and the group represented by $R^2$ is optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen, cyano and nitro; and
$R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC≡N)NH—, MeS—, MeSO$_2$— MeSO$_2$N(Me)-, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe.

12. The compound of claim 11, wherein
$R^2$ is phenyl, fluorophenyl, isopropyl, cyclopropyl, t-butyl or trifluoroethyl, and the group represented by $R^2$ is optionally substituted with one to three groups independently selected from $(C_1-C_4)$alkyl, $(C_1-C_4)$alkoxy, $(C_1-C_4)$haloalkyl, $(C_1-C_4)$haloalkoxy, halogen, cyano and nitro;
$R^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC≡N)NH—, MeS—, MeSO$_2$— MeSO$_2$N(Me)—, MeS(=O)$_2$NHC(=O)—, imidazolylamino-, imidazolyl, tetrazolyl, spirocyclopropyl, FCH$_2$CH$_2$NH, 1-pyrrolidinyl, 3-fluoro-1-pyrrolidinyl, 3-oxo-1-piperazinyl, 1-azetidinyl, 1,1-dioxo-2-isothiazolidinyl, 2-oxo-1-pyrrolidinyl, H$_2$NCONH—, H$_2$NCO$_2$—, HOCH$_2$CH$_2$O—, MeNH—, Me$_2$N— and MeCONMe;
the group represented by $Cy^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl;
the group represented by $Cy^2$ is optionally substituted with one to three groups independently selected from —NH$_2$, —OH, —COOH, —COOR$^6$, —R$^6$, —C(=O)NHR$^7$, —C(=O)NR$^6$R$^6$, —C(=O)R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, and —NHS(=O)$_2$R$^6$;
A is selected from —NH$_2$, —OH, —COOH, —COOR$^6$, —R$^6$, —C(=O)NHR$^7$; —C(=O)NR$^6$R$^6$, —C(=O)R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, and —NHS(=O)$_2$R$^6$;
B is an cyclobutyl, cyclopentyl, cyclohexyl, piperidinyl, pyrrolidinyl, azetidinyl, morpholinyl, tetrahydropyranyl, dihydropyranyl, tetrahydrofuranyl or oxetanyl group;
each $R^z$ is independently selected from —COOR$^6$, $(C_1-C_6)$alkyl and —OC(=O)OR$^6$; and
the group represented by $Cy^{2a}$ is optionally substituted with one to three groups independently selected from —NH$_2$, —OH, —COOH, —COOMe, —OMe, cyclopropylcarbamoyl, —C(=O)NMe$_2$, azetidinylcarbonyl, —NHC(=O)Me, —NHC(=O)OMe, cyclopropanecarboxamido, —NHC(=O)NH$_2$, —NHC(=O)

NHMe, —NHC(=O)NMe$_2$, oxooxazolidinyl, —OC(=O)OMe, and —NHS(=O)$_2$Me.

13. The compound of claim 12, wherein
R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me;
R$^3$ is 2-methylallyl, MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl;
the group represented by Cy$^1$ is optionally substituted with 1 to 4 groups independently selected from halo, methyl, trifluoromethyl, hydroxy, methoxy, methoxycarbonyl, carboxy, ethoxycarbonylmethoxy, 2-hydroxy-2-methylpropoxy, cyano, difluoromethoxy, t-butoxycarbonyl, hydroxy, hydroxymethyl, 2-hydroxyethyl, 2-hydroxy-2-propyl, methoxymethyl, methylsulfonyl, methylsulfonylamino and benzyloxycarbonyl;
the group represented by Cy$^2$ is optionally substituted with one to three groups independently selected from —NH$_2$, —OH, —COOH, —COOR$^6$, —R$^6$, —C(=O)NHR$^7$, —C(=O)NR$^6$R$^6$, —C(=O)R$^8$, —NHC(=O)R$^6$, —NHC(=O)R$^7$, —NHC(=O)NH$_2$, —NHC(=O)NHR$^6$, —NHC(=O)NR$^6$R$^6$, oxooxazolidinyl, —OC(=O)OR$^6$, and —NHS(=O)$_2$R$^6$;
A is selected from —NH$_2$, —OH, —COOH, —COO(C$_1$-C$_6$)alkyl, (C$_1$-C$_6$)alkoxy, —C(=O)NH(C$_3$-C$_6$)cycloalkyl, —C(=O)N{(C$_1$-C$_6$)alkyl}{(C$_1$-C$_6$)alkyl}, azetidinylcarbonyl, —NHC(=O)(C$_1$-C$_6$)alkyl, —NHC(=O)O(C$_1$-C$_6$)alkyl, —NHC(=O)(C$_3$-C$_6$)cycloalkyl, —NHC(=O)NH$_2$, —NHC(=O)NH(C$_1$-C$_6$)alkyl, —NHC(=O)N{(C$_1$-C$_6$)alkyl}{(C$_1$-C$_6$)alkyl}, oxooxazolidinyl, —OC(=O)O(C$_1$-C$_6$)alkyl, and —NHS(=O)$_2$(C$_1$-C$_6$)alkyl;
B is an cyclobutyl, cyclopentyl, cyclohexyl, piperidinyl, pyrrolidinyl, azetidinyl, morpholinyl, tetrahydropyranyl, dihydropyranyl, tetrahydrofuranyl or oxetanyl group;
each R$^z$ is independently selected from —COO(C$_1$-C$_6$)alkyl, (C$_1$-C$_6$)alkyl, and —OC(=O)O(C$_1$-C$_6$)alkyl; and
the group represented by Cy$^{2a}$ is optionally substituted with one to three groups independently selected from —NH$_2$, —OH, —COOH, —COOMe, —OMe, cyclopropylcarbamoyl, —C(=O)NMe$_2$, azetidinylcarbonyl, —NHC(=O)Me, —NHC(=O)OMe, cyclopropanecarboxamido, —NHC(=O)NH$_2$, —NHC(=O)NHMe, —NHC(=O)NMe$_2$, oxooxazolidinyl, —OC(=O)OMe, and —NHS(=O)$_2$Me.

14. The compound of claim 13, wherein
R$^2$ is phenyl, fluorophenyl, isopropyl, cyclopropyl, t-butyl, cyclopropylmethyl or trifluoroethyl;
R$^3$ is 2-methylallyl, 2-hydroxy-2-methylpropyl or 2-cyano-2-methylpropyl;
the group represented by Cy$^1$ is optionally substituted with fluoro, chloro, cyano, CONH$_2$, CONHMe, CONMe$_2$, CONHc-Pr, methyl, ethyl, cyclopropyl, CF$_3$ or oxo;
the group represented by Cy$^2$ is optionally substituted with one to three groups independently selected from —NH$_2$, —OH, —COOH, —COOMe, —OMe, cyclopropylcarbamoyl, —C(=O)NMe$_2$, azetidinylcarbonyl, —NHC(=O)Me, —NHC(=O)OMe, cyclopropanecarboxamido, —NHC(=O)NH$_2$, —NHC(=O)NHMe, —NHC(=O)NMe$_2$, oxooxazolidinyl, —OC(=O)OMe, and —NHS(=O)$_2$Me;
A is selected from —NH$_2$, —OH, —COOH, —C(=O)NH(C$_3$-C$_6$)cycloalkyl, —C(=O)N{(C$_1$-C$_6$)alkyl}{(C$_1$-C$_6$)alkyl}, azetidinylcarbonyl, —NHC(=O)(C$_1$-C$_6$)alkyl, —NHC(=O)O(C$_1$-C$_6$)alkyl, —NHC(=O)(C$_3$-C$_6$)cycloalkyl, —NHC(=O)NH$_2$, —NHC(=O)NH(C$_1$-C$_6$)alkyl, —NHC(=O)N{(C$_1$-C$_6$)alkyl}{(C$_1$-C$_6$)alkyl}, oxooxazolidinyl, and —NHS(=O)$_2$(C$_1$-C$_6$)alkyl;
B is an cyclopentyl, cyclohexyl, piperidinyl, azetidinyl or tetrahydropyranyl group;
each R$^z$ is independently selected from —COO(C$_1$-C$_6$)alkyl, (C$_1$-C$_6$)alkyl, and —OC(=O)O(C$_1$-C$_6$)alkyl; and
the group represented by Cy$^{2a}$ is optionally substituted with (C$_1$-C$_6$)alkoxy.

15. A method of treating a subject with a disease or disorder selected from diabetes mellitus, obesity, symptoms of metabolic syndrome, glucose intolerance, hyperglycemia, hypertension, hyperlipidemia, insulin resistance, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, and polycystic ovarian syndrome, comprising the step of administering to the subject an effective amount of the compound of claim 1.

16. A pharmaceutical composition comprising: i) a pharmaceutically acceptable carrier or diluent; and ii) the compound of claim 1; or a pharmaceutically acceptable salt, enantiomer or diastereomer thereof.

* * * * *